United States Patent [19]
Mizuno et al.

[11] Patent Number: 6,001,827
[45] Date of Patent: Dec. 14, 1999

[54] BENZOTHIAZINE DERIVATIVE

[75] Inventors: Akira Mizuno, Kyoto; Makoto Shibata, Ashikaga; Tomoe Iwamori, Ibaraki; Norio Inomata, Mino, all of Japan

[73] Assignee: Suntory Limited, Osaka, Japan

[21] Appl. No.: 09/192,287

[22] Filed: Nov. 16, 1998

Related U.S. Application Data

[60] Division of application No. 08/669,615, Jun. 24, 1996, which is a continuation-in-part of application No. 08/507,239, Aug. 24, 1995, abandoned, and a continuation of application No. PCT/JP94/02194, Dec. 22, 1994.

[30]     Foreign Application Priority Data

Dec. 24, 1993  [JP]  Japan ..................................... 5-345865
Jun. 22, 1995  [JP]  Japan ..................................... 7-177976

[51] Int. Cl.⁶ ........................ C07D 243/08; A61K 31/38; A61K 31/55
[52] U.S. Cl. .......................................... 514/218; 540/575
[58] Field of Search .............................. 514/218; 540/575

[56]            References Cited

U.S. PATENT DOCUMENTS

| | | | |
|---|---|---|---|
| 3,284,450 | 11/1966 | Kraaijeveld et al. | 260/243 |
| 3,770,733 | 11/1973 | Sianesi et al. | 260/243 |
| 5,130,313 | 7/1992 | Comte et al. | 514/253 |
| 5,563,144 | 10/1996 | Damour et al. | 514/253 |

FOREIGN PATENT DOCUMENTS

| | | |
|---|---|---|
| 0 433 149 | 6/1991 | European Pat. Off. |
| 0 686 632 | 12/1995 | European Pat. Off. |
| 2675801 | 10/1992 | France . |
| 46-29 | 1/1971 | Japan . |
| 64-61470 | 3/1989 | Japan . |
| 311059 | 12/1989 | Japan . |
| 2-67274 | 3/1990 | Japan . |
| 255063 | 11/1991 | Japan . |
| 2137987 | 10/1984 | United Kingdom . |
| WO 93-16073 | 8/1993 | WIPO . |

OTHER PUBLICATIONS

Eur. J. Pharmacol., vol. 204, No. 1, 1991, Roger Godbout et al., pp. 97–100.

J. Med. Chem., vol. 36, Apr. 1993, Jean–Luc Malleron et al., pp. 1194–1206.

J. Med. Chem. vol. 34, 1991, Jean–Luc Malleron et al., pp. 2477–2483.

Bioorganic & Medical Chemistry Letters, vol. 3, No. 10, 1993, pp. 1913–1918, New Indole Derivatives as Potent and Selective Serotonin Uptake Inhibitors, Serge Mignani et al.

*Primary Examiner*—Mukund J. Shah
*Assistant Examiner*—Bruck Kifle
*Attorney, Agent, or Firm*—Oblon, Spivak, McClelland, Maier & Neustadt, P.C.

[57]            ABSTRACT

Disclosed are benzothiazine derivatives represented by the following formula (I):

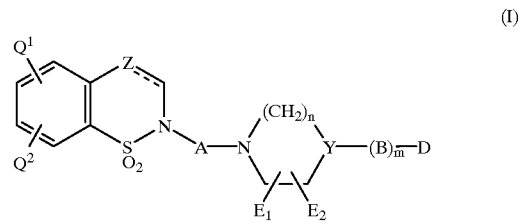

wherein the dashed line indicates the presence or absence of a bond; Z represents one of the following groups:

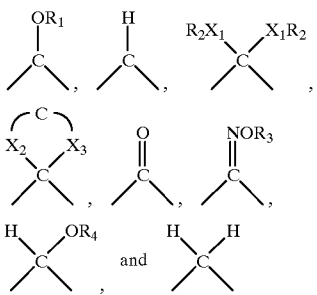

in which $R_1$ and $R_2$ individually represent alkyl, aralkyl or the like, $R_3$ represents H, alkyl or the like, $R_4$ represents H, aralkyl or the like, $X_1$, $X_2$ and $X_3$ individually represent O or S, and G represents substituted or unsubstituted ethylene, trimethylene or the like; $Q_1$ and $Q_2$ individually represent H, OH, halogen, alkoxy or the like; A represents alkylene, alkenylene or the like; Y represents CH, C= or N; when Y is CH, m stands for 0 or 1, n stands for 1 or 2, B represents O, S, carbonyl or the like, when Y is C=, m stands for 1, n stands for 1 or 2, B represents:

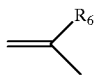

in which the double bond is linked to Y, $R_6$ represents substituted or unsubstituted aryl or the like; when Y is N, m stands for 0 or 1, n stands for 2 or 3 and B represents carbonyl, sulfonyl or the like, $E_1$ and $E_2$ individually represent H or lower alkyl; and D represents an aromatic hydrocarbon group or an aromatic heterocyclic group; and salts thereof.

The benzothiazine derivatives (I) and their salts according to the present invention have strong serotonin-2 blocking action, have excellent selectivity to this action against $\alpha_1$ blocking action and have high safety. Accordingly, the present invention has made it possible to provide pharmaceuticals making use of antagonistic action against serotonin-2 receptors, for example, therapeutics for various circulatory diseases such as ishemic heart diseases, cerebrovascular disturbances and peripheral circulatory disturbances.

14 Claims, No Drawings

BENZOTHIAZINE DERIVATIVE

RELATED U.S. APPLICATION

This application is a Division of application Ser. No. 08/669,615 Filed on Jun, 24, 1996, allowed, which is Continuation-in-Part of application Ser. No. 08/507,239, filed Aug. 24, 1995, now abandoned and a continuation of PCT/JP941 02194 filed Dec. 22, 1994.

BACKGROUND OF THE INVENTION a) Field of the Invention

This invention relates to novel benzothiazine derivatives. More specifically, this invention is concerned with benzothiazine derivatives and salts thereof, said derivatives and salts being useful for the prevention or treatment of ischemic heart diseases such as angina pectoris, arrhythmia, myocardial infarction, congestive heart, failure and post-PTCA restenosis, cerebrovascular disturbances such as cerebral infarction and cerebral sequelae after subarachnoid hemorrhage, and/or peripheral circulatory disturbances such as arteriosclerosis obliterans, Raynaud disease, Buerger disease and thrombophlebitis; their preparation process; and pharmaceuticals comprising them as effective ingredients.

b) Description of the Related Art

Serotonin is a compound contained abundantly in platelets, which are a blood component, and in a central nervous system, it acts as a neurotransmitter. In platelets, it is released upon stimulation by thromboxane $A_2$, ADP, collagen or the like and synergistically acts on various platelet aggregation factors or vasoconstrictors through activation of serotonin-2 receptors in the platelets and vascular smooth muscle cells, thereby inducing strong platelet aggregation and vasoconstriction [P. M. Vanhoutte, "Journal of Cardiovascular Pharmacology", Vol. 17 (Supple. 5), S6–S12 (1991)].

Serotonin is also known to potentiate proliferation of vascular smooth muscle cells [S. Araki et al., "Atherosclerosis", Vol. 83, p29–p34(1990)]. It has been considered that, particularly when endothelial cells are injured as in arteriosclerosis or myocardial infarction, the vasoconstricting action and thrombus forming action of serotonin are exasperated, thereby reducing or even stopping blood supply to myocardial, cerebral and peripheral organs [P. Golino et al., "The New England Journal of Medicine", Vol. 324, No. 10, p641–p648(1991), Y. Takiguchi et al., "Thrombosis and Haemostasis", Vol. 68(4), p460–p463 (1992), A. S. Weyrich et al., "American Journal of Physiology", Vol. 263, H349–H358(1992)].

Being attracted by such actions of serotonin or serotonin-2 receptors, various attempts are now under way to use a serotonin-2 receptor antagonist as a pharmaceutical for ischemic diseases of the heart, the brain and peripheral tissues.

Ketanserin which has therapeutically been used as a hypotensive drug is known as a compound having antagonistic action against a serotonin-2 receptor. Ketanserin has strong antagonistic action against a sympathetic nerve $\alpha_1$ receptor and also against histamine-1 and dopamine receptors in addition to antagonistic action against serotonin-2 receptors so that there is the potential problem of developing excessive hypotensive action, neuroleptic action or the like when used for the treatment of ischemic heart disease or peripheral circulatory disturbance. Ketanserin is therefore not preferred.

In addition, several compounds led by sarpogrelate are known to have serotonin-2 receptor antagonistic action. They, however, are accompanied with problems in the potency, the selectivity against other receptors, toxicity, side effects or the like. Thus, there remains still much room for improvements.

SUMMARY OF THE INVENTION

In view of the foregoing circumstances, the present inventors synthesized numerous compounds and investigated their pharmacological effects. As a result, it has been found that specific benzothiazine derivatives have strong serotonin-2 receptor antagonistic action, is excellent in the selectivity of a serotonin-2 receptor in the antagonistic action against various receptors, particularly in the selectivity to a serotonin-2 receptor in the antagonistic action against $\alpha_1$ receptor, and have low toxicity, leading to the completion of the present invention.

The present invention has been completed based on the above described findings and a first object of the present invention is to provide a benzothiazine derivative represented by the following formula (I):

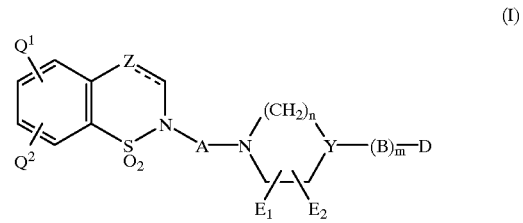

wherein the dashed line indicates the presence or absence of a bond and when the bond indicated by the dashed line is present, Z represents one of the following groups:

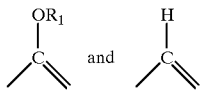

in which $R_1$ represents a substituted or unsubstituted alkyl group or a substituted or unsubstituted aralkyl group but, when the bond indicated by the dashed line is absent, Z represents one of the following groups:

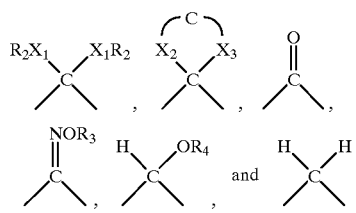

wherein $R_2$ represents a substituted or unsubstituted alkyl group, a substituted or unsubstituted aryl group or a substituted or unsubstituted aralkyl group, $R_3$ represents a hydrogen atom, a substituted or unsubstituted alkyl group, a substituted or unsubstituted aryl group or a substituted or unsubstituted aralkyl group, $R_4$ represents a hydrogen atom, a substituted or unsubstituted alkyl group or a substituted or unsubstituted aralkyl group, $X_1$, $X_2$ and $X_3$ each independently represents an oxygen atom or a sulfur atom, G represents an ethylene group with one or more of the hydrogen atoms thereof optionally substituted by a like number of halogen atoms and/or alkyl, aryl, aralkyl and/or alkylidene groups or a trimethylene group with one or more of the hydrogen atoms thereof optionally substituted by a like number of halogen atoms and/or alkyl, aryl, aralkyl and/or alkylidene groups, $Q_1$ represents a hydrogen atom, a hydroxyl group, a halogen atom, a substituted or unsubstituted alkyl group, a substituted or unsubstituted alkoxy group, a substituted or unsubstituted aralkyl group or a substituted or unsubstituted aralkyloxy group, $Q_2$ represents a hydrogen atom, a hydroxyl group, a halogen atom, a substituted or unsubstituted alkyl group, a substituted or unsubstituted alkoxy group, a substituted or unsubstituted aralkyl group or a substituted or unsubstituted aralkyloxy group, A represents a substituted or unsubstituted alkylene group, a substituted or unsubstituted alkenylene group or a substituted or unsubstituted alkynylene group;

Y represents CH, C= or a nitrogen atom; and, when Y represents CH, m stands for 0 or 1, n stands for 1 or 2, and B represents an oxygen atom, a sulfur atom, a carbonyl group, a sulfinyl group, a sulfonyl group, an alkylene group, an alkenylene group, a substituted or unsubstituted hydroxymethylene group, a group —$CHR_5$— in which $R_5$ represents a substituted or unsubstituted alkyl group, a substituted or unsubstituted aryl group or a substituted or unsubstituted aralkyl group, or a substituted or unsubstituted cyclic or acyclic acetal group, when Y represents C=, m stands for 1, n stands for 1 or 2, and B represents:

in which the double bond is linked to Y, $R_6$ represents a substituted or unsubstituted alkyl group, a substituted or unsubstituted aryl group or a substituted or unsubstituted aralkyl group, but, when Y represents a nitrogen atom, m stands for 0 or 1, n stands for 2 or 3, and B represents a carbonyl group, a sulfonyl group, an alkylene group, an alkenylene group or a group —$CHR_7$— in which $R_7$ represents a substituted or unsubstituted alkyl group, a substituted or unsubstituted aryl group or a substituted or unsubstituted aralkyl group, $E_1$ and $E_2$ each independently represents a hydrogen atom or a lower alkyl group, and D represents a substituted or unsubstituted aromatic hydrocarbon group or a substituted or unsubstituted aromatic heterocyclic group; or a salt thereof.

Another object of the present invention is to provide a preparation process of the benzothiazine derivative (I) or its salt.

A further object of the present invention is to provide a pharmaceutical such as a therapeutic for circulatory diseases or the like, said pharmaceutical containing the benzothiazine derivative (I) or its pharmacologically-acceptable salt thereof as an effective ingredient.

The benzothiazine derivatives (I) and their salts according to the present invention have strong serotonin-2 blocking action, have excellent selectivity to $\alpha_1$ blocking action and have high safety. Accordingly, the present invention has made it possible to provide pharmaceuticals making use of antagonistic action against serotonin-2 receptors, for example, therapeutics for various circulatory diseases such as ishemic heart diseases, cerebrovascular disturbance and peripheral circulatory disturbance.

DETAILED DESCRIPTION OF THE INVENTION AND PREFERRED EMBODIMENTS

In the benzothiazine derivatives (I) of the present invention, preferred examples of group $R_1$ include branched or linear $C_{1-4}$ alkyl groups such as methyl and ethyl and $C_{7-22}$ aralkyl groups such as benzyl and phenethyl, each of which may be substituted by one or more of halogen atoms such as fluorine, chlorine and bromine; alkyl groups, preferably $C_{1-4}$ alkyl groups such as methyl and ethyl; and/or alkoxy groups, preferably $C_{1-4}$ alkoxy groups such as methoxy and ethoxy.

Preferred examples of group $R_2$ include branched or linear $C_{1-4}$ alkyl groups such as methyl and ethyl, $C_{6-14}$ aryl groups such as phenyl and naphtyl and $C_{7-22}$ aralkyl groups such as benzyl and phenethyl, each of which may be substituted by one or more of halogen atoms such as fluorine, chlorine and bromine; alkyl groups, preferably $C_{1-4}$ alkyl groups such as methyl and ethyl; and/or alkoxy groups, preferably $C_{1-4}$ alkoxy groups such as methoxy and ethoxy. In this case, preferred examples of group $R_2X_1$— include methoxy, methylthio, ethoxy and ethylthio groups.

Preferred examples of the following group:

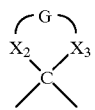

includes groups represented by the following formulas:

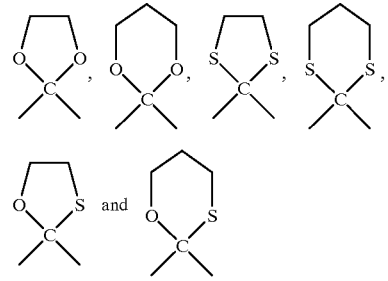

in which one or more of the hydrogen atoms may be substituted by a corresponding number of halogen atoms such as fluorine, chlorine and bromine; alkyl groups, preferably $C_{1-4}$ alkyl groups such as methyl and ethyl; aryl groups, preferably $C_{6-14}$ aryl groups such as phenyl and naphtyl; aralkyl groups, preferably $C_{7-22}$ aralkyl groups such as benzyl and phenethyl; and/or alkylidene groups, preferably $C_{1-4}$ alkylidene groups such as methylidene and ethylidene.

Preferred examples of group $R_3$ of group $NOR_3$ include a hydrogen atom, branched or linear $C_{1-4}$ alkyl groups such as methyl and ethyl, $C_{6-14}$ aryl groups such as phenyl and naphtyl and $C_{7-22}$ aralkyl groups such as benzyl and phenethyl. Each of the exemplified groups may be substituted by one or more of halogen atoms such as fluorine, chlorine and bromine; alkyl groups, preferably $C_{1-4}$ alkyl groups such as methyl and ethyl; and/or alkoxy groups, preferably $C_{1-4}$ alkoxy groups such as methoxy and ethoxy.

Preferred examples of group $R_4$ include a hydrogen atom, branched or linear $C_{1-4}$ alkyl groups such as methyl and ethyl and $C_{7-22}$ aralkyl groups such as benzyl and phenethyl. Each of the exemplified groups may be substituted by one or more of halogen atoms such as fluorine, chlorine and bromine; alkyl groups, preferably $C_{1-4}$ alkyl groups such as methyl and ethyl; and/or alkoxy groups, preferably $C_{1-4}$ alkoxy groups such as methoxy and ethoxy.

Preferred examples of group Z include the following group:

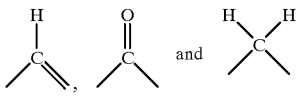

Specifically preferred examples of the group Z include the following groups:

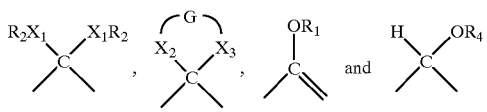

wherein G, $R_1$, $R_2$, $R_4$, $X_1$, $X_2$ and $X_3$ have the same meanings as defined above.

Preferred examples of $Q_1$ include a hydrogen atom; a hydroxyl group; halogen atoms such as fluorine, chlorine and bromine; branched or linear $C_{1-4}$ alkyl groups such as methyl and ethyl; branched or linear $C_{1-4}$ alkoxy groups such as methoxy and ethoxy; $C_{7-22}$ aralkyl groups such as benzyl and phenethyl; and $C_{7-22}$ aralkyloxy groups such as benzyloxy and phenethyloxy. Each of the exemplified groups may be substituted by one or more of halogen atoms such as fluorine, chlorine and bromine; alkyl groups, preferably $C_{1-4}$ alkyl groups such as methyl and ethyl; and/or alkoxy groups, preferably $C_{1-4}$ alkoxy groups such as methoxy and ethoxy. Of these $Q_1$, particularly preferred include a hydrogen atom, a methoxy group, a chlorine atom and the like.

Preferred examples of $Q_2$ include a hydrogen atom; a hydroxyl group; halogen atoms such as fluorine, chlorine and bromine; branched or linear $C_{1-4}$ alkyl groups such as methyl and ethyl; branched or linear $C_{1-4}$ alkoxy groups such as methoxy and ethoxy; $C_{7-22}$ aralkyl groups such as benzyl and phenethyl; and $C_{7-22}$ aralkyloxy groups such as benzyloxy and phenethyloxy. Each of the exemplified groups may be substituted by one or more of halogen atoms such as fluorine, chlorine and bromine; alkyl groups, preferably $C_{1-4}$ alkyl groups such as methyl and ethyl; and/or alkoxy groups, preferably $C_{1-4}$ alkoxy groups such as methoxy and ethoxy. Of these $Q_2$, particularly preferred include a hydrogen atom, a methoxy group, a chlorine atom and the like.

Further, preferred examples of substituting positions and combinations of $Q_1$ and $Q_2$ include combinations of a hydrogen atom as $Q_1$ and 5-hydroxy, 5-chloro, 5-bromo, 5-methyl, 5-ethyl, 5-n-propyl, 5-isopropyl, 5-n-butyl, 5-s-butyl, 5-methoxy, 5-ethoxy, 5-n-propoxy, 5-isopropoxy, 5-benzyloxy, 6-hydroxy, 6-fluoro, 6-chloro, 6-methyl, 6-ethyl, 6-n-propyl, 6-methoxy, 6-ethoxy, 6-n-propoxy, 6-benzyloxy, 7-hydroxy, 7-fluoro, 7-chloro, 7-methyl, 7-ethyl, 7-n-propyl, 7-methoxy, 7-ethoxy, 7-n-propoxy, 7-benzyloxy, 8-hydroxy, 8-fluoro, 8-chloro, 8-methyl, 8-ethyl, 8-n-propyl, 8-methoxy, 8-ethoxy, 8-n-propoxy and 8-benzyloxy as $Q_2$; and also combinations of 5,7-dihydroxy, 6,7-dichloro, 5,8-dimethyl, 6,8-dimethyl, 5,6-dimethoxy, 5,7-dimethoxy, 5,8-dimethoxy and 6,7-dimethoxy as $Q_1$ and $Q_2$.

Preferred examples of group A include branched or linear $C_{2-10}$ alkylene groups such as ethylene, trimethylene, tetramethylene, pentamethylene and octamethylene, branched or linear $C_{4-10}$ alkenylene groups such as 2-butenylene and 3-pentenylene groups; and branched or linear $C_{4-10}$ alkynylene groups such as 2-butynylene and 3-pentynylene groups. Each of the exemplified group may be substituted by one or more of halogen atoms such as fluorine, chlorine and bromine. Among them, ethylene, trimethylene and tetramethylene groups are particularly preferred.

The group, which is represented by the following formula:

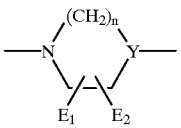

wherein $E_1$, $E_2$, Y and n have the same meanings as defined above, is a heterocyclic group led by a pyrrolidine, piperidine, piperazine or homopiperazine group, in which two or less hydrogen atoms on the ring may be substituted by lower alkyl groups, preferably $C_{1-4}$ alkyl groups such as methyl or ethyl.

When the group of the above formula is a heterocylic group derived from pyrrolidine or piperidine, preferably a piperidine group, m stands for 0 or 1 with the proviso that m is 1 when Y represents C=, and B represents an oxygen atom, a sulfur atom, a carbonyl group, a sulfinyl group, a sulfonyl group, an alkylene group (preferably a $C_{1-4}$ alkylene group and most preferably a methylene group), an alkenylene group (preferably $C_{2-5}$ alkenylene group and most preferably a 2-propenylene group), a substituted or unsubstituted hydroxymethylene group, a group —$CHR_5$— (in which $R_5$ preferably represents a $C_{1-4}$ alkyl group such as methyl and ethyl; a $C_{6-14}$ aryl group such as phenyl or naphthyl; or a $C_{7-22}$ aralkyl group such as benzyl or phenethyl, which may be substituted), the following group:

wherein the double bond is linked to Y, and $R_6$ represents an alkyl group, preferably a $C_{1-4}$ alkyl group such as methyl and ethyl; an aryl group, preferably $C_{6-14}$ aryl group such as phenyl and naphtyl; and an aralkyl group, preferably a $C_{7-22}$ aralkyl group such as benzyl and phenethyl, which may be substituted), cyclic acetal or acyclic acetal group in which one or more of hydrogen atoms may be substituted.

Exemplary cyclic or acylic acetal groups include the following groups:

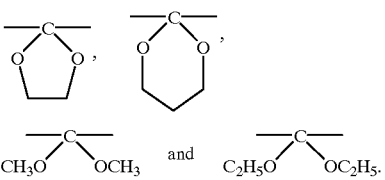

Preferred examples of a substituent group for the hydroxylmethylene group represented by B include alkyl groups, preferably $C_{1-4}$ alkyl groups such as methyl and ethyl and aryl groups, preferably $C_{6-14}$ aryl groups such as phenyl and naphthyl, all substituted to the carbon atom of the methylene group. Further, they can be substituted by one or more of hydroxyl groups, halogen atoms such as fluorine, chlorine and bromine and/or alkoxy groups, preferably $C_{1-4}$ alkoxy groups such as methoxy and ethoxy.

Particularly preferred examples of the substituted or unsubstituted hydroxymethylene group include an unsubstituted hydroxymethylene group and hydroxymethylene groups substituted by a phenyl, fluorophenyl or hydroxyphenyl group.

Further, examples of one or more substituent groups for $R_5$ include one or more halogen atoms such as fluorine, chlorine and bromine; alkyl groups, preferably $C_{1-4}$ alkyl groups such as methyl and ethyl; and alkoxy groups, preferably $C_{1-4}$ alkoxy groups such as methoxy and ethoxy.

Illustrative of one or more substituent groups for $R_6$ include one or more halogen atoms such as fluorine, chlorine and bromine; alkyl groups, preferably $C_{1-4}$ alkyl groups such as methyl and ethyl; alkoxy groups, preferably $C_{1-4}$ alkoxy groups such as methoxy and ethoxy; and hydroxyl groups. Examples of one or more substituent groups for the cyclic or acyclic acetal include halogen atoms such as fluorine, chlorine and bromine; alkyl groups, preferably $C_{1-4}$ alkyl groups such as methyl and ethyl; aryl groups, preferably $C_{6-14}$ aryl groups such as phenyl and naphthyl; aralkyl groups, preferably $C_{7-22}$ aralkyl groups such as benzyl and phenethyl; and alkylidene groups, preferably $C_{1-4}$ alkylidene groups such as methylidene and ethylidene.

Among these illustrative examples of the group represented by B, especially preferred is a carbonyl group.

When the heterocyclic group is a group derived from piperazine or homopiperazine, preferably a piperazine group, m stands for 0 or 1 (preferably 0) and B represents a carbonyl group, a sulfonyl group, an alkylene group (preferably a $C_{1-4}$ alkylene group, particularly a methylene group), an alkenylene group (preferably $C_{3-6}$ alkenylene group, particularly 2-propenylene group) or a group —CHR$_7$— (in which R$_7$ represents an alkyl group, preferably a $C_{1-4}$ alkyl group such as methyl and ethyl; an aryl group, preferably $C_{6-14}$ aryl group such as phenyl and naphthyl; and an aralkyl group, preferably a $C_{7-22}$ aralkyl group such as benzyl and phenethyl).

R$_7$ may in turn be substituted by one or more halogen atoms such as fluorine, chlorine and bromine; alkyl groups, preferably $C_{1-4}$ alkyl groups such as methyl and ethyl; and/or alkoxy groups, preferably $C_{1-4}$ alkoxy groups such as methoxy and ethoxy.

Of the above-described examples of group B, preferred is a substituted or unsubstituted phenylmethylene group.

Preferred examples of group D include aromatic hydrocarbon groups, preferably $C_{6-28}$ aromatic hydrocarbon groups such as a phenyl group with one or more of its hydrogen atoms having been optionally substituted and a naphtyl group with one or more of its hydrogen atoms having been optionally substituted. Other preferred examples of group D include aromatic heterocyclic groups, preferably monocyclic or bicyclic ones with three or fewer oxygen, sulfur and/or nitrogen atoms—such as pyridyl, pyrimidinyl, benzisothiazolyl, benzisoxazolyl and indolyl groups with one or more hydrogen atoms thereof having been optionally substituted.

Examples of substituent groups for the aromatic hydrocarbon groups and aromatic heterocyclic groups include halogen atoms such as fluorine, chlorine and bromine; alkyl groups, preferably $C_{1-4}$ alkyl groups such as methyl and ethyl; alkoxy groups, preferably $C_{1-4}$ alkoxy groups such as methoxy and ethoxy; aryl groups, preferably $C_{6-14}$ aryl groups such as phenyl and naphthyl; aralkyl groups, preferably $C_{7-22}$ aralkyl groups such as benzyl and phenethyl; aralkyloxy groups, preferably $C_{7-22}$ aralkyloxy groups such as benzyloxy; cyano group; nitro group; carboxyl group; alkoxycarbonyl group (the number of carbons in the alcohol moiety preferably ranges from 1 to 6); lower alkylsulfonylamino groups (the number of carbon atoms in the alkyl moiety preferably ranges from 1 to 4); a carbamoyl group; and a hydroxyl group.

Of these illustrative groups represented by D, preferred are phenyl groups unsubstituted or substituted by one or more of halogen atoms, alkoxy groups and hydroxyl groups, benzisothiazolyl groups unsubstituted or substituted by one or more halogen atoms, benzisoxazolyl groups unsubstituted or substituted by one or more halogen atoms, and indazolyl groups unsubstituted or substituted by one or more halogen atoms. Particularly preferred are phenyl groups unsubstituted or substituted by one or more of fluorine atoms, methoxy groups and hydroxyl groups.

Many of the compounds (I) according to the present invention have isomers. It is to be noted that these isomers and mixtures thereof are all embraced by the present invention.

Various processes can be employed for the preparation of the benzothiazine derivatives (I) according to the present invention. It is however preferred to prepare the benzothiazine derivatives, for example, by any one of the following processes.

Process 1

Among the benzothiazine derivatives (I), each of compounds (Ib) in which Z is represented by one of the following formulas:

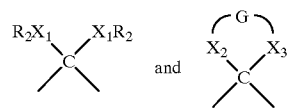

can be synthesized in accordance with any of the processes shown by the following schemes.

(a) The compound (Ib) can be obtained, in accordance with the following reaction scheme, by reacting a compound represented by the formula (XXV) with a compound represented by the formula (III) to be converted to a compound represented by the formula (XXVI) and then reacting a nitrogen-containing compound represented by the formula (V) or a salt thereof with the compound (XXVI).

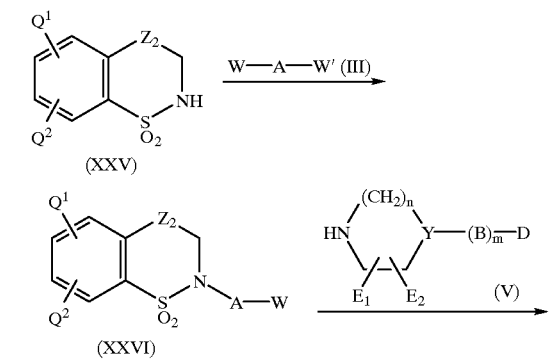

-continued

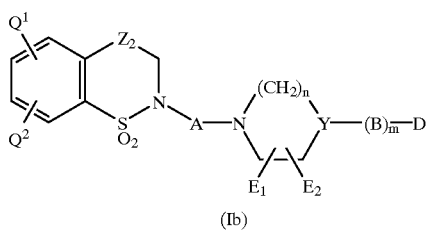

wherein A, B, D, $E_1$, $E_2$, $Q_1$, $Q_2$, Y, m and n have the same meanings as defined above, $Z_2$ represents one of the following groups:

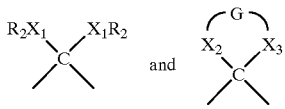

wherein G, $R_2$, $X_1$, $X_2$ and $X_3$ have the same meanings as defined above, and W and W' may be the same or different and individually represent a substituent easily replaceable with an amino group.

In the above reactions, the conversion from the compound (XXV) to the compound (XXVI) can be effected by causing the compound (III) to act on the compound (XXV) after treating the compound (XXV) with an inorganic base or an organic base, or by causing the compound (III) to act on the compound (XXV) in the presence of such a base.

Examples of group W or W' of the compound (III), which is an eliminative substituent and is easily replaceable with an amino group, include halogen atoms such as chlorine and bromine, alkylsulfonyloxy groups such as methanesulfonyloxy and arylsulfonyloxy groups such as p-toluenesulfonyloxy.

On the other hand, exemplary inorganic or organic bases include sodium hydride, potassium hydride, sodium carbonate, potassium carbonate, triethylamine and potassium t-butoxide. Further, illustrative solvents useful for the above reaction include tetrahydrofuran, dioxane, dimethylformamide, dimethylsulfoxide, acetonitrile, N-methylpyrrolidone, acetone, 2-butanone and toluene. The reaction is conducted at −78° C. to reflux temperature.

To prepare the compound (Ib) by reacting the thus-obtained compound (XXV) with the nitrogen-containing compound (V), it is only necessary to react the nitrogen-containing compound (V) or an organic acid salt or inorganic acid salt thereof with the compound (XXV), optionally together with an organic base such as triethylamine, pyridine, collidine, 1,8-diazabicyclo-[5.4.0]undec-7-en (DBU) or potassium t-butoxide or an inorganic base such as potassium carbonate, sodium carbonate, sodium hydrogencarbonate, sodium hydroxide or sodium hydride, optionally after adding an alkali iodide such as potassium iodide or sodium iodide, at 0° C. to 150° C. in the solvent exemplified above or a solvent such as methanol, ethanol, propanol or butanol.

Examples of the nitrogen-containing compound (V) include 1-phenylpiperazine, 1-(2-fluorophenyl)piperazine, 1-(3-fluorophenyl)piperazine, 1-(4-fluorophenyl)piperazine, 1-(4-hydroxyphenyl)piperazine, 1-(2-chlorophenyl) piperazine, 1-(3-chlorophenyl)piperazine, 1-(4-chlorophenyl)piperazine, 1-(2-methoxyphenyl)piperazine, 1-(3-methoxyphenyl)piperazine, 1-(4-methoxyphenyl) piperazine, 1-(4-methanesulfonamidophenyl)piperazine, 1-(4-cyanophenyl)piperazine, 1-(4-carbamoylphenyl) piperazine, 1-(4-methoxycarbonylphenyl)piperazine, 1-(2-pyridyl)piperazine, 1-(2-pyrimidinyl)piperazine, 1-benzylpiperazine, 1-diphenylmethylpiperazine, 1-cinnamylpiperazine, 1-benzoylpiperazine, 1-(4-benzyloxybenzoyl)piperazine, 1-(4-hydroxybenzoyl) piperazine, 1-(2-furoyl)piperazine, 1-(1,2-benzisooxazol-3-yl)piperazine, 1-(1,2-benzisothiazol-3-yl)piperazine, 4-phenylpiperidine, 4-benzylpiperidine, α,α-bis(4-fluorophenyl)-4-piperidinemethanol, 4-(4-fluorobenzoyl) piperidine, 4-benzoylpiperidine, 4-(4-methoxybenzoyl) piperidine, 4-(4-chlorobenzoyl)piperidine, 3-(4-fluorobenzoyl)piperidine, 4-(6-fluoro-1,2-benzisoxazol-3-yl)piperidine, 4-(6-fluoro-1,2-benzisothiazol-3-yl) piperidine, 4-(6-fluoro-1H-indazol-3-yl)piperidine, 3-benzoylpyrrolidine, 3-(4-fluorobenzoyl)pyrrolidine, 4-(4-fluorophenoxy)piperidine, 4-[(4-fluorophenyl)thio] piperidine, 4-[(4-fluorophenyl)sulfinyl]piperidine, 4-[(4-fluorophenyl)sulfonyl]-piperidine, 4-[bis(4-fluorophenyl) methylene]piperidine and 4-(4-fluorobenzoyl)piperidine ethylene acetal. They are all either known compounds or compounds which can be readily prepared by a known process or a process similar to the known process.

In the above reactions, the compound (XXV) employed as the starting material can be prepared using as a raw material a saccharin derivative represented by the formula (XXVII) in accordance with the following reaction scheme:

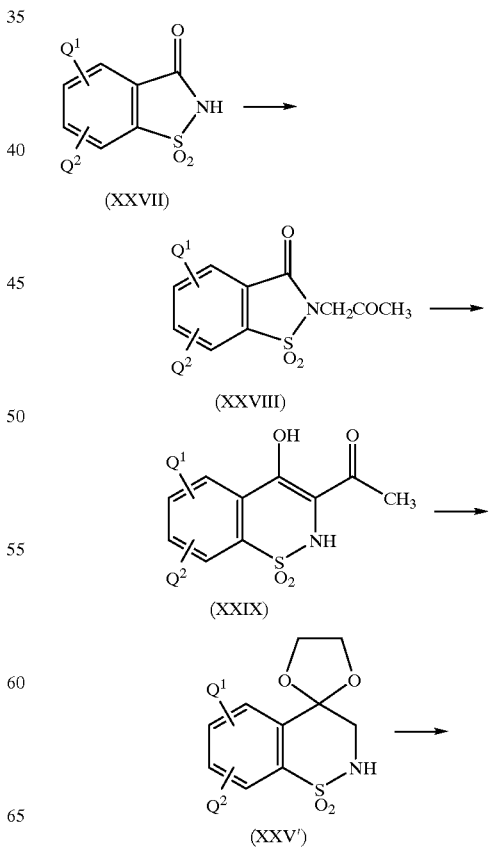

-continued

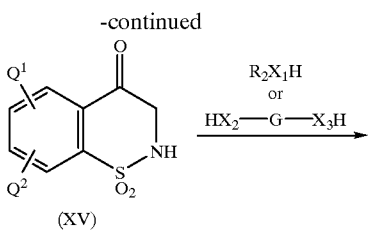

(XV)

wherein G, $R_2$, $Q_1$, $Q_2$, $X_1$, $X_2$, $X_3$ and $Z_2$ have the same meanings as defined above.

Saccharins (XXVII) usable as starting materials in the above reactions are either known compounds or compounds which can be readily prepared by a known process or by referring to known literature. For example, preparation processes for saccharins substituted by one or more hydroxyl groups are disclosed in Japanese Patent Application Laid-Open (Kokai) No. SHO 56-166181, Japanese Patent Application Laid-Open (Kokai) No. SHO 61-215382, etc., while preparation processes for saccharins substituted by one or more halogen atoms such as fluorine, chlorine and bromine atoms were proposed, for example, by W. Davies in J. Chem. Soc., 119(I), 876 (1921), by F. Becke et al. in Liebigs Ann. Chem., 729, 146 (1969), by J. G. Lombardino in J. Org., Chem., 36, 1843 (1971) and by Nitta et al. in Yakugaku Zasshi, 84, 496 (1964) and are also disclosed in Japanese Patent Application Laid-Open (Kokai) No. SHO 52-71464, Japanese Patent Application Laid-Open (Kokai) No. SHO 56-166181, Japanese Patent Application Laid-Open (Kokai) No. HEI 5-194444, etc.

Further, preparation processes for saccharins substituted by one or more alkyl groups such as methyl groups were proposed by J. G. Lombardino in J. Org. Chem., 36, 1843 (1971) and are disclosed in Japanese Patent Application Laid-Open (Kokai) No. SHO 52-71464, Japanese Patent Application Laid-Open (Kokai) No. SHO 61-215382, Japanese Patent Application Laid-Open (Kokai) No. HEI 5-194444, etc., and preparation processes for saccharins substituted by one or more alkoxy groups such as methoxy groups were proposed by J. G. Lombardino in J. Org. Chem., 36, 1843 (1971) and are disclosed in Japanese Patent Application Laid-Open (Kokai) No. SHO 52-71464, Japanese Patent Application Laid-Open (Kokai) No. SHO 56-166181, Japanese Patent Application Laid-Open (Kokai) No. SHO 61-263961, Japanese Patent Application Laid-Open (Kokai) No. HEI 5-194444, etc.

Accordingly, saccharins (XXIII) containing desired substituent groups as $Q_1$ and $Q_2$ can be obtained by these processes or by processes derived with reference to such processes.

The conversion from the compound (XXVII) to the compound (XXV') can be conducted referring to literatures [E. Eckenroth et al., Ber., 29, 329 (1896); H. Zinnes et al., J. Org. Chem., 30, 2241 (1965); H. Zinnes et al., J. Org. Chem., 31, 162 (1966)].

On the other hand, the conversion from the compound (XXV') to the compound (XV) can be effected using various processes. As a typical example, an acid such as hydrochloric acid or acetic acid is caused to act on the compound (XXV').

Further, the conversion from the compound (XV) to the compound (XXV) can be conducted by choosing an appropriate process such as that described by T. W. Greene in Protective Groups in Organic Synthesis, John Wiley & Sons, Inc. As a typical example, $R_2X_1H$ or $HX_2$—G—$X_3H$ is caused to act on the compound (XV) in the presence of an acid.

In addition, the compound (XXVI) can also be synthesized from the compound (XXV') in accordance with the following reaction scheme.

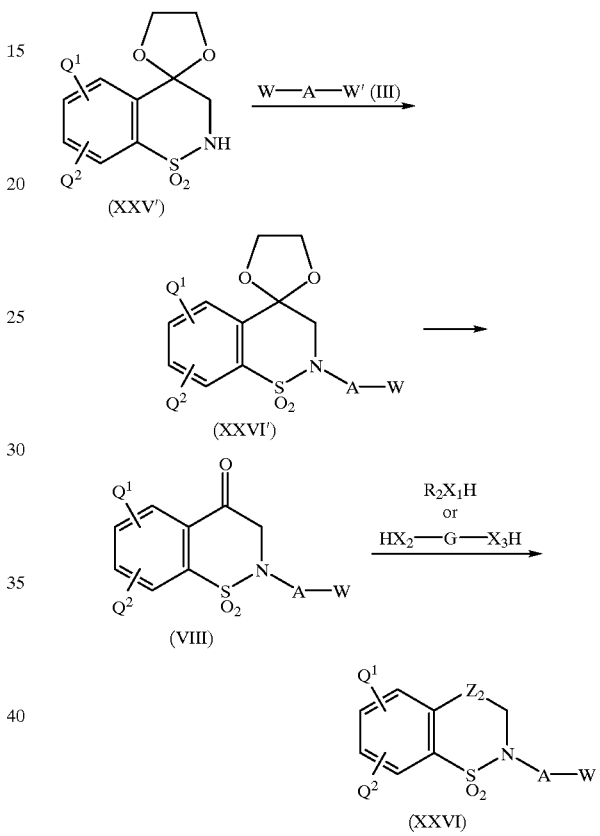

wherein A, G, $Q_1$, $Q_2$, $R_2$, W, W', $X_1$, $X_2$, $X_3$ and $Z_2$ have the same meanings as defined above.

The conversion from the compound (XXV') to the compound (XXVI') can be practiced under similar conditions as the conversion from the compound (XXV) to the compound (XXVI). Further, the conversion from the compound (XXVI') to the compound (VIII) can be practiced under similar conditions as the conversion from the compound (XXV') to the compound (XV). Moreover, the conversion from the compound (VIII) to the compound (XXVI) can be practiced under similar conditions as the conversion from the compound (XV) to the compound (XXV).

(b) The target compound can be obtained by causing a nitrogen-containing compound represented by the formula (VI) or a salt thereof to act on the compound represented by the formula (XXV) in accordance with the following reaction scheme:

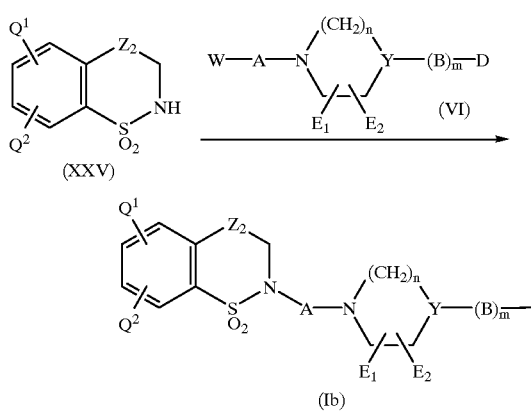

(Ib)

wherein A, B, D, $E_1$, $E_2$, $Q_1$ $Q_2$, W, Y, $Z_2$, m and n have the same meanings as defined above.

The conversion from the compound (XXV) to the compound (Ib) can be conducted by causing the compound (VI) to act on the compound (XXV) after treatment of the latter compound with an inorganic base or an organic base or in the presence of such a base. Reaction conditions are similar to those employed in the conversion from the compound (XXV) to the compound (XXVI) in Process 1(a). In this case, it is also possible to add an alkali iodide such as potassium iodide or sodium iodide as needed. Incidentally, the compound (VI) can be synthesized by reacting the compound (V) with the compound (III) in a manner known per se in the art.

Process 2

Among the benzothiazine derivatives (I), each of compounds (Ic) in which Z is represented by the following formula:

can be synthesized in any one of the following processes.

(a) The target compound can be obtained, in accordance with the following reaction scheme, by converting a compound (XV) or (XXVI) to a compound (VIII) and then reacting the compound (VIII) with a compound represented by the formula (V):

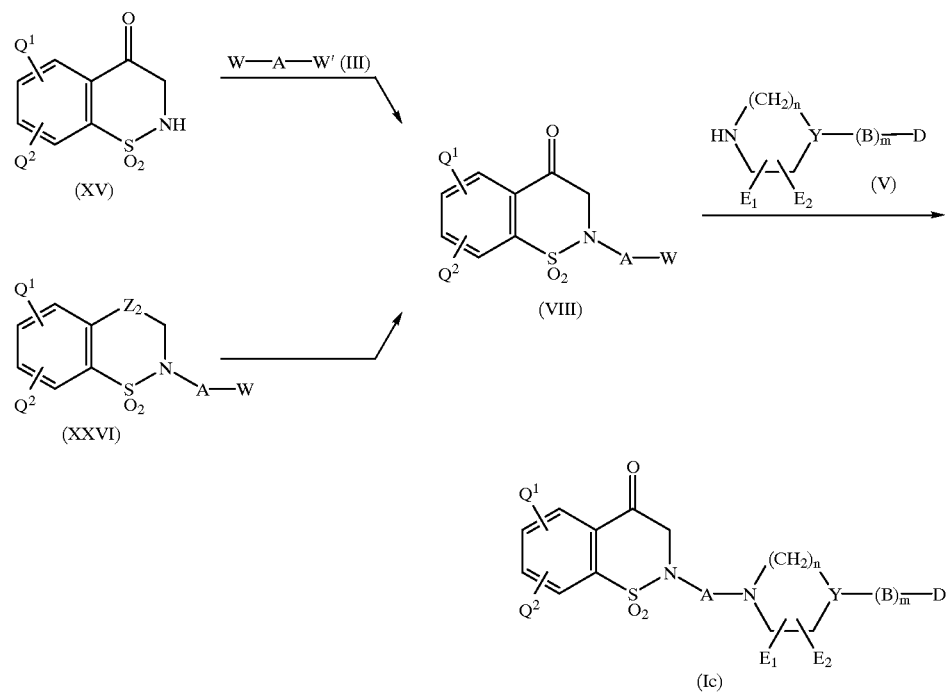

wherein A, B, D, $E_1$, $E_2$, $Q_1$, $Q_2$, W, W', Y, $Z_2$, m and n have the same meanings as defined above.

The conversion from the compound (XV) to the compound (VIII) can be effected under conditions similar to those employed upon conversion from the compound (XXV) to the compound (XXVI) shown in Process 1(a). Further, the conversion from the compound (XXVI) to the compound (VIII) can be effected employing the process described by T. W. Greene in "Protective Groups in Organic Synthesis", John Wiley & Sons, Inc. and the like. For instance, the conversion to the target compound (VIII) can be conducted by acid treatment of the compound (XXVI)

when in $Z_2$, $X_1$ represents an oxygen atom or $X_2$ and $X_3$ both represent an oxygen atom, or by the treatment with mercury (II) chloride when $X_1$ represents a sulfur atom or $X_2$ and $X_3$ both represent a sulfur atom.

The conversion from the compound (VIII) to the compound (Ic) can be effected under conditions similar to those employed upon conversion from the compound (XXVI) to the compound (Ib) shown in Process 1(a).

(b) The target compound can be obtained by the conversion of the group $Z_2$ of the compound (Ib) to a carbonyl group in accordance with the following reaction scheme.

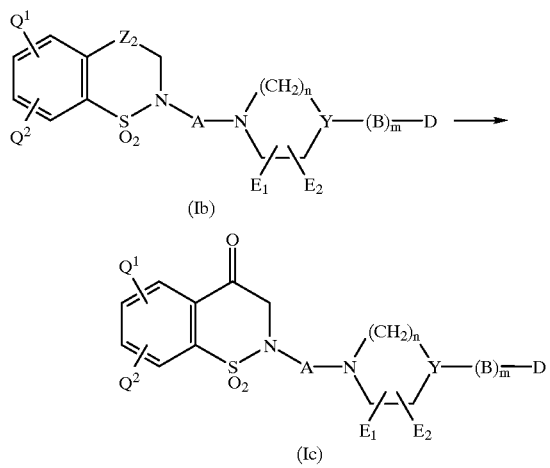

wherein A, B, D, $E_1$, $E_2$, $Q_1$, $Q_2$, Y, $Z_2$, m and n have the same meanings as defined above.

The conversion from the compound (Ib) to the compound (Ic) can be effected under conditions similar to those employed in the conversion from the compound (XXVI) to the compound (VIII) shown in Process 2(a).

Process 3

Among the benzothiazine derivatives (I), each of the compounds (Ig) and (Ie) in which Z is represented by the following formula:

can be synthesized in accordance with any one of the following processes. Selection of process (a) is desired where a nitrogen-containing compound (V) contains a group reactive to a hydroxylamine or a derivative thereof (VII) or a salt of the hydroxylamine or the derivative.

(a) Each compound (Ig) can be obtained, in accordance with the following reaction scheme, by causing a hydroxylamine or a derivative thereof represented by the formula (VII) or a salt of the hydroxylamine or the derivative thereof to act on the compound represented by the formula (VIII) and then causing the nitrogen-containing compound (V) to act further.

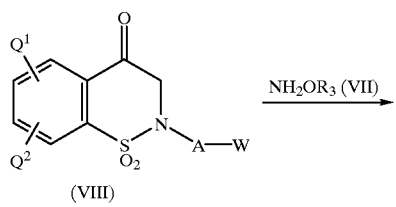

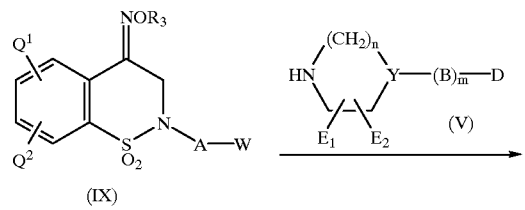

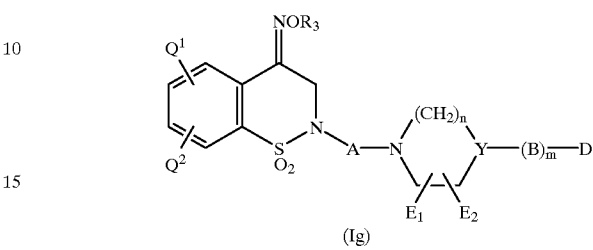

wherein A, B, D, $E_1$, $E_2$, $Q_1$, $Q_2$, $R_3$, W, Y, m and n have the same meanings as defined above.

The reaction between the compound (VIII) and the hydroxylamine or its derivative (VII) can be practiced, if necessary, in the presence of an organic base such as pyridine, triethylamine, collidine, DBU or sodium acetate or an inorganic base such as potassium carbonate or sodium hydroxide. The hydroxylamine or its derivative (VII) may also be used in the form of an organic acid salt or an inorganic acid salt.

The reaction is conducted at 0° C. to reflux temperature, preferably 0° C. to 100° C. optionally in a suitable solvent such as methanol, ethanol, propanol, tetrahydrofuran, dimethylformamide or dimethylsulfoxide.

The conversion from the thus-obtained compound (IX) to the compound (Ig) can be effected under conditions similar to those employed in the conversion from the compound (XXVI) to the compound (Ib) shown in Process 1(a).

(b) Each compound (Ie) can be obtained, in accordance with the following reaction scheme, by causing a hydroxylamine or a derivative thereof (VII) or a salt of the hydroxylamine or the derivative to act on the compound (Id):

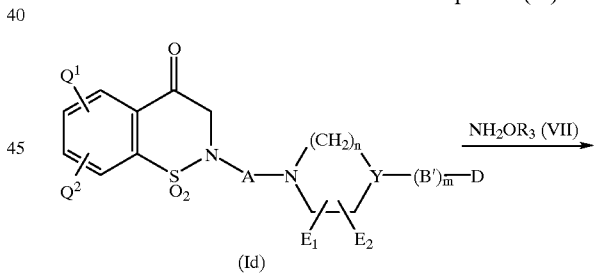

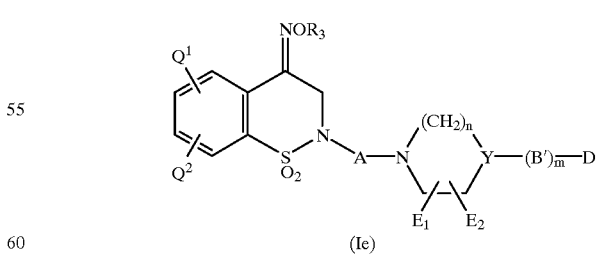

wherein, when Y represents CH, B' represents a oxygen atom, a sulfur atom, a sulfinyl group, a sulfonyl group, an alkylene group, an alkenylene group, a substituted or unsubstituted hydroxymethylene group, a group —$CHR_5$— in which $R_5$ represents a substituted or unsubstituted alkyl tuted or unsubstituted aralkyl group, or a substituted or unsubstituted cyclic or acyclic acetal group, when Y represents C=, B' represents the following group:

in which the double bond is linked to Y, $R_6$ represents a substituted or unsubstituted alkyl group, a substituted or unsubstituted aryl group or a substituted or unsubstituted aralkyl group, but, when Y represents a nitrogen atom, B' represents a carbonyl group, a sulfonyl group, an alkylene group, an alkenylene group or a group —$CHR_7$— in which $R_7$ represents a substituted or unsubstituted alkyl group, a substituted or unsubstituted aryl group or a substituted or unsubstituted aralkyl group, and A, D, $E_1$, $E_2$, $Q_1$, $Q_2$, $R_3$, Y, m and n have the same meanings as defined above.

The conversion from the compound (Id) to the compound (Ie) can be effected under conditions similar to those employed in the conversion from the compound (VIII) to the compound (IX) shown in Process 3(a).

Process 4

Among the benzothiazine derivatives (I), each of compounds (Ih) and (If) in which Z is represented by the following formula:

can be synthesized by any one of the following processes.

Incidentally, it is desired to select process (a) when there is a group reactive with a reducing agent in a nitrogen-containing compound (V).

(a) Each compound (Ih) can be obtained, in accordance with the following reaction scheme, by reducing the compound represented by the formula (VIII) to obtain the compound (X) and then causing the nitrogen-containing compound (V) to act on the resulting compound.

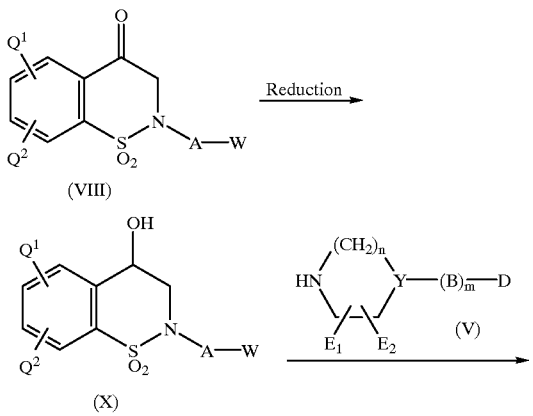

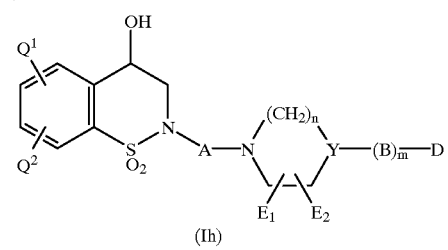

wherein A, B, D, $E_1$, $E_2$, $Q_1$, $Q_2$, W, Y, m and n have the same meanings as defined above.

The conversion from the compound (VIII) to the compound (X) can be effected by treating the compound represented by the formula (VIII) with a reducing agent such as sodium borohydride, potassium borohydride or sodium cyanoborohydride in a conventionally-employed solvent at −78° C. to reflux temperature, preferably −20° C. to room temperature.

Further, the conversion from the compound (X) to the compound (Ih) can be effected under conditions similar to those employed in the conversion from the compound (XXVI) to the compound (Ib) shown in Process 1(a).

(b) Each compound (If) can be obtained by reducing the compound (Id) in accordance with the following reaction scheme:

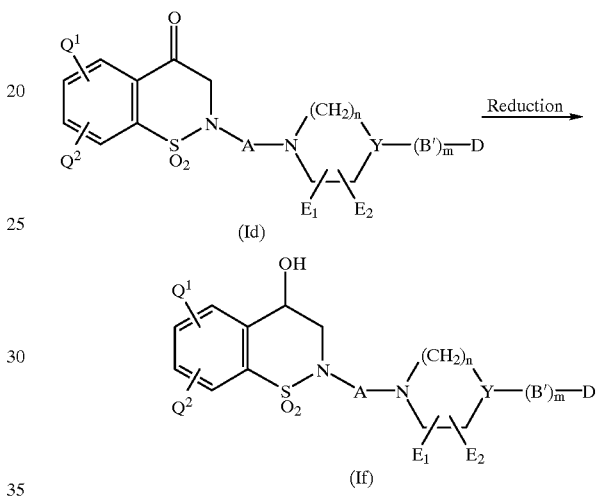

wherein A, B', D, $E_1$, $E_2$, $Q_1$, $Q_2$, Y, m and n have the same meanings as defined above.

The conversion from the compound (Id) to the compound (If) can be effected under conditions similar to those employed in the conversion from the compound (VIII) to the compound (X) shown in Process 4(a).

Process 5

Among the benzothiazine derivatives (I), each compound (II) in which Z is a group represented by the following formula:

can be synthesized in accordance with the process which will be described hereinafter:

The target compound can be obtained, in accordance with the following reaction scheme, by reacting a compound represented by the formula (XV) with a compound represented by the formula (XVI) to obtain a compound represented by the formula (XVII), reacting the resulting compound with a compound represented by the formula (III) to obtain a compound represented by the formula (XXX), and then causing a nitrogen-containing compound represented by the formula (V) to act on the compound (XXX).

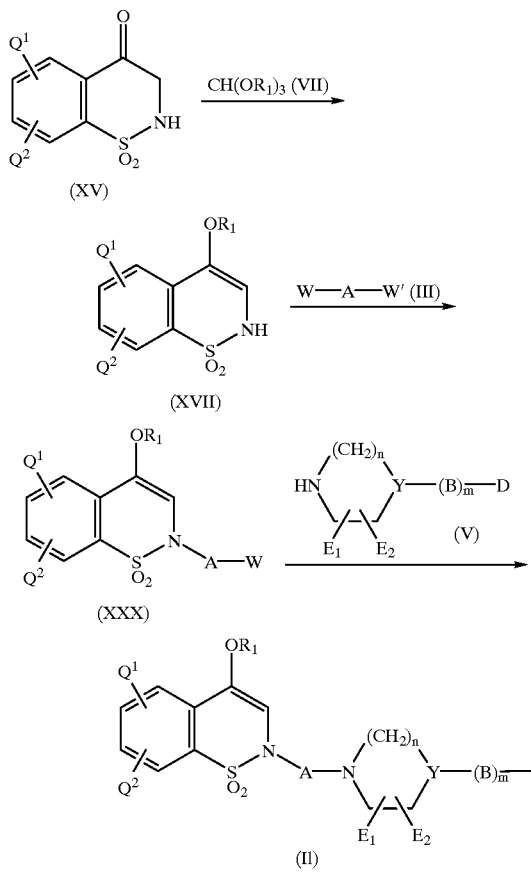

wherein A, B, D, $E_1$, $E_2$, $Q_1$, $Q_2$, $R_1$, W, W', Y, m and n have the same meanings as defined above.

In the above reaction, the conversion from the compound (XV) to the compound (XVII) can be effected by causing the compound (XVI) to act on the compound (XV) in the presence of p-toluenesulfonic acid, boron trifluoride ethyl ether complex, Amberlite 15 or the like.

Examples of the solvent usable in the above reaction may include methanol, ethanol, propanol and butanol. The reaction can be conducted at −78° C. to reflux temperature.

Further, the conversion from the compound (XVII) to the compound (Il) can be effected under conditions similar to those employed in the conversion from the compound (XXV) to the compound (Ib) shown in Process 1(a).

Process 6

Among the benzothiazine derivatives (I), each compound (Ii) in which Z is represented by the following formula:

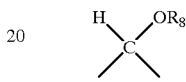

can be synthesized in accordance with the process which will be described hereinafter.

The compound represented by the formula (Ii) can be obtained, in accordance with the following reaction scheme, (1) by reducing a compound represented by the formula (XXXI) to a compound represented by the formula (XXXII) and reacting the resulting compound with the compound represented by the formula (III), or (2) by reacting a compound represented by the formula (XI) with a compound represented by the formula (X) to obtain a compound (XII), and then reacting the resulting compound with a nitrogen-containing compound represented by the formula (V). In this case, it is desired to select a suitable process from the processes (1) and (2) according to the kind of group $R_8$.

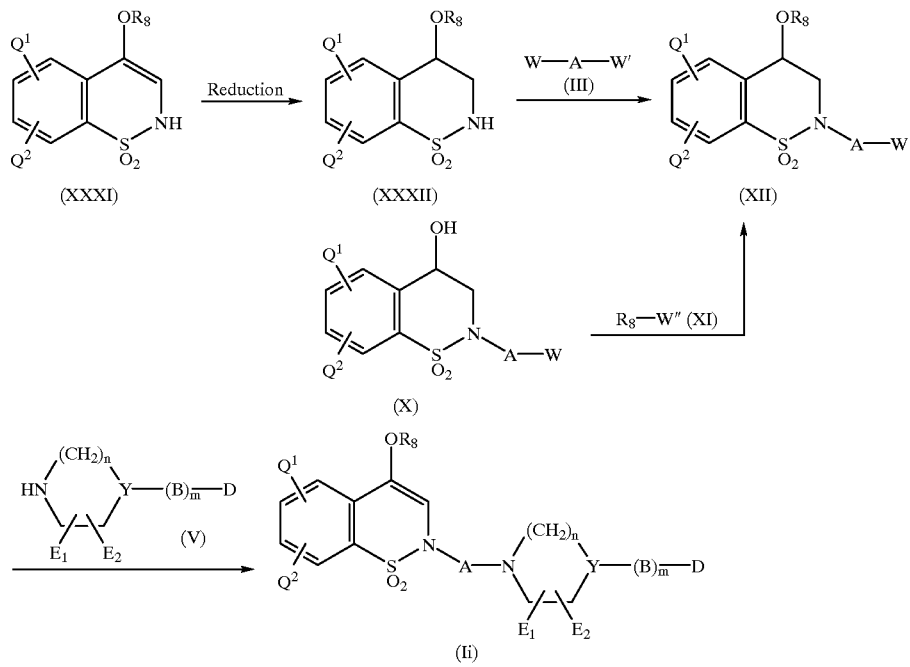

wherein A, B, D, $E_1$, $E_2$, $Q_1$, $Q_2$, $R_8$, W, W', W", Y, m and n have the same meanings as defined above.

In the above reaction, the conversion from the compound (XXXI) to the compound (XXXII) can be conducted by treating, in the presence of a catalyst such as palladium-carbon or platinum, the compound (XXXI) with hydrogen gas in a conventionally-employed solvent at −78° C. to reflux temperature, preferably at room temperature. The conversion from the compound (XXXII) to the compound (XII) can be effected under conditions similar to those employed in the conversion from the compound (XXV) to the compound (XXVI) shown in Process 1(a).

The conversion from the compound (X) to the compound (XII) can be conducted by causing the compound (XI) to act on the compound (X) either after treatment of the compound (X) with an inorganic base or organic base or in the presence of such a base.

The group W" in the compound (XI) is an eliminative substituent, and its examples include halogen atoms such as chlorine and bromine, alkylsulfonyloxy groups such as methanesulfonyloxy and arylsulfonyloxy groups such as p-toluenesulfonyloxy.

Further, exemplary inorganic or organic bases usable in the above reaction include sodium hydride, sodium bis(trimethylsilyl)amide, lithium diisopropylamide and potassium t-butoxide. Illustrative solvents usable in the present reaction include, tetrahydrofuran, dioxane, dimethylformamide, dimethylsulfoxide, N-methylpyrrolidone and toluene. The reaction may be conducted at −78° C. to reflux temperature.

The conversion from the compound (XII) to the compound (Ii) can be effected under conditions similar to those employed upon conversion from the compound (XXVI) to the compound (Ib) in Process 1(a).

Process 7

Among the benzothiazine derivatives (I), each compound (Ij) in which Z is represented by the following formula:

can be synthesized in accordance with the process which will be described hereinafter.

The compound represented by the formula (Ij) can be obtained, in accordance with the following reaction scheme, by subjecting a compound represented by the formula (X) to dehydration to obtain a compound represented by the formula (XIII) and then causing a nitrogen-containing compound represented by the formula (V) to act on the resultant compound.

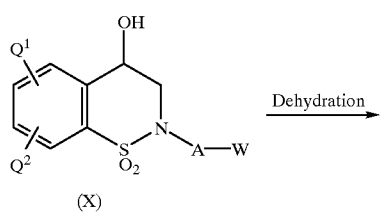

(X)

Dehydration →

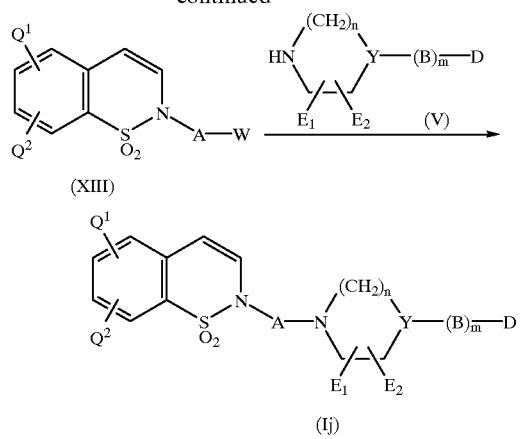

(XIII)

(Ij)

wherein A, B, D, $E_1$, $E_2$, $Q_1$, $Q_2$, W, Y, m and n have the same meanings as defined above.

In the above reactions, the conversion from the compound (X) to the compound (XIII) is conducted by causing methyanesulfonyl chloride or p-toluenesulfonyl chloride and a base such as triethylamine, pyridine or collidine to act on the compound (X) in a solvent such as dichloromethane, chloroform or toluene and then treating the reaction product with the above base or silica gel at room temperature to reflux temperature.

Further, the conversion from the compound (XIII) to the compound (Ij) can be conducted under conditions similar to the conversion from the compound (XXVI) to the compound (Ib) shown in Process I(a).

Process 8

Among the benzothiazine derivatives (I), each compound (Ik) in which Z is represented by the following formula:

can be synthesized in accordance with the process which will be described hereinafter.

The compound represented by the formula (Ik) can be obtained, in accordance with the following reaction scheme, by subjecting a compound represented by the formula (XIII) to reduction to obtain a compound represented by the formula (XIV) and then reacting the resultant compound with a nitrogen-containing compound represented by the formula (V).

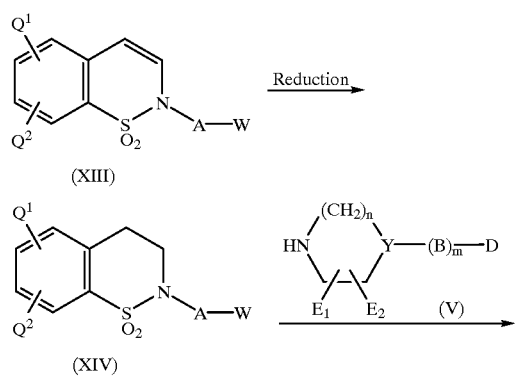

(XIII)

Reduction →

(XIV)

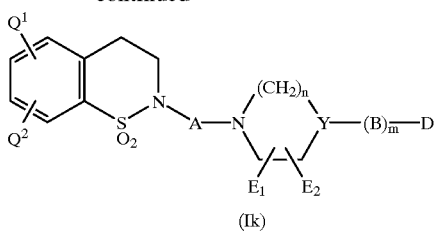

wherein A, B, D, $E_1$, $E_2$, $Q_1$, $Q_2$, W, Y, m and n have the same meanings as defined above.

In the above reactions, the conversion from the compound (XIII) to the compound (XIV) can be conducted in a manner similar to the conversion from the compound (XXXI) to the compound (XXXII) in Process 6.

Further, the conversion from the compound (XIV) to the conversion (Ik) can be conducted under conditions similar to those employed in the conversion of the compound (XXVI) to the compound (Ib) shown in Process 1(a).

The compounds (I) of the present invention obtained according to the above-described processes can each be reacted with one of various acids to convert the compound to its salt. The salt can be purified by a method such as recrystallization or column chromatography.

Exemplary acids usable to convert the benzothiazine derivatives (I) to their salts include inorganic acids such as hydrochloric acid, nitric acid, sulfuric acid, phosphoric acid and hydrobromic acid; and organic acids such as maleic acid, fumaric acid, tartaric acid, lactic acid, citric acid, acetic acid, methanesulfonic acid, p-toluenesulfonic acid, adipic acid, palmitic acid and tannic acid.

As will be demonstrated later by tests, the benzothiazine derivatives (I) and their salts according to the present invention, which can be obtained as described above, have a strong serotonin-2 blocking action and in addition, they have excellent selectivity to $\alpha_1$ blocking action. Further, as a result of a toxicity test, they have been found to feature high safety. The compounds according to the present invention can therefore be used as therapeutics for circulatory diseases such as ischemic heart diseases, cerebrovascular disturbances and peripheral circulatory disturbances.

When the benzothiazine derivative (I) according to this invention are used as drugs, they can be administered in an effective dose as they are. As an alternative, they can also be formulated into various preparation forms by known methods and then administered.

Exemplary preparation forms as drugs include orally administrable preparation forms such as tablets, powders, granules, capsules and syrups as well as parenterally administrable preparation forms such as injections and suppositories. Whichever preparation form is used, a known liquid or solid extender or carrier usable for the formulation of the preparation form can be employed.

Examples of such extender or carrier include polyvinylpyrrolidone, arabic gum, gelatin, sorbit, cyclodextrin, tragacanth gum, magnesium stearate, talc, polyethylene glycol, polyvinyl alcohol, silica, lactose, crystalline cellulose, sugar, starch, calcium phosphate, vegetable oil, carboxymethylcellulose, sodium laurylsulfate, water, ethanol, glycerin, mannitol, syrup, and the like.

When the compounds (I) according to the present invention are used as drugs, their dose varies depending on the administration purpose, the age, body weight and conditions of the patient to be administered, etc. In oral administration, the daily dose may generally be about 0.01–1,000 mg.

The present invention will next be described in further detail by the following examples and tests. It is however borne in mind that the present invention is not limited to the following examples and tests.

EXAMPLE 1

Synthesis of 3,4-dihydro-2H-1,2-benzothiazin-4-one 1,1-dioxide trimethylene acetal (Compound No. 1)

A mixture of 2.96 g (15 mmol) of 3,4-dihydro-2H-1,2-benzothiazin-4-one 1,1-dioxide, 5.71 g (75 mmol) of trimethylene glycol, 285 mg (1.5 mmol) of p-toluenesulfonic acid monohydrate and 75 ml of toluene was refluxed for 30 hours in a container equipped with a Dean & Stark water separator.

The reaction mixture was cooled and then, 100 ml of a 0.02N aqueous solution of sodium hydroxide and ethyl acetate were added to the reaction mixture in this order, followed by fractionation. The resulting organic layer was washed with water and a saturated brine, dried over anhydrous sodium sulfate and then, concentrated under reduced pressure. The oil so obtained was purified by chromatography on a silica gel column in which "No. 9385" (product of Merck & Co., the same silica gel was also used in the subsequent examples) was used as silica gel (eluent: ethyl acetate: hexane=1:1), whereby 1.01 g of the title compound were obtained (yield: 26%).

EXAMPLE 2

Synthesis of 3,4-dihydro-2H-1,2-benzothiazine-4-spiro-2'-[(4'R,5'R)-dimethyl-1',3'-dioxolan]1,1-dioxide (Compound No. 2).

A solution of 410 mg (2.08 mmol) of 3,4-dihydro-2H-1,2-benzothiazin-4-one 1,1-dioxide, 517 mg (5.70 mmol) of (2R,3R)-2,3-butanediol and 38 mg (0.2 mmol) of p-toluenesulfonic acid monohydrate in 10 ml of benzene was refluxed for 20 hours in a container equipped with a Dean & Stark water separator.

Ethyl acetate was added to the reaction mixture. The resulting organic layer was washed with a saturated aqueous solution of sodium bicarbonate, water and saturated brine, dried over anhydrous magnesium sulfate and then, concentrated under reduced pressure. The residue was purified by chromatography on a silica gel column (eluent: methylene chloride:ethyl acetate=30:1), whereby 545 mg of the title compound were obtained (yield: 97%).

EXAMPLE 3

Synthesis of 3,4-dihydro-2H-1,2-benzothiazine-4-spiro-2'-(1',3'-oxathiolan) 1,1-dioxide (Compound No. 3)

Under cooling and stirring, 615 µl (5 mmol) of boron trifluoride ethyl ether complex were added to a solution of 986 mg (5 mmol) of 3,4-dihydro-2H-1,2-benzothiazin-4-one 1,1-dioxide and 586 mg (7.5 mmol) of β-mercaptoethanol in 20 ml of methylene chloride. The reaction mixture was stirred for 27 hours at room temperature. An aqueous solution containing 691 mg (5 mmol) of potassium carbonate were thereafter added to the resulting mixture, followed by extraction with methylene chloride.

The resulting organic layer was washed with water and saturated brine, dried over anhydrous sodium sulfate and then, concentrated under reduced pressure. The residue was purified by chromatography on a silica gel column (eluent:

chloroform), whereby 1.00 g of the title compound was obtained (yield 78%).

EXAMPLE 4

Synthesis of 3,4-dihydro-2H-1,2-benzothiazine-4-spiro-2'-(1',3'-dithiolan) 1,1-dioxide (Compound No. 4)

Under ice cooling and stirring, 250 μl (2 mmol) of boron trifluoride ethyl ether complex were added to a solution of 1.97 g (10 mmol) of 3,4-dihydro-2H-1,2-benzothiazin-4-one 1,1-dioxide and 1.51 g (16 mmol) of 1,2-ethanedithiol in 38 ml of methylene chloride. The reaction mixture was then stirred at room temperature.

Twenty eight hours later, another 250 μl (2 mmol) of boron trifluoride ethyl ether complex were added to the reaction mixture, followed by stirring for further 66 hours. The resulting reaction mixture was post-treated as in Example 3. The crude product so obtained was washed with chloroform, whereby 1.88 g of the title compound were obtained (yield: 69%).

EXAMPLE 5

Synthesis of 3,4-dihydro-2H-1,2-benzothiazine-4-spiro-2'-(1',3'-dithian) 1,1-dioxide (Compound No. 5)

Under cooling and stirring, 710 mg (5 mmol) of boron trifluoride ethyl ether complex were added to a suspension of 1.97 g (10 mmol) of 3,4-dihydro-2H-1,2-benzothiazin-4-one 1,1-dioxide and 1.62 g (15 mmol) of 1,3-propanedithiol in 50 ml of methylene chloride. The reaction mixture was stirred for 24 hours at room temperature. The crystals so precipitated were collected by filtration, followed by washing with methylene chloride.

The filtrate and the wash liquid were combined together, followed by washing with 100 ml of a 1% aqueous solution of potassium carbonate, water and saturated brine, drying over anhydrous sodium sulfate and concentration under reduced pressure. The crude crystals so obtained and the crystals collected by filtration were combined together and recrystallized from acetonitrile, whereby 2.55 g of the title compound were obtained (yield: 89%).

EXAMPLE 6

Synthesis of 4,4-bis(ethylthio)-3,4-dihydro-2H-1,2-benzothiazine 1,1-dioxide (Compound No. 6)

Under cooling and stirring, 50 μl (0.4 mmol) of boron trifluoride ethyl ether complex were added to a solution of 197 mg (1 mmol) of 3,4-dihydro-2H-1,2-benzothiazin-4-one 1,1-dioxide and 223 μl (3 mmol) of ethanethiol in 5 ml of methylene chloride. The reaction mixture was stirred for 1 hour at room temperature. The post-treatment and purification were conducted as in Example 3, whereby 285 mg of the title compound were obtained (yield: 94%).

EXAMPLE 7

Synthesis of 4,4-dimethoxy-3,4-dihydro-2H-1,2-benzothiazine 1,1-dioxide (Compound No. 7)

Under cooling and stirring, 0.75 ml (6 mmol) of boron trifluoride ethyl ether complex was added to a solution of 985 mg (5 mmol) of 3,4-dihydro-2H-1,2-benzothiazin-4-one and 10 ml (91.4 mmol) of methyl orthoformate in 10 ml of methanol, followed by stirring at room temperature. After 85 hours, 0.75 ml (6 mmol) of boron trifluoride ethyl ether complex was added further to the reaction mixture, followed by stirring for 20 hours.

Under ice cooling, the reaction mixture was added with 50 ml of a saturated aqueous solution of sodium bicarbonate and extracted with ethyl acetate. The organic layer was washed with saturated brine, dried over anhydrous magnesium sulfate and then concentrated under reduced pressure. The residue was purified by chromatography on a silica gel column (eluent: ethyl acetate: methylene chloride=1:20), whereby 83 mg of the title compound were obtained (yield: 6.8%).

EXAMPLE 8

Synthesis of 4-methoxy-2H-1,2-benzothiazine 1,1-dioxide (Compound No. 8)

A mixture of 1.97 g (10 mmol) of 3,4-dihydro-2H-1,2-benzothiazin-4-one 1,1-dioxide, 500 mg (2.6 mmol) of p-toluenesulfonic acid monohydrate, 20 ml of methyl orthoformate and 20 ml of methanol was refluxed for 3 hours. The solvent was distilled off and the residue was purified by chromatography on a silica gel column (eluent: methylene chloride:ethyl acetate=40:1), whereby 2.06 g of the title compound were obtained (yield: 97%).

EXAMPLE 9

Synthesis of 4-methoxy-3,4-dihydro-2H-1,2-benzothiazine 1,1-dioxide (Compound No. 9)

A suspension of 1.50 g (7.1 mmol) of Compound No. 8 and 300 mg of 10% palladium-carbon in 70 ml of ethanol was stirred vigorously for 24 hours under hydrogen gas atmosphere. The reaction mixture was filtered and the filtrate was then concentrated under reduced pressure. The residue was purified by chromatography on a silica gel column (eluent: methylene chloride:ethyl acetate=10:1), whereby 1.50 g of the title compound were obtained (yield: 99%).

EXAMPLE 10

Synthesis of 2-(2-chloroethyl)-3,4-dihydro-2H-1,2-benzothiazin-4-one 1,1-dioxide ethylene acetal (Compound No. 10)

To a suspension of 440 mg (11 mmol) of 60% sodium hydride in 20 ml of DMF, a solution of 2.41 g (10 mmol) of 3,4-dihydro-2H-1,2-benzothiazin-4-one 1,1-dioxide ethylene acetal in 10 ml of DMF was added under ice cooling and stirring. The reaction mixture was stirred for one hour at 0° C. and then for further one hour at room temperature. Under ice cooling, a solution of 2.86 g (20 mmol) of 1-bromo-2-chloroethane in 10 ml of DMF was added to the reaction mixture, followed by stirring for 16 hours at room temperature.

The reaction mixture was concentrated under reduced pressure. To the residue, a 3:1 v/v mixed solvent of ethyl acetate and benzene was added. The organic layer was washed with a 5% aqueous solution of citric acid, water (twice) and a saturated brine, dried over anhydrous sodium sulfate and then, concentrated under reduced pressure. The residue was purified by chromatography on a silica gel column (eluent: ethyl acetate:hexane=1:1), whereby 2.55 g of the title compound were obtained (yield: 84%).

EXAMPLE 11

Synthesis of 2-(3-chloropropyl)-3,4-dihydro-2H-1,2-benzothiazin-4-one 1,1-dioxide ethylene acetal (Compound No. 11)

To a suspension of 2.20 g (50 mmol) of 60% sodium hydride in 100 ml of DMF, a solution of 12.06 g (50 mmol)

of 3,4-dihydro-2H-1,2-benzothiazin-4-one 1,1-dioxide ethylene acetal in 50 ml of DMF was added under ice cooling and stirring. The reaction mixture was stirred for 30 minutes at 0° C. and then for further one hour at room temperature. Under ice cooling, a solution of 16.95 g (150 mmol) of 1,3-dichloropropane in 50 ml of DMF was added to the reaction mixture, followed by stirring for 17 hours at room temperature. The post-treatment and purification were conducted as in Example 10, whereby 13.41 g of the title compound were obtained (yield: 84%).

EXAMPLE 12

Synthesis of 2-(4-chlorobutyl)-3,4-dihydro-2H-1,2-benzothiazin-4-one 1,1-dioxide ethylene acetal (Compound No. 12)

In a similar manner to Example 10 except that 1-bromo-2-chloroethane was replaced by the equimolar amount of 1,4-dichlorobutane, the reaction, post-treatment and purification were conducted, whereby 2.53 g of the title compound were obtained (yield: 76%).

EXAMPLE 13

Synthesis of 2-(2-chloroethyl)-3,4-dihydro-2H-1,2-benzothiazine-4-spiro-2'-(1', 3'-dithiolan) 1,1-dioxide (Compound No. 13)

As in Example 10, the reaction and post treatments were conducted using 547 mg (2 mmol) of Compound No. 4, 88 mg (2.2 mmol) of 60% sodium hydride, 574 mg (4 mmol) of 1-bromo-2-chloroethane and 12 ml of DMF.

The crude crystals so obtained were recrystallized from ethyl acetate-hexane, whereby 533 mg of the title compound were obtained (yield: 79%).

EXAMPLE 14

Synthesis of 2-(3-chloropropyl)-3,4-dihydro-2H-1,2-benzothiazine-4-spiro-2'-(1',3'-dithiolan) 1,1-dioxide (Compound No. 14)

As in Example 13, the reaction, post-treatment and purification were conducted employing 10.94 g (40 mmol) of Compound No. 4, 1.76 g (44 mmol) of 60% sodium hydride, 18.89 g (120 mmol) of 1-bromo-3-chloropropane and 160 ml of DMF, whereby 13.17 g of the title compound were obtained (yield: 87%).

EXAMPLE 15

Synthesis of 2-(2-chloroethyl)-3,4-dihydro-2H-1,2-benzothiazine-4-spiro-2'-(1',3'-dithian) 1,1-dioxide (Compound No. 15)

To a suspension of 66 mg (1.65 mmol) of 60% sodium hydride in 10 ml of DMF, a solution of 431 mg (1.5 mmol) of Compound No. 5 in 10 ml of DMF was added under ice cooling and stirring. The reaction mixture was stirred for 1.5 hours at room temperature and then for further 0.5 hour at 50 ° C. Under ice cooling, a solution of 430 mg (3 mmol) of 1-bromo-2-chloroethane in 10 ml of DMF was added to the reaction mixture, followed by stirring for 16 hours at room temperature.

The reaction mixture was concentrated under reduced pressure. To the residue, 50 ml of a half-saturated aqueous solution of potassium carbonate were added, followed by extraction with chloroform. The organic layer was washed with saturated brine, dried over anhydrous sodium sulfate and then, concentrated under reduced pressure. The residue was subjected to chromatography on a silica gel column (eluent: chloroform). The crude crystals so obtained were recrystallized from ethyl acetate-hexane, whereby 403 mg of the title compound were obtained (yield: 77%).

EXAMPLE 16

Synthesis of 2-(3-chloropropyl)-3,4-dihydro-2H-1,2-benzothiazine-4-spiro-2'-(1',3'-dithian) 1,1-dioxide (Compound No. 16)

As in Example 15, the reaction and post-treatment were conducted using 1.15 g (4 mmol) of Compound No. 5, 176 mg (4.4 mmol) of 60% sodium hydride, 1.36 g (12 mmol) of 1,3-dichloropropane and 50 ml of DMF.

The residue was subjected to chromatography on a silica gel column (eluent: ethyl acetate:hexane=1:2). The crude products so obtained were recrystallized from ethyl acetate-hexane, whereby 1.00 g of the title compound were obtained (yield: 69%).

EXAMPLE 17

Synthesis of 2-(3-bromopropyl)-4,4-dimethoxy-3,4-dihydro-2H-1,2-benzothiazine 1,1-dioxide (Compound No. 17)

A suspension of 83 mg (0.34 mmol) of Compound No. 7, 683 mg (3.4 mmol) of 1,3-dibromopropane and 97 mg (0.70 mmol) of potassium carbonate in 5 ml of acetone was refluxed for 4 hours. The reaction mixture was filtered and the filtrate was then concentrated under reduced pressure. The oil so obtained was purified by chromatography on a silica gel column (eluent: ethyl acetate:hexane=1:3), whereby 112 mg of the title compound were obtained (yield: 90%).

EXAMPLE 18

Synthesis of 2-(3-bromopropyl)-4-methoxy-2H-1,2-benzothiazine 1,1-dioxide (Compound No. 18)

A suspension of 527 mg (2.5 mmol) of Compound No. 8, 2.51 g (12.5 mmol) of 1,3-dibromopropane and 690 mg (5 mmol) of potassium carbonate in 37.5 ml of acetone was refluxed for 2 hours. The reaction mixture was filtered and the filtrate was then concentrated under reduced pressure. The residue was purified by chromatography on a silica gel column (eluent: ethyl acetate:hexane=1:4), whereby 706 mg of the title compound were obtained (yield: 85%).

EXAMPLE 19

Synthesis of 2-(3-bromopropyl)-4-methoxy-3,4-dihydro-2H-1,2-benzothiazine 1,1-dioxide (Compound No. 19)

A suspension of 213 mg (1 mmol) of Compound No. 9, 1.00 g (5 mmol) of 1,3-dibromopropane and potassium carbonate in 10 ml of acetone was refluxed for 4 hours. The reaction mixture was filtered and the filtrate was then concentrated under reduced pressure. The residue was purified by chromatography on a silica gel column (eluent: ethyl acetate:hexane=1:3), whereby 294 mg of the title compound were obtained (yield: 88%).

EXAMPLE 20

Synthesis of 2-(3-chloropropyl)-4-methoxy-3,4-dihydro-2H-1,2-benzothiazine 1,1-dioxide (Compound No. 20)

A suspension of 852 mg (4 mmol) of Compound No. 9, 942 mg (6 mmol) of 1-bromo-3-chloropropane and 1.10 g (8 mmol) of potassium carbonate in 40 ml of acetone was refluxed for 10 hours. The reaction mixture was filtered and the filtrate was then concentrated under reduced pressure. The residue was purified by chromatography on a silica gel column (eluent: ethyl acetate:hexane=1:2), whereby 1.11 g of the title compound were obtained (yield: 95%).

EXAMPLE 21

Synthesis of 2-(3-chloropropyl)-3,4-dihydro-2H-1,2-benzothiazin-4-one 1,1-dioxide (Compound No. 21)

A mixture of 3.18 g (10 mmol) of Compound No. 11, 40 ml of 3N hydrochloric acid and 40 ml of methanol was refluxed for 5 hours. The reaction mixture was concentrated under reduced pressure. To the residue, water was added, followed by extraction with methylene chloride. The organic layer was washed with a saturated brine, dried over anhydrous sodium sulfate and then, concentrated under reduced pressure. The residue was purified by chromatography on a silica gel column (eluent: ethyl acetate:hexane=3:2), whereby 2.66 g of the title compound were obtained (yield: 97%).
(Another Process)

In a similar manner to Example 10 except that 3,4-dihydro-2H-1,2-benzothiazin-4-one 1,1-dioxide ethylene acetal and 1-bromo-2-chloroethane were replaced by 1.97 g (10 mmol) of 3,4-dihydro-2H-1,2-benzothiazin-4-one and 4.72 g (30 mmol) of 1-bromo-3-chloropropane, respectively, the reaction, post-treatment and purification were conducted, whereby 721 mg of the title compound were obtained (yield: 26%).

EXAMPLE 22

Synthesis of 2-(3-chloropropyl)-4-hydroxyimino-3,4-dihydro-2H-1,2-benzothiazine 1,1-dioxide (Compound No. 22)

A mixture of 1.64 g (6 mmol) of Compound No. 21, 738 mg (9 mmol) of sodium acetate, 625 mg (9 mmol) of hydroxylamine hydrochloride and 50 ml of methanol was refluxed for 40 hours.

The reaction mixture was concentrated under reduced pressure. To the residue, a half-saturated aqueous solution of potassium carbonate was added, followed by extraction with chloroform. The organic layer was washed with a saturated brine, dried over anhydrous sodium sulfate and then, concentrated under reduced pressure. The residue was purified by chromatography on a silica gel column (eluent: ethyl acetate:hexane=1:2), whereby 1.51 g of the title compound were obtained (yield: 87%).

EXAMPLE 23

Synthesis of 2-(3-chloropropyl)-4-hydroxy-3,4-dihydro-2H-1,2-benzothiazine 1,1-dioxide (Compound No. 23)

Under ice cooling and stirring, 378 mg (10 mmol) of sodium borohydride were added in portions to a solution of 1.09 g (4 mmol) of Compound No. 21 in 40 ml of ethanol. The reaction mixture was stirred for 2 hours at 0° C. and then for 18 hours at room temperature.

The reaction mixture was concentrated under reduced pressure. To the residue, water was added, followed by extraction with methylene chloride. The organic layer was washed with a saturated brine, dried over anhydrous sodium sulfate and then, concentrated under reduced pressure. The residue was purified by chromatography on a silica gel column (eluent: ethyl acetate:hexane=1:1), whereby 1.03 g of the title compound were obtained (yield: 93%).
(Another Process)

A mixture of 398 mg (2 mmol) of 4-hydroxy-3,4-dihydro-2H-1,2-benzothiazine 1,1-dioxide, 471 mg (3 mmol) of 1-bromo-3-chloropropane, 552 mg (4 mmol) of potassium carbonate and 20 ml of acetone was refluxed for 10 hours. The reaction mixture was filtered and the filtrate was then concentrated under reduced pressure. The residue was purified by chromatography on a silica gel column (eluent: methylene chloride:ethyl acetate=20:1), whereby 514 mg of the title compound were obtained (yield: 93%).

EXAMPLE 24

Synthesis of 2-(3-chloropropyl)-4-ethoxy-3,4-dihydro-2H-1,2-benzothiazine 1,1-dioxide (Compound No. 24)

Under ice cooling and stirring, 23 mg (0.57 mmol) of 60% sodium hydride and 0.08 ml (0.94 mmol) of ethyl iodide were successively added to a solution of 130 mg (0.47 mmol) of Compound No. 23 in 2 ml of DMF. The reaction mixture was stirred for one hour under ice cooling and then, for further one hour at room temperature.

Ethyl acetate was added to the reaction mixture. The resulting mixture was washed with an aqueous solution of 10% citric acid (twice), water and a saturated brine, dried over anhydrous sodium sulfate and then, concentrated under reduced pressure. The residue was purified by chromatography on a silica gel column (eluent: ethyl acetate:hexane=1:3), whereby 125 mg of the title compound were obtained (yield: 87%).

EXAMPLE 25

Synthesis of 4-benzyloxy-2-(3-chloropropyl)-3,4-dihydro-2H-1,2-benzothiazine 1,1-dioxide (Compound No. 25)

Under ice cooling, 24 mg (0.60 mmol) of 60% sodium hydride and 0.12 ml (1.0 mmol) of benzyl bromide were added successively to a solution of 138 mg (0.50 mmol) of Compound No. 23 in 2 ml of DMF. The reaction mixture was stirred for one hour under ice cooling and for further one hour at room temperature. The reaction mixture was post-treated as in Example 24. The residue was purified by chromatography on a silica gel column (eluent: ethyl acetate:hexane=1:4), whereby 139 mg of the title compound were obtained (yield: 76%).

EXAMPLE 26

Synthesis of 2-(3-chloropropyl)-2H-1,2-benzothiazine 1,1-dioxide (Compound No. 26)

Under ice cooling and stirring, 1.2 ml (15 mmol) of methanesulfonyl chloride were added to a solution of 1.44 g (5.2 mmol) of Compound No. 23, 3.03 g (30 mmol) of triethylamine in 52 ml of methylene chloride, followed by stirring at 0° C. for one hour.

Ethyl acetate was added to the reaction mixture. The organic layer was washed with 0.5N hydrochloric acid, water, a saturated aqueous solution of sodium bicarbonate and saturated brine, dried over anhydrous sodium sulfate and then concentrated under reduced pressure. The residue was dissolved in 100 ml of methylene chloride and 50 ml of ethyl acetate, followed by the addition of 50 g of silica gel.

After the resulting mixture was stirred at room temperature for 17 hours, the reaction mixture was filtered. The solid matter so obtained was extracted with ethyl acetate. The filtrate and the extract were combined together, followed by washing with a saturated aqueous solution of sodium bicarbonate and saturated brine, drying over anhydrous sodium sulfate and concentration under reduced pressure. The residue was purified by chromatography on a silica gel column (eluent: methylene chloride:ethyl acetate=20:1), whereby 937 mg of the title compound were obtained (yield: 70%).

EXAMPLE 27

Synthesis of 2-(3-chloropropyl)-3,4-dihydro-2H-1,2-benzothiazine 1,1-dioxide (Compound No. 27)

To a solution of 82 mg (0.32 mmol) of Compound No. 26 and three drops of acetic acid in 10 ml of ethanol, 20 mg of 10% palladium-carbon were added, followed by stirring under a hydrogen gas stream for 72 hours. The reaction mixture was filtered. The filtrate was concentrated under reduced pressure. The residue so obtained was purified by chromatography on a silica gel column (eluent: ethyl acetate:hexane=1:3), whereby 73 mg of the title compound were obtained (yield: 88%).

EXAMPLE 28

Synthesis of 2-[3-(4-phenylpiperazin-1-yl)propyl]-3,4-dihydro-2H-1,2-benzothiazin-4-one 1,1-dioxide ethylene acetal (Compound No. 28)

A suspension of 1.27 g (4 mmol) of Compound No. 11, 2.60 g (16 mmol) of 1-phenylpiperazine and 6.00 g (40 mmol) of sodium iodide in 95 ml of DMF was stirred at 80° C. for 16 hours.

To the reaction mixture, 400 ml of a 3:1 v/v mixed solvent of ethyl acetate and benzene were added. The organic layer was washed with a half-saturated aqueous solution of potassium carbonate, water and a saturated brine, dried over anhydrous sodium sulfate and then, concentrated under reduced pressure. The residue was subjected to chromatography on a silica gel column (eluent: ethyl acetate). The crude crystals so obtained were recrystallized from 2-propanol-isopropyl ether, whereby 1.57 g of the title compound were obtained (yield: 88%).

EXAMPLE 29

Synthesis of 2-[2-[4-(4-fluorophenyl)piperazin-1-yl]ethyl]-3,4-dihydro-2H-1,2-benzothiazin-4-one 1,1-dioxide ethylene acetal (Compound No. 29)

A suspension of 607 mg (2 mmol) of Compound No. 10, 721 mg (4 mmol) of 1-(4-fluorophenyl)piperazine and 600 mg (4 mmol) of sodium iodide in 30 ml of acetonitrile was refluxed for 16 hours.

The reaction mixture was concentrated under reduced pressure. To the residue, ethyl acetate was added. The organic layer was washed with a half-saturated aqueous solution of potassium carbonate, water and a saturated brine, dried over anhydrous sodium sulfate and then, concentrated under reduced pressure. The residue was purified by chromatography on a silica gel column (eluent: ethyl acetate:hexane=1:1→ethyl acetate), whereby 443 mg of the title compound were obtained (yield: 49%).

EXAMPLE 30

Synthesis of 2-[4-[4-(4-fluorophenyl)piperazin-1-yl]butyl]-3,4-dihydro-2H-1,2-benzothiazin-4-one 1,1-dioxide ethylene acetal (Compound No. 30)

In a similar manner to Example 29 except that Compound No. 10 was replaced by 663 mg (2 mmol) of Compound No. 12, the reaction, post-treatment and purification were conducted, whereby 697 mg of the title compound were obtained (yield: 73%).

EXAMPLE 31

Synthesis of 2-[3-(4-diphenylmethylpiperazin-1-yl)propyl]-3,4-dihydro-2H-1,2-benzothiazin-4-one 1,1-dioxide ethylene acetal (Compound No. 31)

A suspension of 636 mg (2 mmol) of Compound No. 11, 606 mg (2.4 mmol) of 1-diphenylmethylpiperazine and 332 mg (2.4 mmol) of potassium carbonate in 30 ml of acetonitrile was refluxed for 40 hours. The reaction mixture was post-treated as in Example 22. The residue was subjected to chromatography on a silica gel column (eluent: methanol:chloroform=3:97). The crude crystals so obtained were recrystallized from ethanol, whereby 760 mg of the title compound were obtained (yield: 71%).

EXAMPLE 32

Synthesis of 2-[3-(4-phenylpiperidino)propyl]-3,4-dihydro-2H-1,2-benzothiazin-4-one 1, 1-dioxide ethylene acetal (Compound No. 32)

A suspension of 636 mg (2 mmol) of Compound No. 11, 484 mg (3 mmol) of 4-phenylpiperidine, 415 mg (3 mmol) of potassium carbonate and 600 mg (4 mmol) of sodium iodide in 30 ml of acetonitrile was refluxed for 13 hours.

The post-treatment and purification were conducted as in Example 29, whereby 693 mg of the title compound were obtained (yield: 78%).

EXAMPLE 33

Synthesis of 2-[3-[4-(3-methoxyphenyl)piperazin-1-yl]propyl]-3,4-dihydro-2H-1,2-benzothiazin-4-one 1,1-dioxide ethylene acetal (Compound No. 33)

A suspension of 318 mg (1 mmol) of Compound No. 11, 288 mg (1.5 mmol) of 1-(3-methoxyphenyl)piperazine, 207 mg (1.5 mmol) of potassium carbonate and 300 mg (2 mmol) of sodium iodide in 15 ml of acetonitrile was refluxed for 17 hours. The reaction mixture was post-treated as in Example 31. The residue was subjected to chromatography on a silica gel column (eluent: methanol:chloroform=3:97). The crude crystals so obtained were recrystallized from ethyl acetate-hexane, whereby 326 mg of the title compound were obtained (yield: 69%).

EXAMPLE 34

Synthesis of 2-[3-[4-(4-methoxyphenyl)piperazin-1-yl]propyl]-3,4-dihydro-2H-1,2-benzothiazin-4-one 1,1-dioxide ethylene acetal (Compound 34)

A suspension of 318 mg (1 mmol) of Compound No. 11, 264 mg (1 mmol) of 1-(4-methoxyphenyl)piperazine dihydrochloride, 420 mg (5 mmol) of sodium bicarbonate and 300 mg (2 mmol) of sodium iodide in 15 ml of acetonitrile was refluxed for 20 hours. The reaction mixture was post-treated as in Example 31. The residue was subjected to chromatography on a silica gel column (eluent: methanol:chloroform=1:99), whereby 398 mg of the title compound were obtained (yield: 84%).

EXAMPLE 35

Synthesis of 2-[3-[4-(2-fluorophenyl)piperazin-1-yl]propyl]-3,4-dihydro-2H-1,2-benzothiazin-4-one 1,1-dioxide ethylene acetal (Compound 35)

A suspension of 318 mg (1 mmol) of Compound No. 11, 217 mg (1 mmol) of 1-(2-fluorophenyl)piperazine hydrochloride, 336 mg (4 mmol) of sodium bicarbonate and 300 mg (2 mmol) of sodium iodide in 15 ml of acetonitrile was refluxed for 18 hours. The reaction mixture was post-treated as in Example 31. The residue was subjected to chromatography on a silica gel column (eluent: methanol:chloroform=1:99). The crude crystals so obtained were recrystallized from ethyl acetate-hexane-ethyl ether, whereby 233 mg of the title compound were obtained (yield: 50%).

EXAMPLE 36

Synthesis of 2-[3-[4-(3-fluorophenyl)piperazin-1-yl] propyl]-3,4-dihydro-2H-1,2-benzothiazin-4-one 1,1-dioxide ethylene acetal (Compound No. 36)

In a similar manner to Example 35 except that 1-(2-fluorophenyl)piperazine hydrochloride was replaced by 261 mg (1 mmol) of 1-(3-fluorophenyl)piperazine hydrobromide, the reaction and post-treatment were conducted. The residue was purified by chromatography on a silica gel column (eluent: chloroform), whereby 369 mg of the title compound were obtained (yield: 80%).

EXAMPLE 37

Synthesis of 2-[3-[4-(4-hydroxyphenyl)piperazin-1-yl]propyl]-3,4-dihydro-2H-1,2-benzothiazin-4-one 1,1-dioxide ethylene acetal (Compound No. 37)

In a similar manner to Example 35 except that 1-(2-fluorophenyl)piperazine hydrochloride was replaced by 259 mg (1 mmol) of 1-(4-hydroxyphenyl)piperazine hydrobromide, the reaction and post-treatment were conducted. The residue was purified by chromatography on a silica gel column (eluent: methanol:chloroform=3:97), whereby 286 mg of the title compound were obtained (yield: 62%).

EXAMPLE 38

Synthesis of 2-[3-[4-(4-chlorophenyl)piperazin-1-yl] propyl]-3,4-dihydro-2H-1,2-benzothiazin-4-one 1,1-dioxide ethylene acetal (Compound No. 38)

In a similar manner to Example 35 except that 1-(2-fluorophenyl)piperazine hydrochloride was replaced by 233 mg (1 mmol) of 1-(4-chlorophenyl)piperazine hydrochloride, the reaction and post-treatment were conducted. The residue was purified by chromatography on a silica gel column (eluent: methanol:chloroform=1:99), whereby 434 mg of the title compound were obtained (yield: 90%).

EXAMPLE 39

Synthesis of 2-[3-[4-(4-methanesulfonamidophenyl)-piperazin-1-yl]propyl]-3,4-dihydro-2H-1,2-benzotiazin-4-one 1,1-dioxide ethylene acetal (Compound 39)

A suspension of 159 mg (0.5 mmol) of Compound No. 11, 146 mg (0.5 mmol) of 4-(4-methanesulfonamidophenyl) piperazine hydrochloride, 168 mg (2 mmol) of sodium bicarbonate and 150 mg (1 mmol) of sodium iodide in 15 ml of acetonitrile was refluxed for 16 hours. The reaction mixture was post-treated in a similar manner to Example 22. The residue was purified by chromatography on a silica gel column (eluent: methanol:chloroform=1:99→2:98→3:97), whereby 133 mg of the title compound were obtained (yield: 50%).

EXAMPLE 40

Synthesis of 2-[3-[4-(4-fluorobenzoyl)piperidino]-propyl]-3,4-dihydro-2H-1,2-benzothiazine-4-spiro-2'-(1',3'-dioxolan) 1,1-dioxide (Compound No. 40)

A suspension of 795 mg (2.5 mmol) of Compound No. 11, 609 mg (2.5 mmol) of 4-(4-fluorobenzoyl)piperidine hydrochloride, 804 mg (10 mmol) of sodium bicarbonate and 750 mg (5 mmol) of sodium iodide in 25 ml of acetonitrile was refluxed for 26 hours. The post-treatment and purification were conducted as in Example 31, whereby 1.02 g of the title compound were obtained (yield: 84%).

EXAMPLE 41

Synthesis of 2-[3-[4-(2,4-difluorobenzoyl) piperidino]propyl]-3,4-dihydro-2H-1,2-benzothiazin-4-one 1,1-dioxide ethylene acetal (Compound No. 41)

In a similar manner to Example 39 except that 4-(4-methanesulfonamidophenyl)piperazine hydrochloride was replaced by 157 mg (0.6 mmol) of 4-(2,4-difluorobenzoyl) piperdine hydrochloride, the reaction and the post treatments were conducted. The residue was purified by chromatography on a silica gel column (eluent: methylene chloride:methanol=15:1), whereby 171 mg of the title compound were obtained (yield: 68%).

EXAMPLE 42

Synthesis of 2-[2-[4-(6-fluoro-1,2-benzisoxazol-3-yl)piperidino]ethyl]-3,4-dihydro-2H-1,2-benzothiazin-4-one 1,1-dioxide ethylene acetal (Compound No. 42)

A suspension of 304 mg (1 mmol) of Compound No. 10, 264 mg (1.2 mmol) of 4-(6-fluoro-1,2-benzisoxazol-3-yl) piperidine, 168 mg (2 mmol) of sodium bicarbonate and 300 mg (2 mmol) of sodium iodide in 20 ml of acetonitrile was refluxed for 18 hours.

The reaction mixture was post-treated as in Example 22. The residue was purified by chromatography on a silica gel column (eluent: methylene chloride: methanol=30: 1), whereby 270 mg of the title compound were obtained (yield: 55%).

EXAMPLE 43

Synthesis of 2-[3-[4-(6-fluoro-1,2-benzisoxazol-3-yl)piperidino]propyl]-3,4-dihydro-2H-1,2-benzothiazin-4-one 1,1-dioxide ethylene acetal (Compound No. 43)

A suspension of 95 mg (0.3 mmol) of Compound No. 11, 72 mg (0.3 mmol) of 4-(6-fluoro-1,2-benzisoxazol-3-yl) piperidine, 101 mg (1.2 mmol) of sodium bicarbonate and 90 mg (0.6 mmol) of sodium iodide in 7.5 mi of acetonitrile was refluxed for 22 hours. The reaction mixture was post-treated and purified as in Example 42, whereby 128 mg of the title compound were obtained (yield: 85%).

EXAMPLE 44

Synthesis of 2-[3-[4-(1,2-benzisothiazol-3-yl]-piperazin-1-yl]propyl]-3,4-dihydro-2H-1,2-benzothiazin-4-one 1,1-dioxide ethylene acetal (Compound No. 44)

A suspension of 318 mg (1 mmol) of Compound No. 11, 329 mg (1.5 mmol) of 1-(1,2-benzisothiazol-3-yl)

piperazine, 207 mg (1.5 mmol) of potassium carbonate and 300 mg (2 mmol) of sodium iodide in 15 ml of acetonitrile was refluxed for 15 ours. The reaction mixture was post-treated as in Example 31. The residue was purified by chromatography on a silica gel column (eluent: methanol:chloroform=1:99), whereby 501 mg of the title compound were obtained (yield: 100%).

EXAMPLE 45

Synthesis of 2-[3-[4-(6-fluoro-1H-indazol-3-yl) piperidino]propyl]-3,4-dihydro-2H-1,2-benzothiazin-4-one 1,1-dioxide ethylene acetal (Compound No. 45)

A suspension of 159 mg (0.5 mmol) of Compound No. 11, 164 mg (0.75 mmol) of 4-(6-fluoro-1H-indazol-3-yl) piperidin, 104 mg (0.75 mmol) of potassium carbonate and 150 mg (1 mmol) of sodium iodide in 10 ml of acetonitrile was refluxed for 15 hours. The reaction mixture was post-treated as in Example 22. The residue was subjected to chromatography on a silica gel column (eluent: methanol:chloroform=1:19). The crude crystals so obtained were recrystallized from chloroformethyl ether, whereby 204 mg of the title compound were obtained (yield: 82%).

EXAMPLE 46

Synthesis of 2-[3-[4-(2-pyridyl)piperazin-1-yl]-propyl]-3,4-dihydro-2H-1,2-benzothiazin-4-one 1,1-dioxide ethylene acetal (Compound No. 46)

In a similar manner to Example 44 except that 1-(1,2-benzisothiazol-3-yl)piperazine was replaced by 245 mg (1.5 mmol) of 1-(2-pyridyl)piperazine, the reaction and post-treatment were conducted. The residue so obtained was purified by chromatography on a silica gel column (eluent: methanol:chloroform=2:98), whereby 336 mg of the title compound were obtained (yield: 76%).

EXAMPLE 47

Synthesis of 2-[3-[4-(2-pyrimidinyl)piperazin-1-yl] propyl]-3,4-dihydro-2H-1,2-benzothiazin-4-one 1,1-dioxide ethylene acetal (Compound No. 47)

In a similar manner to Example 34 except that 1-(4-methoxyphenyl)piperazine dihydrochloride was replaced by 237 mg (1 mmol) of 1-(2-pyrimidinyl)piperazine dihydrochloride, the reaction and post-treatment were conducted. The residue so obtained was purified by chromatography on a silica gel column (eluent: methanol:chloroform=2:98), whereby 390 mg of the title compound were obtained (yield: 88%).

EXAMPLE 48

Synthesis of 2-[3-[4-(4-fluorobenzoyl)piperidino] propyl]-3,4-dihydro-2H-1,2-benzothiazine-4-spiro-2'-(1',3'-dithiolan) 1,1-dioxide (Compound No. 48)

A suspension of 350 mg (1 mmol) of Compound No. 14, 244 mg (1 mmol) of 4-(4-fluorobenzoyl)piperidine hydrochloride, 336 mg (4 mmol) of sodium bicarbonate and 300 mg (2 mmol) of sodium iodide in 15 ml of acetonitrile was refluxed for 17 hours. The reaction mixture was post-treated as in Example 22. The residue was purified by chromatography on a silica gel column (eluent: methylene chloride:methanol=97:3), whereby 450 mg of the title compound were obtained (yield: 86%).

EXAMPLE 49

Synthesis of 2-[3-[4-(6-fluoro-1H-indazol-3-yl) piperidino]propyl]-3,4-dihydro-2H-1,2-benzothiazine-4-spiro-2'-(1',3'-dithiolan) 1,1-dioxide (Compound No. 49)

In a similar manner to Example 48 except that 4-(4-fluorobenzoyl)piperidine hydrochloride was replaced by 219 mg (1 mmol) of 4-(6-fluoro-1H-indazol-3-yl)piperidine, the reaction, post-treatment and purification were conducted, whereby 240 mg of the title compound were obtained (yield: 45%).

EXAMPLE 50

Synthesis of 2-[3-[4-(4-hydroxyphenyl)piperazin-1-yl]propyl]-3,4-dihydro-2H-1,2-benzothiazine-4-spiro-2'-(1',3'-dithiolan) 1,1-dioxide (Compound No. 50)

In a similar manner to Example 48 except that 4-(4-fluorobenzoyl)piperidine hydrochloride was replaced by 259 mg (1 mmol) of 1-(4-hydroxyphenyl)piperazine hydrobromide, the reaction and post-treatment were conducted. The residue was subjected to chromatography on a silica gel column (eluent: methylene chloride: methanol= 97:3→19:1). The crude crystals so obtained were recrystallized from acetonitrile-isopropyl ether, whereby 270 mg of the title compound were obtained (yield: 55%).

EXAMPLE 51

Synthesis of 2-[2-[4-(4-fluorophenyl)piperazin-1-yl] ethyl]-3,4-dihydro-2H-1,2-benzothiazine-4-spiro-2'-(1',3'-dithiolan) 1,1-dioxide (Compound No. 51)

A suspension of 336 mg (1 mmol) of Compound No. 13, 276 mg (1.5 mmol) of 1-(4-fluorophenyl)piperazine, 504 mg (6 mmol) of sodium bicarbonate and 300 mg (2 mmol) of sodium iodide in 15 ml of acetonitrile was refluxed for 44 hours. The reaction mixture was post-treated as in Example 31. The residue was subjected to chromatography on a silica gel column (eluent: ethyl acetate:hexane=1:1). The crude crystals so obtained were recrystallized from ethyl acetate-hexane, whereby 315 mg of the title compound were obtained (yield: 66%).

EXAMPLE 52

Synthesis of 2-[2-[4-(4-hydroxyphenyl)piperazin-1-yl]ethyl]-3,4-dihydro-2H-1,2-benzothiazine-4-spiro-2'-(1',3'-dithiolan) 1,1-dioxide (Compound No. 52)

A suspension of 168 mg (0.5 mmol) of Compound No. 13, 130 mg (0.5 mmol) of 1-(4-hydroxyphenyl)piperazine hydrobromide, 168 mg (2 mmol): of sodium bicarbonate and 150 mg (1 mmol) of sodium iodide in 15 ml of acetonitrile was refluxed for 20 hours. The reaction mixture was filtered and the filtrate was concentrated under reduced pressure. The residue was subjected to chromatography on a silica gel column (eluent: methanol:chloroform=3:97). The crude crystals so obtained were recrystallized from ethyl acetate-hexane, whereby 78 mg of the title compound were obtained (yield: 33%).

EXAMPLE 53

Synthesis of 2-[3-[4-(4-hydroxyphenyl)piperazin-1-yl]propyl]-3,4-dihydro-2H-1,2-benzothiazine-4-spiro-2'-(1',3'-dithian) 1,1-dioxide (Compound No. 53)

As in Example 52, the reaction and post-treatment were conducted employing 364 mg (1 mmol) of Compound No.

16, 259 mg (1 mmol) of 1-(4-hydroxyphenyl)piperazine hydrobromide, 336 mg (4 mmol) of sodium bicarbonate, 300 mg (2 mmol) of sodium iodide and 20 ml of acetonitrile. The residue was purified by chromatography on a silica gel column (eluent: methanol:chloroform=3:97), whereby 337 mg of the title compound were obtained (yield: 67%).

EXAMPLE 54

Synthesis of 2-[2-[4-(4-hydroxyphenyl)piperazin-1-yl]ethyl]-3,4-dihydro-2H-1,2-benzothiazine-4-spiro-2'-(1',3'-dithian) 1,1-dioxide (Compound No. 54)

In a similar manner to Example 53 except that Compound No. 16 was replaced by 350 mg (1 mmol) of Compound No. 15, the reaction and post-treatment were conducted. The residue was subjected to chromatography on a silica gel column (eluent: methanol: chloroform 3:97). The crude crystals so obtained were recrystallized from acetonitrile-isopropyl ether, whereby 100 mg of the title compound were obtained (yield: 20%).

EXAMPLE 55

Synthesis of 2-[3-[4-(4-fluorophenyl)piperazin-1-yl] propyl]-4,4-dimethoxy-3,4-dihydro-2H-1,2-benzothiazine 1,1-dioxide (Compound No. 55)

A suspension of 112 mg (0.3 mmol) of Compound No. 17, 81 mg (0.45 mmol) of 1-(4-fluorophenyl)piperazine and 83 mg (0.6 mmol) of potassium carbonate in 10 ml of 1,4-dioxane was stirred at 90° C. for 15 hours. The reaction mixture was filtered and the filtrate was then concentrated under reduced pressure. The residue was purified by chromatography on a silica gel column (eluent: methanol:methylene chloride=1:30), whereby 146 mg of the title compound were obtained (yield: 99%).

EXAMPLE 56

Synthesis of 2-[3-[4-(4-fluorophenyl)piperazin-1-yl] propyl]-4-methoxy-2H-1,2-benzothiazine 1,1-dioxide (Compound No. 56)

A suspension of 664 mg (2 mmol) of Compound No. 18, 432 mg (2.4 mmol) of 1-(4-fluorophenyl)piperazine and 552 mg (4 mmol) of potassium carbonate in 30 ml of 1,4-dioxane was refluxed for 13 hours. The reaction mixture was filtered and the filtrate was then concentrated under reduced pressure. The residue was purified by chromatography on a silica gel column (eluent: methylene chloride:methanol=40:1), whereby 785 mg of the title compound were obtained (yield: 91%).

EXAMPLE 57

Synthesis of 2-[3-[4-(4-fluorophenyl)piperazin-1-yl] propyl]-4-methoxy-3,4-dihydro-2H-1,2-benzothiazine 1,1-dioxide (Compound No. 57)

A suspension of 250 mg (0.74 mmol) of Compound No. 19, 170 mg (0.90 mmol) of 1-(4-fluorophenyl)piperazine and 207 mg (1.5 mmol) of potassium carbonate in 10 ml of 1,4-dioxane was refluxed for 6 hours. The reaction mixture was filtered and the filtrate was then concentrated under reduced pressure. The residue was purified by chromatography on a silica gel column (eluent: methylene chloride:methanol=30:1), whereby 303 mg of the title compound were obtained (yield: 94%).

EXAMPLE 58

Synthesis of 2-[3-[4-(4-fluorobenzoyl)piperidino]-propyl]-4-methoxy-3,4-dihydro-2H-1,2-benzothiazine 1,1-dioxide (Compound No. 58)

A suspension of 145 mg (0.5 mmol) of Compound No. 20, 182 mg (0.75 mmol) of 4-(4-fluorobenzoyl)piperdine hydrochloride, 168 mg (2 mmol) of sodium bicarbonate and 150 mg (1 mmol) of sodium iodide in 10 ml of acetonitrile was refluxed for 20 hours. The reaction mixture was post-treated as in Example 31. The residue was purified by chromatography on a silica gel column (eluent: methylene chloride: methanol=20:1), whereby 220 mg of the title compound were obtained (yield: 95%).

EXAMPLE 59

Synthesis of 4-ethoxy-2-[3-[4-(4-fluorophenyl) piperazin-1-yl]propyl]-3,4-dihydro-2H-1,2-benzothiazine 1,1-dioxide (Compound No. 59)

A suspension of 152 mg (0.5 mmol) of Compound No. 24, 135 mg (0.75 mmol) of 1-(4-fluorophenyl)piperazine, 84 mg (1.0 mmol) of sodium bicarbonate and 150 mg (1 mmol) of sodium iodide in 10 ml of acetonitrile was refluxed for 19 hours. The reaction mixture was post-treated as in Example 31. The residue was purified by chromatography on a silica gel column (eluent: methylene chloride:methanol=30:1), whereby 190 mg of the title compound were obtained (yield: 85%).

EXAMPLE 60

Synthesis of 2-[3-[4-(4-hydroxyphenyl)piperazin-1-yl]propyl]-4-methoxy-3,4-dihydro-2H-1,2-benzothiazine 1,1-dioxide (Compound No. 60)

A suspension of 145 mg (0.5 mmol) of Compound No. 20, 155 mg (0.6 mmol) of 1-(4-hydroxyphenyl)piperazine hydrobromide, 168 mg (2 mmol) of sodium bicarbonate and 150 mg (1 mmol) of sodium iodide in 10 ml of acetonitrile was refluxed for 20 hours. The reaction mixture was post-treated as in Example 31. The residue was purified by chromatography on a silica gel column (eluent: methylene chloride:methanol=15:1), whereby 70 mg of the title compound were obtained (yield: 32%).

EXAMPLE 61

Synthesis of 4-benzyloxy-2-[3-[4-(4-fluorophenyl) piperazin-1-yl]propyl]-3,4-dihydro-2H-1,2-benzothiazine 1,1-dioxide (Compound No. 61)

A suspension of 109 mg (0.3 mmol) of Compound No. 25, 81 mg (0.45 mmol) of 1-(4-fluorophenyl)piperazine, 50 mg (0.6 mmol) of sodium bicarbonate and 90 mg (0.6 mmol) of sodium iodide in 6 ml of acetonitrile was refluxed for 18 hours. The reaction mixture was post-treated as in Example 31. The residue was purified by chromatography on a silica gel column (eluent: methylene chloride:methanol=40:1), whereby 120 mg of the title compound were obtained (yield: 78%).

EXAMPLE 62

Synthesis of 2-[3-[4-(4-fluorophenyl)piperazin-1-yl] propyl]-3,4-dihydro-2H-1,2-benzothiazin-4-one 1,1-dioxide ethylene acetal (Compound No. 62)

Under ice cooling and stirring, a solution of 2.42 g (10 mmol) of 3,4-dihydro-2H-1,2-benzothiazin-4-one 1,1-dioxide ethylene acetal in 20 ml of DMF was added to a suspension of 480 mg (12 mmol) of 60% sodium hydride in 60 ml of DMF. The reaction mixture was stirred for one hour at 0° C. and for further one hour at room temperature.

The reaction mixture was thereafter cooled to 0° C., to which a solution of 3.85 g (15 mmol) of 1-(3-chloropropyl)-

4-(4-fluorophenyl)piperazine in 20 ml of DMF was added. The resulting mixture was stirred at room temperature for 58 hours. The reaction mixture was post-treated as in Example 28. The residue was purified by chromatography on a silica gel column (eluent: ethyl acetate:hexane=3:1→ethyl acetate), whereby 4.30 g of the title compound were obtained (yield: 93%).

EXAMPLE 63

Synthesis of 2-[3-[4-(4-fluorophenyl)piperazin-1-yl] propyl]-3,4-dihydro-2H-1,2-benzothiazine-4-spiro-2'-[(4'R,5'R)-dimethyl-1',3'-dioxolan]1,1-dioxide (Compound No. 63)

As in Example 62, the reaction was conducted using 24 mg (0.6 mmol) of 60% sodium hydride, 135 mg (0.5 mmol) of Compound No. 2, 192 mg (0.75 mmol) of 1-(3-chloropropyl)-4-(4-fluorophenyl)piperazine and 6 ml of DMF. The reaction mixture was post-treated as in Example 22. The residue was purified by chromatography on a silica gel column (eluent: methylene chloride: methanol=20: 1), whereby 176 mg of the title compound were obtained (yield: 72%).

EXAMPLE 64

Synthesis of 2-[3-[4-(4-fluorophenyl)piperazin-1-yl] propyl]-3,4-dihydro-2H-1,2-benzothiazine-4-spiro-2'-(1',3'-dioxane) 1,1-dioxide (Compound No. 64)

As in Example 62, the reaction, post-treatment and purification were conducted employing 185 mg (4.63 mmol) of 60% sodium hydride, 987 mg (3.86 mmol) of Compound No. 1, 1.49 g (5.79 mmol) of 1-(3-chloropropyl)-4-(4-fluorophenyl)piperazine and 50 ml of DMF, whereby 1.33 g of the title compound were obtained (yield: 72%).

EXAMPLE 65

Synthesis of 2-[3-[4-(4-fluorophenyl)piperazin-1-yl] propyl]-3,4-dihydro-2H-1,2-benzothiazine-4-spiro-2'-(1',3'-oxathiolan) 1,1-dioxide (Compound No. 65)

The reaction, post-treatment and purification were conducted as in Example 62 by employing 96 mg (2.4 mmol) of 60% sodium hydride, 515 mg (2 mmol) of Compound No. 3, 770 mg (3 mmol) of 1-(3-chloropropyl)-4-(4-fluorophenyl)piperazine and 25 ml of DMF, whereby 635 mg of the title compound were obtained (yield: 66%).

EXAMPLE 66

Synthesis of 2-[3-[4-(4-fluorophenyl)piperazin-1-yl] propyl]-3,4-dihydro-2H-1,2-benzothiazine-4-spiro-2'-(1',3'-dithiolan) 1,1-dioxide (Compound No. 66)

The reaction, post-treatment and purification were conducted as in Example 62 by employing 88 mg (2.2 mmol) of 60% sodium hydride, 547 mg (2 mmol) of Compound No. 4, 770 mg (3 mmol) of 1-(3-chloropropyl)-4-(4-fluorophenyl)piperazine and 25 ml of DMF, whereby 950 mg of the title compound were obtained (yield: 96%).

EXAMPLE 67

Synthesis of 2-[3-[4-(4-fluorophenyl)piperazin-1-yl] propyl]-3,4-dihydro-2H-1,2-benzothiazine-4-spiro-2'-(1',3'-dithian) 1,1-dioxide (Compound No. 67)

As in Example 62, the reaction was conducted using 44 mg (1.1 mmol) of 60%-sodium hydride, 287 mg (1 mmol) of Compound No. 5, 385 mg (1.5 mmol) of 1-(3-chloropropyl)-4-(4-fluorophenyl)piperazine and 20 ml of DMF.

The reaction mixture was concentrated under reduced pressure. A half-saturated aqueous solution of potassium carbonate was added to the residue, followed by extraction with ethyl acetate. The organic layer was washed with saturated brine, dried over anhydrous sodium sulfate and concentrated under reduced pressure. The residue was purified by chromatography on a silica gel column (eluent: chloroform), whereby 442 mg of the title compound were obtained (yield: 87%).

EXAMPLE 68

Synthesis of 2-[2-[4-(4-fluorophenyl)piperazin-1-yl] ethyl]-3,4-dihydro-2H-1,2-benzothiazine-4-spiro-2'-(1',3'-dithian) 1,1-dioxide (Compound No. 68)

In a similar manner to Example 67 except that 1-( 3-chloropropyl)-4-(4-fluorophenyl)piperazine was replaced by 364 mg (1.5 mmol) of 1-(2-chloroethyl)-4-(4-fluorophenyl)piperazine, the reaction was conducted.

As in Example 51, the post-treatments and purification were conducted, whereby 247 mg of the title compound were obtained (yield: 50%).

EXAMPLE 69

Synthesis of 4,4-bis(ethylthio)-2-[3-[4-(4-fluorophenyl)piperazin-1-yl]propyl]-3,4-dihydro-2H-1,2-benzothiazine 1,1-dioxide (Compound No. 69)

In a similar manner to Example 65 except that Compound No. 3 was replaced by 607 mg (2 mmol) of Compound No. 6, the reaction, post-treatment and purification were conducted, whereby 814 mg of the title compound were obtained (yield: 78%).

EXAMPLE 70

Synthesis of 2-[3-[4-(4-fluorophenyl)piperazin-1-yl] propyl]-3,4-dihydro-2H-1,2-benzothiazin-4-one 1,1-dioxide (Compound No. 70)

A mixture of 923 mg (2 mmol) of Compound No. 62, 25 ml of 3N hydrochloric acid and 25 ml of methanol was refluxed for 2 hours. The reaction mixture was concentrated under reduced pressure. To the residue, 200 ml of a half-saturated aqueous solution of potassium carbonate were added, followed by extraction with chloroform. The organic layer was washed with a saturated brine, dried over anhydrous sodium sulfate and then, concentrated under reduced pressure. The residue was purified by chromatography on a silica gel column (eluent: ethyl acetate:hexane=2:1), whereby 772 mg of the title compound were obtained (yield: 92%).

EXAMPLE 71

Synthesis of 2-[3-(4-phenylpipierazin-1-yl)propyl]-3,4-dihydro-2H-1,2-benzothiazin-4-one 1,1-dioxide (Compound No. 71)

In a similar manner to Example 70 except that Compound No. 62 was replaced by 887 mg (2 mmol) of Compound No. 28, the reaction, post-treatment and purification were conducted, whereby 719 mg of the title compound were obtained (yield: 90%).

EXAMPLE 72

Synthesis of 2-[3-[4-(4-fluorobenzoyl)piperidino]-propyl]-3,4-dihydro-2H-1,2-benzothiazin-4-one 1,1-dioxide (Compound No. 72)

A mixture of 600 mg (1.2 mmol) of Compound No. 40, 5 ml of 3N hydrochloric acid and 5 ml of methanol was refluxed for 1.5 hours. The reaction mixture was post-treated as in Example 70. The residue was purified by chromatography on a silica gel column (eluent: methylene chloride:methanol=30:1), whereby 483 mg of the title compound were obtained (yield: 90%).

EXAMPLE 73

Synthesis of 4-hydroxyimino-2-[3-(4-phenylpiperazin-1-yl)propyl]-3,4-dihydro-2H-1,2-benzothiazine 1,1-dioxide (Compound No. 73)

A suspension of 230 mg (0.797 mmol) of Compound No. 22, 517 mg (3.19 mmol) of 1-phenylpiperazine and 1.19 g (7.97 mmol) of sodium iodide in 20 ml of DMF was stirred at 80° C. for 16 hours. The post-treatment and purification were conducted as in Example 62, whereby 239 mg of the title compound were obtained (yield: 72%).

EXAMPLE 74

Synthesis of 2-[3-[4-(4-fluorobenzoyl)piperidino]-propyl]-4-hydroxyimino-3,4-dihydro-2H-1,2-benzothiazine 1,1-dioxide (Compound No. 74)

A suspension of 722 mg (2.5 mmol) of Compound No. 22, 609 mg (2.5 mmol) of 4-(4-fluorobenzoyl)piperidine hydrochloride, 840 mg (10 mmol) of sodium bicarbonate and 749 mg (5 mmol) of sodium iodide in 50 ml of acetonitrile was refluxed for 24 hours.

The reaction mixture was concentrated under reduced pressure. To the residue, a half-saturated aqueous solution of potassium carbonate was added, followed by extraction with dichloromethane and ethyl acetate. The organic layer was washed with a saturated brine, dried over anhydrous sodium sulfate and then, concentrated under reduced pressure. The solid matters so obtained were washed with methanol and then, recrystallized from acetonitrile, whereby 533 mg of the title compound were obtained (yield: 46%).

EXAMPLE 75

Synthesis of 2-[3-[4-(4-fluorophenyl)piperazin-1-yl] propyl]-4-hydroxyimino-3,4-dihydro-2H-1,2-benzothiazine 1,1-dioxide (Compound No. 75)

A solution of 1.25 g (3 mmol) of Compound No. 70, 417 mg (6 mmol) of hydroxylamine hydrochloride and 492 mg (6 mmol) of sodium acetate in 30 ml of methanol was refluxed for 3 hours. The reaction mixture was post-treated as in Example 22. The residue was purified by chromatography on a silica gel column (eluent: methanol:chloroform= 3:97), whereby 1.27 g of the title compound were obtained (yield: 98%).

EXAMPLE 76

Synthesis of 2-[3-[4-(4-fluorobenzoyl)piperidino]-propyl]-4-hydroxy-3,4-dihydro-2H-1,2-benzothiazine 1,1-dioxide (Compound No. 76)

In a similar manner to Example 74 except that Compound No. 22 was replaced by 689 mg (2.5 mmol) of Compound No. 23, the reaction was conducted. The reaction mixture was post-treated as in Example 31. The residue was purified by chromatography on a silica gel column (eluent: methanol:chloroform=7.5:92.5), whereby 818 mg of the title compound were obtained (yield: 92%).

EXAMPLE 77

Synthesis of 2-[3-[4-(4-fluorophenyl)piperazin-1-yl] propyl]-4-hydroxy-3,4-dihydro-2H-1,2-benzothiazine 1,1-dioxide (Compound No. 77)

Under ice cooling and stirring, 300 mg (7.9 mmol) of sodium borohydride were added in portions to a solution of 209 mg (0.5 mmol) of Compound No. 70 in 30 ml of ethanol. The reaction mixture was stirred for one hour at 0° C. and for further 16 hours at room temperature.

The reaction mixture was post-treated as in Example 23. The residue was then purified by chromatography on a silica gel column (eluent: ethyl acetate), whereby 201 mg of the title compound were obtained (yield: 96%).

EXAMPLE 78

Synthesis of 2-[3-[4-(4-fluorophenyl)piperazin-1-yl] propyl]-2H-1,2-benzothiazine 1,1-dioxide (Compound No. 78)

A suspension of 69 mg (0.27 mmol) of Compound No. 26, 58 mg (0.32 mmol) of 1-(4-fluorophenyl)piperazine, 45 mg (0.54 mmol) of sodium bicarbonate and 81 mg (0.54 mmol) of sodium iodide in 5 ml of acetonitrile was refluxed for 20 hours. The reaction mixture was post-treated and purified as in Example 63, whereby 97 mg of the title compound were obtained (yield: 89%).

EXAMPLE 79

Synthesis of 2-[3-[4-(4-fluorophenyl)piperazin-1-yl] propyl]-3,4-dihydro-2H-1,2-benzothiazine 1,1-dioxide (Compound No. 79)

As in Example 78, the reaction, post-treatment and purification were conducted employing 73 mg (0.28 mmol) of Compound No. 27, 60 mg (0.34 mmol) of 1-(4-fluorophenyl)piperazine, 47 mg (0.56 mmol) of sodium bicarbonate, 84 mg (0.56 mmol) of sodium iodide and 5 ml of acetonitrile, whereby 108 mg of the title compound were obtained (yield: 96%).

EXAMPLE 80

Synthesis of 2-acetonyl-4-methoxy-1,2-benzisothiazol-3(2H)-one 1,1-dioxide (Compound No. 80)

2.4 ml of 28% sodium methoxide solution in methanol (12 mmol) was added under ice cooling and stirring to a suspension of 2.34 g (11 mmol) of 4-methoxysaccharin in 20 ml of methanol, followed by stirring at 0° C. for 1 hour. The reaction mixture was concentrated under reduced pressure, and the residue was washed with ethyl ether and dried, whereby the sodium salt of 4-methoxysaccharin was obtained in the form of powder.

A solution of the thus-obtained sodium salt and 1.22 g (13.2 mmol) of chloroacetone in 20 ml of DMF was stirred at 90–95° C. for 5 hours. The reaction mixture was concentrated under reduced pressure. A 3:1 mixed solvent of ethyl acetate and dichloromethane was added to the residue. The resulting solution was washed successively with water, a saturated aqueous solution of sodium hydrogencarbonate and a saturated aqueous solution of sodium chloride, dried over anhydrous sodium sulfate, and then concentrated under reduced pressure. The residue was purified by chromatography on a silica gel column (eluent: methylene chloride:ethyl acetate=50:1), whereby 2.78 g of the title compound were obtained (yield: 94%).

EXAMPLE 81

Synthesis of 2-acetonyl-4-chloro-1,2-benzisothiazol-3(2H)-one 1,1-dioxide (Compound No. 81)

4.4 ml of 28% sodium methoxide solution in methanol (22 mmol) was added under ice cooling and stirring to a suspension of 4.36 g (20 mmol) of 4-chlorosaccharin in 40 ml of methanol, followed by stirring at 0° C. for 30 minutes. The reaction mixture was treated as in Example 80, whereby the sodium salt of 4-chlorosaccharin was obtained in the form of powder.

A solution of the thus-obtained sodium salt and 2.21 g (24 mmol) of chloroacetone in 40 ml of DMF was stirred at 90–95° C. for 15 hours. Post-treatments were conducted as in Example 80. The residue was purified by chromatography on a silica gel column (eluent: methylene chloride:ethyl acetate=30:1), whereby 4.70 g of the title compound were obtained (yield: 86%).

EXAMPLE 82

Synthesis of 2-acetonyl-5-methoxy-1,2-benzisothiazol-3(2H)-one 1,1-dioxide (Compound No. 82)

3.2 ml of 28% sodium methoxide solution in methanol (16 mmol) was added under ice cooling and stirring to a suspension of 3.10 g (14.5 mmol) of 5-methoxysaccharin in 30 ml of methanol, followed by stirring at 0° C. for 15 minutes. The reaction mixture was treated as in Example 80, whereby the sodium salt of 5-methoxysaccharin was obtained in the form of powder.

A solution of the thus-obtained sodium salt and 2.23 g (24.2 mmol) of chloroacetone in 30 ml of DMF was stirred at 90–95° C. for 5 hours. The reaction mixture was concentrated under reduced pressure. A 1:4 mixed solvent of ethyl acetate and dichloromethane was added to the residue. The resulting solution was washed successively with water, a saturated aqueous solution of sodium hydrogencarbonate and a saturated aqueous solution of sodium chloride, dried over anhydrous sodium sulfate, and then concentrated under reduced pressure. The residue was purified by chromatography on a silica gel column (eluent: methylene chloride:ethyl acetate=50:1), whereby 3.85 g of the title compound were obtained (yield: 98%).

EXAMPLE 83

Synthesis of 2-acetonyl-5-chloro-1,2-benzisothiazol-3(2H)-one 1,1-dioxide (Compound No. 83)

1.76 ml of 28% sodium methoxide solution in methanol (8.8 mmol) was added under ice cooling and stirring to a solution of 1.74 g (8 mmol) of 5-chlorosaccharin in 80 ml of methanol, followed by stirring at room temperature for 20 minutes. The reaction mixture was treated as in Example 80, whereby the sodium salt of 5-chlorosaccharin was obtained in the form of powder.

A solution of the thus-obtained sodium salt and 669 μl (8.4 mmol) of chloroacetone in 7 ml of DMF was stirred at 100° C. for 15 hours. The reaction mixture was concentrated under reduced pressure. To the residue was added water, and extracted twice with chloroform. Organic layers were washed with a saturated aqueous solution of sodium chloride, dried over anhydrous sodium sulfate, and then concentrated under reduced pressure. The residue was purified by chromatography on a silica gel column (eluent: chloroform), whereby 1.38 g of the title compound were obtained (yield: 63%).

EXAMPLE 84

Synthesis of 2-acetonyl-6-methoxy-1,2-benzisothiazol-3(2H)-one 1,1-dioxide (Compound No. 84)

2 ml of 28% sodium methoxide solution in methanol (10 mmol) was added under ice cooling and stirring to a suspension of 1.9 g (9 mmol) of 6-methoxysaccharin in 18 ml of methanol, followed by stirring at 0° C. for 15 minutes. The reaction mixture was treated as in Example 80, whereby the sodium salt of 6-methoxysaccharin was obtained in the form of powder.

A solution of the thus-obtained sodium salt and 1.39 g (15 mmol) of chloroacetone in 18 ml of DMF was stirred at 90–95° C. for 20 hours. Post-treatments and purification were conducted as in Example 82, whereby 2.26 g of the title compound were obtained (yield: 93%).

EXAMPLE 85

Synthesis of 2-acetonyl-6-chloro-1,2-benzisothiazol-3(2H)-one 1,1-dioxide (Compound No. 85)

6.6 ml of 28% sodium methoxide solution in methanol (33 mmol) was added under ice cooling and stirring to a suspension of 6.54 g (30 mmol) of 6-chlorosaccharin in 60 ml of methanol, followed by stirring at 0° C. for 15 minutes. The reaction mixture was treated as in Example 80, whereby the sodium salt of 6-chlorosaccharin was obtained in the form of powder.

A solution of the thus-obtained sodium salt and 3.30 g (36 mmol) of chloroacetone in 60 ml of DMF was stirred at 90–95° C. for 12 hours. Post-treatments and purification were conducted as in Example 82, whereby 7.37 g of the title compound were obtained (yield: 89%).

EXAMPLE 86

Synthesis of 3-acetyl-5-methoxy-2H-1,2-benzothiazin- 4(3H)-one 1,1-dioxide (Compound No. 86)

Compound No. 80 (2.42 g, 9 mmol) was added at 45° C. to a solution of 414 mg (18 mmol) of sodium in 9 ml of ethanol, followed by stirring for 10 minutes. The reaction mixture was ice-cooled, to which 11.3 ml (22.6 mmol) of 2 N hydrochloric acid were added. Precipitated crystals were collected by filtration, washed with water and then dried, whereby 1.55 g of the title compound were obtained (yield: 64%).

EXAMPLE 87

Synthesis of 3-acetyl-5-chloro-2H-1,2-benzothiazin-4(3H)-one 1,1-dioxide (Compound No. 87)

Compound No. 81 (4.10 g, 15 mmol) was added at 50° C. to a solution of 690 mg (30 mmol) of sodium in 15 ml of ethanol, followed by stirring for 10 minutes. The reaction mixture was ice-cooled, to which 18.7 ml (37.4 mmol) of 2 N hydrochloric acid were added. Precipitated crystals were collected by filtration, washed with water and then dried, whereby 3.00 g of the title compound were obtained (yield: 73%).

EXAMPLE 88

Synthesis of 3-acetyl-6-methoxy-2H-1,2-benzothiazin-4(3H)-one 1,1-dioxide (Compound No. 88)

Compound No. 82 (3.50 g, 13 mmol) was added at 50° C. to a solution of 600 mg (26 mmol) of sodium in 13 ml of ethanol, followed by stirring for 10 minutes. The reaction mixture was ice-cooled, to which 15 ml (30 mmol) of 2 N hydrochloric acid were added. Precipitated crystals were collected by filtration, washed with water and then dried, whereby 2.90 g of the title compound were obtained (yield: 83%).

EXAMPLE 89

Synthesis of 3-acetyl-6-chloro-2H-1,2-benzothiazin-4(3H)-one 1,1-dioxide (Compound No. 89)

Compound No. 83 (1.26 g, 4.6 mmol) was added at 40° C. to a solution of 212 mg (9.2 mmol) of sodium in 4.1 ml of ethanol, followed by stirring at 50–55° C. for 5 minutes. The reaction mixture was ice-cooled, to which 5.75 ml (11.5 mmol) of 2 N hydrochloric acid were added. Precipitated crystals were collected by filtration, washed with 50% water-ethanol and then dried, whereby 1.15 g of the title compound were obtained (yield: 91%).

EXAMPLE 90

Synthesis of 3-acetyl-7-methoxy-2H-1,2-benzothiazin-4(3H)-one 1,1-dioxide (Compound No. 90)

Compound No. 84 (2.15 g, 8 mmol) was added at 45° C. to a solution of 368 mg (16 mmol) of sodium in 7.2 ml of ethanol, followed by stirring for 10 minutes. The reaction mixture was ice-cooled, to which 10 ml (20 mmol) of 2 N hydrochloric acid were added. Precipitated crystals were collected by filtration, washed with water and then dried, whereby 1.70 g of the title compound were obtained (yield: 81%).

EXAMPLE 91

Synthesis of 3-acetyl-7-chloro-2H-1,2-benzothiazin-4(3H)-one 1,1-dioxide (Compound No. 91)

Compound No. 85 (6.84 g, 25 mmol) was added at 45° C. to a solution of 1.15 g (50 mmol) of sodium in 22.5 ml of ethanol, followed by stirring for 10 minutes. The mixture was ice-cooled, to which 32 ml (64 mmol) of 2 N hydrochloric acid were added. Precipitated crystals were collected by filtration, washed with water and then dried, whereby 6.18 g of the title compound were obtained (yield: 90%).

EXAMPLE 92

Synthesis of 5-methoxy-3,4-dihydro-2H-1,2-benzothiazin-4-one 1,1-dioxide ethylene acetal (Compound No. 92)

A solution of 935 mg (3.4 mmol) of Compound No. 86, 1.05 g (17 mmol) of ethylene glycol and 65 mg (0.34 mmol) of p-toluenesulfonic acid monohydrate in 30 ml of benzene was refluxed in a vessel equipped with a Dean & Stark water separator. Seventy (70) hours later, 1.05 g (17 mmol) of ethylene glycol were added, followed by further reflux for 24 hours. The solvent was concentrated to 15 ml under reduced pressure and crystals were collected by filtration. They were recrystallized from acetonitrile, whereby 590 mg of the title compound were obtained (yield: 64%).

EXAMPLE 93

Synthesis of 5-chloro-3,4-dihydro-2H-1,2-benzothiazin-4-one 1,1-dioxide ethylene acetal (Compound No. 93)

A solution of 2.73 g (10 mmol) of Compound No. 87, 3.10 g (50 mmol) of ethylene glycol and 190 mg (1 mmol) of p-toluenesulfonic acid monohydrate in 100 ml of benzene was refluxed in a vessel equipped with a Dean & Stark water separator. Eighty-four (84) hours later, 3.10 g (50 mmol) of ethylene glycol and 190 mg (1 mmol) of p-toluenesulfonic acid monohydrate were added, followed by further reflux for 84 hours. The reaction mixture was concentrated under reduced pressure, ethyl acetate was added to the residue, and crystals were collected by filtration. They were recrystallized from acetonitrile, whereby 1.00 g of the title compound was obtained (yield: 36%).

EXAMPLE 94

Synthesis of 6-methoxy-3,4-dihydro-2H-1,2-benzothiazin-4-one 1,1-dioxide ethylene acetal (Compound No. 94)

A solution of 2.70 g (10 mmol) of Compound No. 88, 3.10 g (50 mmol) of ethylene glycol and 190 mg (1 mmol) of p-toluenesulfonic acid monohydrate in 30 ml of benzene was refluxed for 140 hours in a vessel equipped with a Dean & Stark water separator. Ethyl acetate was added to the reaction mixture. The resultant mixture was washed successively with a saturated aqueous solution of sodium hydrogencarbonate, water and a saturated aqueous solution of sodium chloride, dried over anhydrous sodium sulfate, and then concentrated under reduced pressure. The residue was purified by chromatography on a silica gel column (eluent: ethyl acetate:hexane=1:2) and then recrystallized from acetonitrile, whereby 1.00 g of the title compound was obtained (yield: 37%).

EXAMPLE 95

Synthesis of 6-chloro-3,4-dihydro-2H-1,2-benzothiazin-4-one 1,1-dioxide ethylene acetal (Compound No. 95)

A solution of 4.70 g (17 mmol) of Compound No. 89, 5.30 g (85 mmol) of ethylene glycol and 323 mg (1.7 mmol) of p-toluenesulfonic acid monohydrate in 50 ml of benzene was refluxed in a vessel equipped with a Dean & Stark water separator. One hundred and forty-four (144) hours later, 930 mg (15 mmol) of ethylene glycol were added, followed by further reflux for 20 hours. Post-treatments were conducted as in Example 94. The residue was recrystallized from ethyl acetate-hexane, whereby 2.07 g of the title compound were obtained (yield: 44%).

EXAMPLE 96

Synthesis of 7-methoxy-3,4-dihydro-2H-1,2-benzothiazin-4-one 1,1-dioxide ethylene acetal (Compound No. 96)

A solution of 1.70 g (6.3 mmol) of Compound No. 90, 2.00 g (32 mmol) of ethylene glycol and 60 mg (0.31 mmol)

of p-toluenesulfonic acid monohydrate in 15 ml of benzene was refluxed in a vessel equipped with a Dean & Stark water separator. One hundred and forty-four (144) hours later, 465 mg (7.5 mmol) of ethylene glycol were added, followed by further reflux for 20 hours. Post-treatments were conducted as in Example 94. The residue was purified by chromatography on a silica gel column (eluent: methylene chloride: ethyl acetate=40:1), whereby 314 mg of the title compound were obtained (yield: 18%).

EXAMPLE 97

Synthesis of 7-chloro-3,4-dihydro-2H-1,2-benzothiazin-4-one 1,1-dioxide ethylene acetal (Compound No. 97)

A solution of 5.48 g (20 mmol) of Compound No. 91, 6.2 g (100 mmol) of ethylene glycol and 125 mg (0.67 mmol) of p-toluenesulfonic acid monohydrate in 50 ml of benzene was refluxed in a vessel equipped with a Dean & Stark water separator. Two hundred and forty (240) hours later, 2.25 g (37.5 mmol) of ethylene glycol were added, followed by further reflux for 20 hours. Post-treatments and purification were conducted as in Example 96, whereby 1.77 g of the title compound were obtained (yield: 32%).

EXAMPLE 98

Synthesis of 5-chloro-3,4-dihydro-2H-1,2-benzothiazin-4-one 1,1-dioxide (Compound No. 98)

3 N hydrochloric acid (10 ml, 30 mmol) was added to a suspension of 414 mg (1.5 mmol) of Compound No. 93 in 10 ml of methanol, followed by reflux for 70 minutes. The reaction mixture was concentrated under reduced pressure and precipitated crystals were collected by filtration. Those crystals were dissolved in ethyl acetate. The resulting solution was washed with a saturated aqueous solution of sodium chloride, dried over anhydrous sodium sulfate and then concentrated under reduced pressure, whereby 362 mg of the title compound were obtained (yield: 94%).

EXAMPLE 99

Synthesis of 5-chloro-3,4-dihydro-2H-1,2-benzothiazine-4-spiro-2'-(1',3'-dithiolane) 1,1-dioxide (Compound No. 99)

Boron trifluoride-ether complex (62 µl, 0.5 mmol) was added under ice cooling and stirring to a suspension of 232 mg (1 mmol) of Compound No. 98 and 252 µl (3 mmol) of 1,2-ethanedithiol in 5 ml of methylene chloride. The resultant mixture was stirred at 0° C. for 70 minutes and then at room temperature. Twenty-four (24) hours later, 31 µl (0.25 mmol) of boron trifluoride-ether complex were added and seven (7) hours later, 63 µl (0.75 mmol) of 1,2-ethanedithiol and 31 µl (0.25 mmol) of boron trifluoride were added further, followed by stirring for 65 hours.

An aqueous solution of potassium carbonate was added to the reaction mixture, and the mixture so obtained was extracted twice with methylene chloride. Organic layers were washed with a saturated aqueous solution of sodium chloride, dried over anhydrous sodium sulfate, and then concentrated under reduced pressure. The residue was purified by chromatography on a silica gel column (eluent: methylene chloride: methanol=30:1), whereby 223 mg of the title compound were obtained (yield: 72%).

EXAMPLE 100

Synthesis of 2-(2-chloroethyl)-5-methoxy-3,4-dihydro-2H-1,2-benzothiazin-4-one 1,1-dioxide ethylene acetal (Compound No. 100)

A solution of 190 mg (0.7 mmol) of Compound No. 92 in 5 ml of DMF was added under ice cooling and stirring to a suspension of 31 mg (0.77 mmol) of 60% sodium hydride in 5 ml of DMF. After the reaction mixture was stirred at 0° C. for 1 hour and then at room temperature for 1 hour, the reaction mixture was ice-cooled. A solution of 201 mg (1.4 mmol) of 1-bromo-2-chloroethane in 5 ml of DMF was then added, followed by stirring at room temperature for 16 hours.

The reaction mixture was concentrated under reduced pressure and 50 ml of a 5% aqueous solution of citric acid were added to the residue. The resultant mixture was extracted three times with methylene chloride. Organic layers were washed successively with water and a saturated aqueous solution of sodium chloride, dried over anhydrous sodium sulfate, and then concentrated under reduced pressure. The residue was purified by chromatography on a silica gel column (eluent: ethyl acetate:hexane=1:1), whereby 213 mg of the title compound were obtained (yield: 91%).

EXAMPLE 101

Synthesis of 2-(3-chloropropyl)-5-methoxy-3,4-dihydro-2H-1,2-benzothiazin-4-one 1,1-dioxide ethylene acetal (Compound No. 101)

A suspension of 813 mg (3 mmol) of Compound No. 92, 945 mg (6 mmol) of 1-bromo-3-chloropropane and 828 mg (6 mmol) of potassium carbonate in 15 ml of DMF was stirred at room temperature for 15 hours. The reaction mixture was filtered and the filtrate was concentrated under reduced pressure.

Ethyl acetate was added to the residue. The mixture so obtained was washed successively with a saturated aqueous solution of sodium hydrogencarbonate and a saturated solution of sodium chloride, dried over anhydrous magnesium sulfate, and then concentrated under reduced pressure. The residue was purified by chromatography on a silica gel column (eluent: methylene chloride:ethyl acetate=50:1), whereby 1.03 g of the title compound were obtained (yield: 98%).

EXAMPLE 102

Synthesis of 5-chloro-2-(3-chloropropyl)-3,4-dihydro-2H-1,2-benzothiazin-4-one 1,1-dioxide ethylene acetal (Compound No. 102)

A suspension of 551 mg (2 mmol) of Compound No. 93, 630 mg (4 mmol) of 1-bromo-3-chloropropane and 552 mg (4 mmol) of potassium carbonate in 10 ml of DMF was stirred at room temperature for 20 hours. Post-treatments and purification were conducted as in Example 101, whereby 698 mg of the title compound were obtained (yield: 99%).

EXAMPLE 103

Synthesis of 2-(3-chloropropyl)-6-methoxy-3,4-dihydro-2H-1,2-benzothiazin-4-one 1,1-dioxide ethylene acetal (Compound No. 103)

A suspension of 542 mg (2 mmol) of Compound No. 94, 471 mg (3 mmol) of 1-bromo-3-chloropropane and 552 mg (4 mmol) of potassium carbonate in 20 ml of acetone was refluxed for 8 hours. The reaction mixture was filtered and the filtrate was concentrated under reduced pressure.

Ethyl acetate was added to the residue. The mixture so obtained was washed successively with a saturated aqueous solution of sodium hydrogencarbonate and a saturated solution of sodium chloride, dried over anhydrous magnesium sulfate, and then concentrated under reduced pressure. The residue was purified by chromatography on a silica gel column (eluent: ethyl acetate:hexane=1:2), whereby 578 mg of the title compound were obtained (yield: 83%).

EXAMPLE 104

Synthesis of 6-chloro-2-(3-chloropropyl)-3,4-dihydro-2H-1,2-benzothiazin-4-one 1,1-dioxide ethylene acetal (Compound No. 104)

A suspension of 550 mg (2 mmol) of Compound No. 95, 471 mg (3 mmol) of 1-bromo-3-chloropropane and 552 mg (4 mmol) of potassium carbonate in 20 ml of acetone was refluxed for 14 hours. Post-treatments and purification were conducted as in Example 103, whereby 735 mg of the title compound were obtained (yield: 99%).

EXAMPLE 105

Synthesis of 2-(3-chloropropyl)-7-methoxy-3,4-dihydro-2H-1,2-benzothiazin-4-one 1,1-dioxide ethylene acetal (Compound No. 105)

A suspension of 271 mg (1 mmol) of Compound No. 96, 236 mg (1.5 mmol) of 1-bromo-3-chloropropane and 276 mg (2 mmol) of potassium carbonate in 10 ml of acetone was refluxed for 10 hours. Post-treatments and purification were conducted as in Example 103, whereby 321 mg of the title compound were obtained (yield: 92%).

EXAMPLE 106

Synthesis of 7-chloro-2-(3-chloropropyl)-3,4-dihydro-2H-1,2-benzothiazin-4-one 1,1-dioxide ethylene acetal (Compound No. 106)

A suspension of 825 mg (3 mmol) of Compound No. 97, 707 mg (4.5 mmol) of 1-bromo-3-chloropropane and 828 mg (6 mmol) of potassium carbonate in 30 ml of acetone was refluxed for 7 hours. Post-treatments were conducted as in Example 103 and the residue was purified by chromatography on a silica gel column (eluent: ethyl acetate:hexane=1:1), whereby 1.08 g of the title compound were obtained (yield: 99%).

EXAMPLE 107

Synthesis of 2-(3-chloropropyl)-5-methoxy-3,4-dihydro-2H-1,2-benzothiazin-4-one 1,1-dioxide (Compound No. 107)

4 N hydrochloric acid (4 ml, 16 mmol) was added to a solution of 430 mg (1.24 mmol) of Compound No. 101 in 4 ml of methanol, followed by reflux for 2 hours. The reaction mixture was concentrated under reduced pressure. The residue was added with ethyl acetate. The mixture so obtained was washed successively with a saturated aqueous solution of sodium hydrogencarbonate and a saturated solution of sodium chloride, dried over anhydrous magnesium sulfate, and then concentrated under reduced pressure. The residue was purified by chromatography on a silica gel column (eluent: methylene chloride:ethyl acetate=30:1), whereby 392 mg of the title compound were obtained (yield: 99%).

EXAMPLE 108

Synthesis of 2-(3-chloropropyl)-5-methoxy-3,4-dihydro-2H-1,2-benzothiazine-4-spiro-2'-(1',3'-dithiolane) 1,1-dioxide (Compound No. 108)

Boron trifluoride-ether complex (0.06 ml, 0.45 mmol) was added under ice cooling and stirring to a solution of 350 mg (1.15 mmol) of Compound No. 107 and 0.12 ml (1.4 mmol) of ethanedithiol in 4.5 ml of methylene chloride. The resultant mixture was stirred at 0° C. for 1 hour and then at room temperature for 12 hours.

Ethyl acetate was added to the reaction mixture. The mixture so obtained was washed successively with a saturated aqueous solution of sodium hydrogencarbonate and a saturated solution of sodium chloride, dried over anhydrous magnesium sulfate, and then concentrated under reduced pressure. The residue was purified by chromatography on a silica gel column (eluent: ethyl acetate:hexane=1:2) and then recrystallized from ethyl acetate-hexane, whereby 383 mg of the title compound were obtained (yield: 87%).

EXAMPLE 109

Synthesis of 2-[2-[4-(4-fluorophenyl)piperazin-1-yl]ethyl]-5-methoxy-3,4-dihydro-2H-1,2-benzothiazin-4-one 1,1-dioxide ethylene acetal (Compound No. 109)

A suspension of 100 mg (0.3 mmol) of Compound No. 100, 108 mg (0.6 mmol) of 1-(4-fluorophenyl)piperazine and 90 mg (0.6 mmol) of sodium iodide in 15 ml of acetonitrile was refluxed for 24 hours.

The reaction mixture was concentrated under reduced pressure and 50 ml of a half-saturated aqueous solution of potassium carbonate were added to the residue. The mixture so obtained was extracted three times with ethyl acetate. Organic layers were washed successively with water and a saturated aqueous solution of sodium chloride, dried over anhydrous sodium sulfate, and then concentrated under reduced pressure. The residue was purified by chromatography on a silica gel column (eluent: ethyl acetate:hexane=3:1), whereby 106 mg of the title compound were obtained (yield: 74%).

EXAMPLE 110

Synthesis of 2-[3-[4-(4-fluorophenyl)piperazin-1-yl]propyl]-5-methoxy-3,4-dihydro-2H-1,2-benzothiazin-4-one 1,1-dioxide ethylene acetal (Compound No. 110)

A suspension of 173 mg (0.5 mmol) of Compound No. 101, 135 mg (0.75 mmol) of 1-(4-fluorophenyl)piperazine, 84 mg (1 mmol) of sodium hydrogencarbonate and 150 mg (1 mmol) of sodium iodide in 10 ml of acetonitrile was refluxed for 18 hours.

The reaction mixture was concentrated under reduced pressure and a saturated aqueous solution of sodium hydrogencarbonate was added to the residue. The mixture so obtained was extracted twice with methylene chloride. Organic layers were dried over anhydrous magnesium sulfate and then concentrated under reduced pressure. The residue was purified by chromatography on a silica gel column (eluent: methylene chloride: methanol=30:1), whereby 243 mg of the title compound were obtained (yield: 98%).

EXAMPLE 111

Synthesis of 2-[3-[4-(4-hydroxyphenyl)piperazin-1-yl]propyl]-5-methoxy-3,4-dihydro-2H-1,2-benzothiazin-4-one 1,1-dioxide ethylene acetal (Compound No. 111)

A suspension of 173 mg (0.5 mmol) of Compound No. 101, 194 mg (0.75 mmol) of 1-(4-hydroxyphenyl)piperazine hydrobromide, 168 mg (2 mmol) of sodium hydrogencarbonate and 150 mg (1 mmol) of sodium iodide in 10 ml of acetonitrile was refluxed for 20 hours.

Post-treatments were conducted as in Example 110 and the residue was purified by chromatography on a silica gel column (eluent: methylene chloride: methanol 20:1), whereby 191 mg of the title compound were obtained (yield: 78%).

EXAMPLE 112

Synthesis of 2-[3-[4-(4-fluorobenzoyl)piperidino]-propyl]-5-methoxy-3,4-dihydro-2H-1,2-benzothiazin-4-one 1,1-dioxide ethylene acetal (Compound No. 112)

A suspension of 173 mg (0.5 mmol) of Compound No. 101, 183 mg (0.75 mmol) of 4-(4-fluorobenzoyl)piperadine hydrochloride, 168 mg (2 mmol) of sodium hydrogencarbonate and 150 mg (1 mmol) of sodium iodide in 10 ml of acetonitrile was refluxed for 18 hours. Post-treatments and purification were conducted as in Example 110, whereby 247 mg of the title compound were obtained (yield: 95%).

EXAMPLE 113

Synthesis of 5-chloro-2-[3-[4-(4-fluorophenyl) piperazin-1-yl]propyl]-3,4-dihydro-2H-1,2-benzothiazin-4-one 1,1-dioxide ethylene acetal (Compound No. 113)

A suspension of 141 mg (0.4 mmol) of Compound No. 102, 108 mg (0.6 mmol) of 1-(4-fluorophenyl)piperazine, 67 mg (0.8 mmol) of sodium hydrogencarbonate and 120 mg (0.8 mmol) of sodium iodide in 8 ml of acetonitrile was refluxed for 16 hours. Post-treatments and purification were conducted as in Example 110, whereby 196 mg of the title compound were obtained (yield: 98%).

EXAMPLE 114

Synthesis of 5-chloro-2-[3-[4-(4-hydroxyphenyl) piperazin-1-yl]propyl]-3,4-dihydro-2H-1,2-benzothiazin-4-one 1,1-dioxide ethylene acetal (Compound No. 114)

A suspension of 141 mg (0.4 mmol) of Compound No. 102, 155 mg (0.6 mmol) of 1-(4-hydroxyphenyl)piperazine hydrobromide, 134 mg (1.6 mmol) of sodium hydrogencarbonate and 120 mg (0.8 mmol) of sodium iodide in 8 ml of acetonitrile was refluxed for 17 hours. Post-treatments and purification were conducted as in Example 111, whereby 181 mg of the title compound were obtained (yield: 93%).

EXAMPLE 115

Synthesis of 2-[3-[4-(4-fluorophenyl)piperazin-1-yl] propyl]-6-methoxy-3,4-dihydro-2H-1,2-benzothiazin-4-one 1,1-dioxide ethylene acetal (Compound No. 115)

A suspension of 173 mg (0.5 mmol) of Compound No. 103, 135 mg (0.75 mmol) of 1-(4-fluorophenyl)piperazine, 84 mg (1 mmol) of sodium hydrogencarbonate and 150 mg (1 mmol) of sodium iodide in 10 ml of acetonitrile was refluxed for 15 hours. Post-treatments and purification were conducted as in Example 111, whereby 229 mg of the title compound were obtained (yield: 93%).

EXAMPLE 116

Synthesis of 2-[3-[4-(4-fluorobenzoyl)piperidino]-propyl]-6-methoxy-3,4-dihydro-2H-1,2-benzothiazin-4-one 1,1-dioxide ethylene acetal (Compound No. 116)

A suspension of 173 mg (0.5 mmol) of Compound No. 103, 182 mg (0.75 mmol) of 4-(4-fluorobenzoyl)piperidine hydrochloride, 168 mg (2 mmol) of sodium hydrogencarbonate and 150 mg (1 mmol) of sodium iodide in 10 ml of acetonitrile was refluxed for 15 hours. Post-treatments were conducted as in Example 110 and the residue was purified by chromatography on a silica gel column (eluent: methylene chloride: methanol=15:1), whereby 241 mg of the title compound were obtained (yield: 93%).

EXAMPLE 117

Synthesis of 6-chloro-2-[3-[4-(4-fluorophenyl) piperazin-1-yl]propyl]-3,4-dihydro-2H-1,2-benzothiazin-4-one 1,1-dioxide ethylene acetal (Compound No. 117)

A suspension of 176 mg (0.5 mmol) of Compound No. 104, 135 mg (0.75 mmol) of 1-(4-fluorophenyl)piperazine, 84 mg (1 mmol) of sodium hydrogencarbonate and 150 mg (1 mmol) of sodium iodide in 10 ml of acetonitrile was refluxed for 15 hours. Post-treatments and purification were conducted as in Example 111, whereby 206 mg of the title compound were obtained (yield: 83%).

EXAMPLE 118

Synthesis of 6-chloro-2-[3-[4-(4-fluorobenzoyl) piperidino]propyl]-3,4-dihydro-2H-1,2-benzothiazin-4-one 1,1-dioxide ethylene acetal (Compound No. 118)

A suspension of 176 mg (0.5 mmol) of Compound No. 104, 182 mg (0.75 mmol) of 4-(4-fluorobenzoyl)piperidine hydrochloride, 168 mg (2 mmol) of sodium hydrogencarbonate and 150 mg (1 mmol) of sodium iodide in 10 ml of acetonitrile was refluxed for 15 hours. Post-treatments and purification were conducted as in Example 111, whereby 211 mg of the title compound were obtained (yield: 80%).

EXAMPLE 119

Synthesis of 2-[3-[4-(4-fluorophenyl)piperazin-1-yl] propyl]-7-methoxy-3,4-dihydro-2H-1,2-benzothiazin-4-one 1,1-dioxide ethylene acetal (Compound No. 119)

A suspension of 104 mg (0.3 mmol) of Compound No. 105, 81 mg (0.45 mmol) of 1-(4-fluorophenyl)piperazine, 51 mg (0.6 mmol) of sodium hydrogencarbonate and 90 mg (0.6 mmol) of sodium iodide in 6 ml of acetonitrile was refluxed for 18 hours. Post-treatments and purification were conducted as in Example 110, whereby 138 mg of the title compound were obtained (yield: 94%).

EXAMPLE 120

Synthesis of 2-[3-[4-(4-fluorobenzoyl)piperidino]-propyl]-7-methoxy-3,4-dihydro-2H-1,2-benzothiazin-4-one 1,1-dioxide ethylene acetal (Compound No. 120)

A suspension of 104 mg (0.3 mmol) of Compound No. 105, 109 mg (0.45 mmol) of 4-(4-fluorobenzoyl)piperidine hydrochloride, 101 mg (1.2 mmol) of sodium hydrogencarbonate and 90 mg (0.6 mmol) of sodium iodide in 6 ml of acetonitrile was refluxed for 18 hours. Post-treatments and purification were conducted as in Example 111, whereby 140 mg of the title compound were obtained (yield: 90%).

EXAMPLE 121

Synthesis of 7-chloro-2-[3-[4-(4-fluorophenyl) piperazin-1-yl]propyl]-3,4-dihydro-2H-1,2-benzothiazin-4-one 1,1-dioxide ethylene acetal (Compound No. 121)

A suspension of 160 mg (0.45 mmol) of Compound No. 106, 135 mg (0.75 mmol) of 1-(4-fluorophenyl)piperazine, 84 mg (1 mmol) of sodium hydrogencarbonate and 150 mg (1 mmol) of sodium iodide in 10 ml of acetonitrile was refluxed for 15 hours. Post-treatments and purification were conducted as in Example 110, whereby 194 mg of the title compound were obtained (yield: 78%).

EXAMPLE 122

Synthesis of 7-chloro-2-[3-[4-(4-fluorobenzoyl) piperidino]propyl]-3,4-dihydro-2H-1,2-benzothiazin-4-one 1,1-dioxide ethylene acetal (Compound No. 122)

A suspension of 160 mg (0.45 mmol) of Compound No. 106, 182 mg (0.75 mmol) of 4-(4-fluorobenzoyl)piperidine hydrochloride, 168 mg (2 mmol) of sodium hydrogencarbonate and 150 mg (1 mmol) of sodium iodide in 10 ml of acetonitrile was refluxed for 15 hours. Post-treatments and purification were conducted as in Example 111, whereby 179 mg of the title compound were obtained (yield: 68%).

EXAMPLE 123

Synthesis of 2-[3-[4-(4-fluorophenyl)piperazin-1-yl] propyl]-5-methoxy-3,4-dihydro-2H-1,2-benzothiazine-4-spiro-2'-(1',3'-dithiolane) 1,1-dioxide (Compound No. 123)

A suspension of 190 mg (0.5 mmol) of Compound No. 108, 135 mg (0.75 mmol) of 1-(4-fluorophenyl)piperazine, 84 mg (1 mmol) of sodium hydrogencarbonate and 150 mg (1 mmol) of sodium iodide in 10 ml of acetonitrile was refluxed for 18 hours. Post-treatments and purification were conducted as in Example 110, whereby 223 mg of the title compound were obtained (yield: 90%).

EXAMPLE 124

Synthesis of 5-chloro-2-[3-[4-(4-fluorophenyl) piperazin-1-yl]propyl]-3,4-dihydro-2H-1,2-benzothiazine-4-spiro-2'-(1',3'-dithiolane) 1,1-dioxide (Compound No. 124)

A solution of 154 mg (0.5 mmol) of Compound No. 99 in 1.5 ml of DMF was added under ice cooling and stirring to a suspension of 22 mg (0.55 mmol) of 60%-sodium hydride in 3 ml of DMF, followed by stirring at 0° C. for 30 minutes and then at room temperature for 30 minutes. The reaction mixture was then cooled down to 0° C., to which a solution of 193 mg (0.75 mmol) of 1-(3-chloropropyl)-4-(4-fluorophenyl)piperazine in 1.5 ml of DMF was added. The resulting mixture was stirred at room temperature for 24 hours.

A 3:1 (by volume) mixed solvent of ethyl acetate and benzene was added to the reaction mixture. An organic layer was washed successively with a half-saturated aqueous solution of sodium hydrogencarbonate, water and a saturated solution of sodium chloride, dried over anhydrous sodium sulfate, and then concentrated under reduced pressure. The residue was purified by chromatography on a silica gel column (eluent: ethyl acetate:hexane=1:2→1:1→2:1), whereby 102 mg of the title compound were obtained (yield: 39%).

The structural formulas and physical properties of the compounds obtained in the above examples are summarized in Table 1.

TABLE 1

| Comp'd No. | Structural formula | Property Melting point (recrystallization solvent) | NMR (δ ppm)*<br>( ): observation frequency | IR (cm$^{-1}$)<br>( ): measuring method |
|---|---|---|---|---|
| 1 | (structure) | Colorless prism crystals 147.0–148.5° C. (ethyl acetate-hexane) | (270 MHz) 1.58(1H, d.quint, J=2.3Hz, 13.9Hz), 2.27(1H, m), 3.96–4.20(6H, m), 5.07 (1H, t, J=7.6Hz), 7.49(1H, dt, J= 1.3Hz, 7.9Hz), 7.59(1H, dt, J=1.3Hz, 7.9Hz), 7.76(1H, dd, J=1.3Hz, 7.9Hz), 7.87(1H, dd, J=1.3Hz, 7.9Hz) | (KBr) 3253, 2965, 2887, 1427, 1322, 1175, 1144, 1076, 1026, 953, 815, 764 |
| 2 | (structure) | Colorless prism crystals 142.5–143.0° C. (ethyl acetate-hexane) | (270 MHz) 1.33(3H, d, J=5.9Hz), 1.40(3H, d, J=5.9Hz), 3.74(2H, dd, J=1.3Hz, 7.9Hz), 3.79–3.97(2H, m), 5.22 (1H, t, J=7.9Hz), 7.48–7.62(3H, m), 7.77(1H, d, J=7.9Hz) | (KBr) 3245, 2977, 1426, 1382, 1314, 1256, 1158, 1077, 944, 892, 820, 698 |
| 3 | (structure) | Colorless prism crystals 169.5–171.5° C. (ethyl acetate-hexane) | (270 MHz) 3.29(1H, m), 3.41(1H, m), 3.92(2H, m), 4.21(1H, m), 4.52(1H, m), 5.22(1H, t, J=7.3Hz), 7.49(1H, m), 7.58(1H, m), 7.77(1H, m), 7.80(1H, m) | (KBr) 3295, 1405, 1318, 1167, 1137, 1052, 1015, 824, 762, 702 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 4 | (spiro dithiolane fused benzisothiazoline dioxide) | Colorless powdery crystals 231.5–232.0° C. (chloroform-hexane) | (270 MHz) 3.45(2H, m), 3.64(2H, m), 3.96(2H, d, J=7.9Hz), 5.39(1H, t, J=7.9Hz), 7.42(1H, dt, J=1.3Hz, 7.9Hz), 7.54(1H, dt, J=1.3Hz, 7.9Hz), 7.74(1H, dd, J=1.3Hz, 7.9Hz), 8.04(1H, dd, J=1.3Hz, 7.9Hz) | (KBr) 3263, 1402, 1318, 1164, 1131, 853, 751, 708, 668 |
| 5 | (spiro dithiane fused benzisothiazoline dioxide) | Colorless prism crystals 231.0–232.5° C. (acetonitrile) | (400 MHz) 2.01(1H, m), 2.23(1H, m), 2.78(2H, dt, J=3.7Hz, 14.7Hz), 3.11(2H, dt, J=2.5Hz, 14.7Hz), 4.24(2H, d, J=7.7Hz), 5.29(1H, t, J=7.7Hz), 7.47(1H, dt, J=1.4Hz, 7.8Hz), 7.57(1H, dt, J=1.4Hz, 7.8Hz), 7.82(1H, dd, J=1.3Hz, 7.8Hz), 8.09(1H, dd, J=0.9Hz, 7.8Hz) | (KBr) 3274, 1471, 1452, 1428, 1418, 1390, 1321, 1276, 1176, 1133, 1085, 1058, 998, 890, 852, 818, 779, 754, 709, 676 |
| 6 | (bis-ethylthio substituted) | Colorless needle crystals 86.5–87.0° C. (ethyl acetate-hexane) | (270 MHz) 1.18(6H, t, J=7.6Hz), 2.40–2.67 (4H, m), 4.01(2H, d, J=7.9Hz), 5.49 (1H, t, J=7.9Hz), 7.46(1H, dt, J=1.3Hz, 7.9Hz), 7.58(1H, dt, J=1.3Hz, 7.9Hz), 7.82(1H, dd, J=1.3Hz, 7.9Hz), 8.03 (1H, dd, J=1.3Hz, 7.9Hz) | (KBr) 3281, 1405, 1325, 1170, 1068, 840, 753, 711, 667 |
| 7 | (bis-methoxy substituted) | Colorless prism crystals 161.0–162.0° C. (ethyl acetate-hexane) | (270 MHz) 3.25(6H, s), 3.82(2H, d, J=7.9Hz), 5.11(1H, br.d), 7.51–7.60(2H, m), 7.72(1H, m), 7.83(1H, m) | (KBr) 3256, 2976, 1446, 1328, 1225, 1152, 1085, 1040, 969, 898, 821, 777, 693 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 8 | (benzothiazine with OCH₃, NH, S O₂) | Colorless prism crystals 85.0–86.0° C. (ethyl acetate-hexane) | (270 MHz) 3.79(3H, s), 5.96(1H, br.s), 6.03 (1H, d, J=2.6Hz), 7.54(1H, dt, J=1.3Hz, 7.3Hz), 7.64(1H, dt, J=1.3Hz, 7.9Hz), 7.83(1H, m) | (KBr) 3300–3100, 1630, 1560, 1400, 1310, 1250, 1150, 1070, 990, 870, 760, 670 |
| 9 | (benzothiazine with OCH₃, NH, S O₂) | Colorless needle crystals 80.0–81.0° C. (ethyl acetate-hexane) | (270 MHz) 3.43(3H, s), 3.78(1H, m), 4.01(1H, m), 4.10(1H, m), 5.05(1H, br), 7.38(1H, dd, J=2.0Hz, 7.3Hz), 7.53–7.56(2H, m), 7.87(1H, dd, J=2.0Hz, 7.3Hz) | (KBr) 3258, 2823, 1410, 1316, 1173, 1064, 884, 810, 709 |
| 10 | (spiro dioxolane benzothiazine with N-(CH₂)₂Cl) | Colorless prism crystals 126.5–128.0° C. (ethyl acetate-hexane) | (270 MHz) 3.60–3.86(4H, m), 3.98(2H, s), 4.09–4.23(2H, m), 4.23–4.38 (2H, m), 7.41–7.67(3H, m), 7.77(1H, d, J=7.9Hz) | (KBr) 1440, 1327, 1262, 1154, 1091, 1051, 1031, 994, 945, 895, 847, 771, 754, 687 |
| 11 | (spiro dioxolane benzothiazine with N-(CH₂)₃Cl) | Colorless prism crystals 72.5–74.0° C. (ethyl acetate-hexane) | (270 MHz) 2.11(2H, m), 3.62(2H, t, J=6.6Hz), 3.72(2H, t, J=5.9Hz), 3.91(2H, s), 4.17(2H, m), 4.29(2H, m), 7.46–7.64(3H, m), 7.79(1H, m) | (KBr) 2957, 1460, 1330, 1228, 1174, 1149, 1051, 995, 950, 937, 799, 776 |

TABLE 1-continued

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 12 | (spiro-dioxolane benzo sultam with N-(CH$_2$)$_4$Cl) | Colorless oil | (270 MHz) 1.69–2.00(4H, m), 3.47(2H, t, J=5.9Hz), 3.60(2H, t, J=5.9Hz), 3.87(2H, s), 4.07–4.24(2H, m), 4.24–4.38(2H, m), 7.40–7.67 (3H, m), 7.78(1H, m) | (film) 1331, 1155, 1052, 948, 764, 691 |
| 13 | (spiro-dithiolane benzo sultam with N-(CH$_2$)$_2$Cl) | Colorless prism crystals 120.5–121.0° C. (ethyl acetate-hexane) | (400 MHz) 3.49(2H, m), 3.64(2H, m), 3.76(2H, t, J=6.6Hz), 3.92(2H, t, J=6.6Hz), 4.21(2H, s), 7.40(1H, m), 7.52(1H, m), 7.75(1H, dd, J=1.2Hz, 7.9Hz), 7.95(1H, d, J=8.2Hz) | (KBr) 2931, 1319, 1163, 1089, 942, 776, 757, 652 |
| 14 | (spiro-dithiolane benzo sultam with N-(CH$_2$)$_3$Cl) | Colorless prism crystals 137.0–137.5° C. (ethyl acetate-hexane) | (400 MHz) 2.17(2H, quint, J=6.3Hz), 3.48 (2H, m), 3.64(2H, m), 3.70(2H, t, J=6.3Hz), 3.75(2H, t, J=6.3Hz), 4.10(2H, s), 7.40(1H, dt, J=0.8 Hz, 7.9Hz), 7.52(1H, dt, J=1.2Hz, 7.9Hz), 7.76(1H, dd, J=1.2Hz, 7.9 Hz), 7.95(1H, dd, J=0.8Hz, 7.9Hz) | (KBr) 2920, 1471, 1430, 1350, 1296, 1153, 953, 790, 768, 746, 654 |
| 15 | (spiro-dithiane benzo sultam with N-(CH$_2$)$_2$Cl) | Colorless prism crystals 198.0–200.0° C. (ethyl acetate-hexane) | (400 MHz) 2.03(1H, m), 2.26(1H, m), 2.83(2H, dt, J=3.8Hz, 14.8Hz), 3.15(2H, ddd, J=2.5Hz, 12.7Hz, 14.8Hz), 3.75(2H, t, J=6.2Hz), 3.94(2H, t, J=6.2Hz), 4.62(2H, s), 7.46(1H, dt, J=1.3Hz, 7.8Hz), 7.56(1H, dt, J=1.3Hz, 7.8 Hz), 7.82(1H, dd, J=1.3Hz, 7.8Hz), 8.09(1H, dd, J=1.3Hz, 7.8Hz) | (KBr) 3630, 2907, 1474, 1442, 1425, 1319, 1228, 1165, 1133, 1094, 952, 912, 885, 784, 758, 720, 696, 678 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 16 | (structure: spiro dithiane benzothiazine-SO₂-N-(CH₂)₃Cl) | Colorless prism crystals 161.0–163.0° C. (ethyl acetate-hexane) | (400 MHz) 2.04(1H, m), 2.14(2H, quint, J=6.2Hz), 2.23 (1H, m), 2.82(2H, dt, J=3.7Hz, 14.7Hz), 3.17(2H, ddd, J=2.4Hz, 12.7Hz, 14.7Hz), 3.75(2H, t, J=6.2Hz), 3.79(2H, t, J=6.2Hz), 4.49(2H, s), 7.45(1H, dt, J=1.0Hz, 7.8Hz), 7.55(1H, dt, J=1.3Hz, 7.8Hz), 7.85(1H, dd, J=1.3Hz, 7.8Hz), 8.07(1H, dd, J=1.0Hz, 7.8Hz) | (KBr) 2902, 1438, 1424, 1300, 1241, 1163, 1136, 1076, 962, 884, 778, 754, 722, 700, 674, 656 |
| 17 | (structure: benzothiazine with C(OCH₃)(CH₂OCH₃), N-(CH₂)₃Br) | Colorless oil | (270 MHz) 2.21(2H, m), 3.27(6H, s), 3.58 (2H, t, J=6.6Hz), 3.63(2H, t, J=6.6Hz), 3.99(2H, s), 7.49–7.60 (2H, m), 7.69(1H, dd, J=2.0Hz, 7.3Hz), 7.85(1H, dd, J=2.0Hz, 7.3Hz) | (film) 2947, 1459, 1337, 1142, 1064, 986, 936, 768, 688 |
| 18 | (structure: 4-OCH₃ benzothiazine, N-(CH₂)₃Br) | Colorless oil | (270 MHz) 2.17(2H, m), 3.39(2H, t, J=6.6Hz), 3.77(2H, t, J=6.6Hz), 3.82(3H, s), 6.06(1H, s), 7.55(1H, dt, J=1.3Hz, 7.9Hz), 7.64(1H, dt, J=1.3Hz, 7.9Hz), 7.81(1H, dd, J=1.3Hz, 7.9Hz), 7.85(1H, dd, J=1.3Hz, 7.9Hz) | (film) 1630, 1440, 1380, 1340, 1270, 1230, 1170, 1130, 1070, 770 |
| 19 | (structure: 4-OCH₃ dihydrobenzothiazine, N-(CH₂)₃Br) | Colorless oil | (270 MHz) 2.19(2H, m), 3.43–3.62(4H, m), 3.56(3H, s), 3.88(1H, dd, J=4.0Hz, 15.2Hz), 4.15(1H, dd, J=4.0Hz, 15.2Hz), 4.35(1H, t, J=4.0Hz), 7.46–7.61(3H, m), 7.83(1H, dd, J=1.3Hz, 7.9Hz) | (film) 1460, 1450, 1340, 1170, 1130, 1070, 760, 700 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 20 | (benzothiazine with OCH₃, N-(CH₂)₃Cl, SO₂) | Colorless oil | (270 MHz) 2.11(2H, m), 3.51(2H, m), 3.59(3H, s), 3.71(2H, m), 3.87(1H, dd, J=4.0Hz, 15.2Hz), 4.14(1H, dd, J=4.0Hz, 15.2Hz), 4.35(1H, t, J=4.0Hz), 7.45–7.60 (3H, m), 7.83(1H, dd, J=1.3Hz, 7.9Hz) | (film) 2937, 2828, 1445, 1336, 1170, 1133, 1071, 946, 761, 703 |
| 21 | (benzothiazine with O=, N-(CH₂)₃Cl, SO₂) | Colorless prism crystals 76.5–78.0° C. (ethyl acetate-hexane) | (270 MHz) 2.08(2H, quint, J=6.6Hz), 3.36(2H, t, J=6.6Hz), 3.65(2H, t, J=6.6Hz), 4.46 (2H, s), 7.75(1H, ddd, J=1.3Hz, 7.3Hz, 7.6Hz), 7.83(1H, ddd, J=1.3Hz, 7.3Hz, 7.6Hz), 7.89(1H, dd, J=1.3Hz, 7.6Hz), 8.08(1H, dd, J=1.3Hz, 7.6Hz) | (KBr) 1698, 1588, 1341, 1281, 1235, 1175, 1120, 928, 759 |
| 22 | (benzothiazine with NOH=, N-(CH₂)₃Cl, SO₂) | Yellow oil | (270 MHz) 2.07(2H, quint, J=6.6Hz), 3.17 (2H, t, J=6.6Hz), 3.65(2H, t, J=6.6Hz), 4.71(2H, s), 7.51–7.69 (2H, m), 7.87(1H, m), 7.99(1H, m), 8.77(1H, s) | (film) 3422, 1341, 1173, 1131, 955, 759 |
| 23 | (benzothiazine with OH, N-(CH₂)₃Cl, SO₂) | Colorless oil | (270 MHz) 2.11(2H, quint, J=6.3Hz), 2.83 (1H, d, J=7.6Hz), 3.37–3.65(2H, m), 3.67(2H, t, J=6.3Hz), 3.74(1H, dd, J=5.3Hz, 14.5Hz), 4.02(1H, dd, J=6.6 Hz, 14.5Hz), 4.85(1H, m), 7.42–7.68 (3H, m), 7.90(1H, d, J=7.9Hz) | (film) 3484, 1444, 1323, 1168, 1132, 1059 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 24 | (structure: 4-OC₂H₅-substituted benzothiazine with N-(CH₂)₃Cl, S O₂) | Colorless oil | (270 MHz) 1.30(3H, t, J=7.3Hz), 2.11(2H, m), 3.51(2H, m), 3.60–3.90(5H, m), 4.14 (1H, dd, J=4.0Hz, 15.2Hz), 4.46 (1H, t, J=4.0Hz), 7.40–7.60(3H, m), 7.83(1H, dd, J=1.3Hz, 7.9Hz) | (film) 2975, 2875, 1446, 1337, 1172, 1071, 762, 706 |
| 25 | (structure: 4-OCH₂Ph-substituted benzothiazine with N-(CH₂)₃Cl, S O₂) | Colorless oil | (270 MHz) 2.08(2H, m), 3.52 (2H, quint, J=5.3Hz), 3.52 (2H, m), 3.69(2H, m), 3.88(1H, dd, J=4.0Hz, 15.2Hz), 4.13(1H, dd, J=4.0Hz, 15.2Hz), 4.57(1H, t, J=4.0Hz), 4.70(1H, d, J=11.9Hz), 4.79(1H, d, J=11.9Hz), 7.30–7.60 (8H, m), 7.83(1H, dd, J=2.0Hz, 7.9Hz) | (film) 1455, 1335, 1169 1133, 1067, 760, 702 |
| 26 | (structure: benzothiazine with double bond, N-(CH₂)₃Cl, S O₂) | Colorless oil | (400 MHz) 2.22(2H, m), 3.61(2H, t, J=6.1Hz), 3.93(2H, t, J=6.5Hz), 6.24(1H, d, J=7.9Hz), 6.63(1H, d, J=7.9Hz), 7.37(1H, d, J=7.8Hz), 7.47(1H, m), 7.58(1H, m), 7.91(1H, d, J=7.9Hz) | (film) 1621, 1477, 1442, 1332, 1174, 1133, 1069, 778, 752 |
| 27 | (structure: benzothiazine with N-(CH₂)₃Cl, S O₂) | Colorless oil | (400 MHz) 2.13(2H, m), 3.03(2H, t, J=6.3Hz), 3.35(2H, t, J=6.6Hz), 3.70(2H, t, J=6.1Hz), 3.92(2H, t, J=6.3Hz), 7.23(1H, d, J=7.7Hz), 7.37(1H, m), 7.46(1H, m), 7.83(1H, d, J=7.8Hz) | (film) 2963, 1479, 1446, 1317, 1161, 1069, 948, 856, 760, 710, 678 |

TABLE 1-continued

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 28 | [structure: spiro dioxolane benzothiazine-S,S-dioxide with N-(CH$_2$)$_3$-N-piperazine-phenyl] | Colorless needle crystals 113.0–115.0° C. (2-propanol-isopropyl ether) | (270 MHz) 1.86(2H, m), 2.51(2H, t, J=6.6Hz), 2.61(4H, m), 3.20(4H, m), 3.53(2H, t, J=6.6Hz), 3.92(2H, s), 4.07–4.21 (2H, m), 4.21–4.35(2H, m), 6.85(1H, t, J=7.3Hz), 6.93(2H, d, J=8.6Hz), 7.26(2H, dd, J=7.3Hz, 8.6Hz), 7.45–7.63(3H, m), 7.79(1H, m) | (KBr) 1597, 1499, 1326, 1158, 1052, 952 764, 755 |
| 29 | [structure: spiro dioxolane benzothiazine-S,S-dioxide with N-(CH$_2$)$_2$-N-piperazine-(4-fluorophenyl)] | Colorless prism crystals 130.0–131.5° C. (ethyl acetate-hexane) | (270 MHz) 2.50–2.80(6H, m), 3.10(4H, m), 3.61 (2H, t, J=6.6Hz), 4.02(2H, s), 4.07–4.23(2H, m), 4.23–4.38(2H, m), 6.77–7.04(4H, m), 7.40–7.65(3H, m), 7.79(1H, m) | (KBr) 2824, 1509, 1324, 1236, 1154, 1051, 947, 825, 755 |
| 30 | [structure: spiro dioxolane benzothiazine-S,S-dioxide with N-(CH$_2$)$_4$-N-piperazine-(4-fluorophenyl)] | Pale brown prism crystals 120.5–121.5° C. (ethyl acetate-hexane) | (270 MHz) 1.50–1.78(4H, m), 2.43(2H, t, J=7.0Hz), 2.59(4H, m), 3.11(4H, m), 3.46(2H, t, J=7.0Hz), 3.88(2H, s), 4.05–4.22(2H, m), 4.22–4.38(2H, m), 6.77–7.05(4H, m), 7.42–7.66(3H, m), 7.79(1H, m) | (KBr) 1508, 1329, 1210, 1151, 1052, 830, 763 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 31 | (spiro-dioxolane benzothiazine dioxide with N-(CH₂)₃-piperazine-CH(Ph)₂) | Colorless powdery crystals 93.5–95.5° C. (ethanol) | (270 MHz) 1.80(2H, m), 2.28–2.62(10H, m), 3.47(2H, t, J=6.6Hz), 3.88(2H, s), 4.10(2H, m), 4.23(3H, m), 7.13–7.34(6H, m), 7.36–7.46(4H, m), 7.46–7.62(3H, m), 7.77(1H, d, J=7.3Hz) | (KBr) 2813, 1333, 1156, 1054, 1032, 996, 952, 768, 735, 715, 692 |
| 32 | (spiro-dioxolane benzothiazine dioxide with N-(CH₂)₃-piperidine-Ph) | Pale yellow oil | (270 MHz) 1.66–1.96(6H, m), 2.07(2H, dt, J=2.8Hz, 11.5Hz), 2.40–2.59(3H, m), 3.05(2H, s), 3.51(2H, t, J=6.9Hz), 3.92(2H, s), 4.08–4.21(2H, m), 4.21–4.35(2H, m), 7.14–7.37(5H, m), 7.44–7.64(3H, m), 7.78(1H, m) | (film) 2936, 1332, 1155, 1052, 948, 762, 700 |
| 33 | (spiro-dioxolane benzothiazine dioxide with N-(CH₂)₃-piperazine-(3-OMe-Ph)) | Colorless powdery crystals 109.0–110.0° C. (ethyl acetate-hexane) | (270 MHz) 1.86(2H, quint, J=7.3Hz), 2.51(2H, t, J=7.3Hz), 2.60(4H, m), 3.20(4H, m), 3.53(2H, t, J=7.3Hz), 3.79(3H, s), 3.92(2H, s), 4.16(2H, m), 4.27(2H, m), 6.39–6.49(2H, m), 6.55(1H, dd, J=1.3Hz, 7.9Hz), 7.17(1H, t, J=7.9Hz), 7.47–7.62(3H, m), 7.80(1H, d, J=7.6Hz) | (KBr) 2947, 1602, 1574, 1496, 1458, 1332, 1202, 1157, 1053, 768, 699 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 34 | (structure: spiro-dioxolane benzo-sultam with N-(CH₂)₃-N-piperazinyl-4-methoxyphenyl) | Pale yellow needle crystals 119.0–119.5° C. (ethyl acetate-hexane) | (270 MHz) 1.86(2H, quint, J=6.9Hz), 2.51(2H, t, J=7.3Hz), 2.62 (4H, m), 3.10(4H, m), 3.52 (2H, t, J=6.9Hz), 3.77(3H, s), 3.92(2H, s), 4.17(2H, m), 4.27(2H, m), 6.80–6.95(4H, m), 7.47–7.62(3H, m), 7.79(1H, m) | (KBr) 1508, 1337, 1224, 1161, 1054, 826, 767, 694 |
| 35 | (structure: spiro-dioxolane benzo-sultam with N-(CH₂)₃-N-piperazinyl-2-fluorophenyl) | Colorless prism crystals 70.0–71.5° C. (ethyl acetate-hexane-ethyl ether) | (270 MHz) 1.86(2H, quint, J=7.3Hz), 2.52(2H, t, J=7.3Hz), 2.64(4H, m), 3.12 (4H, m), 3.53(2H, t, J=7.3Hz), 3.92(2H, s), 4.18(2H, m), 4.30(2H, m), 6.88–7.10(4H, m), 7.46–7.62(3H, m), 7.80(1H, m) | (KBr) 2819, 1501, 1445, 1330, 1231, 1162, 1052, 948, 769, 752, 693 |
| 36 | (structure: spiro-dioxolane benzo-sultam with N-(CH₂)₃-N-piperazinyl-3-fluorophenyl) | Colorless plate crystals 154.0–155.0° C. (ethyl acetate-hexane) | (270 MHz) 1.86(2H, quint, J=6.9Hz), 2.50(2H, t, J=6.9Hz), 2.60(4H, m), 3.20 (4H, m), 3.52(2H, t, J=6.9Hz), 3.92 (2H, s), 4.15(2H, m), 4.29(2H, m), 6.47–6.70(3H, m), 7.18(1H, m), 7.47–7.62(3H, m), 7.79(1H, m) | (KBr) 1608, 1496, 1323, 1255, 1154, 1124, 1049, 996, 973, 760, 691 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 37 | (structure with 4-hydroxyphenyl piperazine) | Colorless prism crystals 184.5–185.5° C. (methanol-ethyl ether) | (270 MHz) 1.86(2H, m), 2.51(2H, t, J=7.3Hz), 2.62(4H, m), 3.09(4H, m), 3.52(2H, t, J=6.9Hz), 3.92(2H, s), 4.16 (2H, m), 4.27(2H, m), 6.76(2H, m), 6.84(2H, m), 7.48–7.62(3H, m), 7.79(1H, m) | (KBr) 3676, 2820, 1514, 1457, 1332, 1230, 1164, 1052, 964, 824, 763, 692 |
| 38 | (structure with 4-chlorophenyl piperazine) | Colorless prism crystals 118.5–119.5° C. (ethyl acetate-hexane) | (270 MHz) 1.86(2H, quint, J=7.0Hz), 2.50 (2H, t, J=7.0Hz), 2.60(4H, m), 3.16 (4H, m), 3.52(2H, t, J=7.0Hz), 3.92 (2H, s), 4.16(2H, m), 4.29(2H, m), 6.83(2H, m), 7.20(2H, m), 7.46–7.62(3H, m), 7.80(1H, m) | (KBr) 1498, 1331, 1305, 1232, 1175, 1154, 1050, 938, 818, 772, 734, 696 |
| 39 | (structure with 4-NHSO₂CH₃ phenyl piperazine) | Pale red oil | (400 MHz) 1.86(2H, quint, J=7.0Hz), 2.51 (2H, t, J=7.0Hz), 2.61(4H, m), 2.94(3H, s), 3.19(4H, m), 3.53(2H, t, J=7.0Hz), 3.91(2H, s), 4.15(2H, m), 4.29(2H, m), 6.11(1H, br.s), 6.89(2H, d, J=9.0Hz), 7.15(2H, d, J=9.0Hz), 7.48–7.60(3H, m), 7.79 (1H, d, J=7.9Hz) | (film) 3264, 2949, 2823, 1609, 1514, 1453, 1388, 1329, 1237, 1154, 1052, 974, 824, 766, 736, 692 |
| 40 | (structure with 4-fluorobenzoyl piperidine) | Colorless prism crystals 115.0–116.0° C. (ethanol) | (270 MHz) 1.70–1.93(6H, m), 2.10(2H, m), 2.48 (2H, t, J=6.9Hz), 3.01(2H, m), 3.21 (1H, m), 3.51(2H, t, J=6.6Hz), 3.93 (2H, s), 4.18(2H, m), 4.29(2H, m), 7.14(2H, t, J=8.6Hz), 7.46–7.63 (3H, m), 7.79(1H, m), 7.97(2H, dd, J=5.3Hz, 8.6Hz) | (KBr) 1680, 1595, 1325, 1211, 1183, 1158, 1055, 953, 758 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 41 | [structure: spiro dioxolane benzothiazine dioxide with N-(CH₂)₃-piperidine-C(=O)-2,4-difluorophenyl] | Pale yellow oil | (270 MHz) 1.65–1.95(6H, m), 2.08(2H, m), 2.47(2H, m), 2.97(2H, m), 3.09(1H, m), 3.50(2H, t, J=6.6Hz), 3.92(2H, s), 4.17(2H, m), 4.29(2H, m), 6.82–7.00(2H, m), 7.49–7.60(3H, m), 7.76–7.88(2H, m) | (film) 2944, 2804, 1682, 1611, 1494, 1446, 1334, 1152, 1054, 946, 758, 735, 694 |
| 42 | [structure: spiro dioxolane benzothiazine dioxide with N-(CH₂)₂-piperidine-6-fluorobenzisoxazole] | Colorless oil [monofumarate] Colorless powdery crystals 135.5–137.0° C. (ethanol) | (400 MHz) 2.02–2.07(4H, m), 2.26(2H, m), 2.72(2H, t, J=6.6Hz), 3.05–3.15 (3H, m), 3.62(2H, t, J=6.6Hz), 4.03 (2H, s), 4.17(2H, m), 4.30(2H, m), 7.05(1H, m), 7.24(1H, m), 7.50–7.59(3H, m), 7.67(1H, dd, J=5.1Hz, 8.7Hz), 7.79(1H, dd, J=1.6Hz, 8.6Hz) | (film) 2944, 2812, 1614, 1337, 1272, 1243, 1155, 1053, 996, 957, 841 |
| 43 | [structure: spiro dioxolane benzothiazine dioxide with N-(CH₂)₃-piperidine-6-fluorobenzisoxazole] | Colorless oil [monofumarate] Colorless prism crystals 174.5–176.5° C. (ethanol) | (400 MHz) 1.86(2H, m), 2.03–2.08(4H, m), 2.16 (2H, m), 2.51(2H, t, J=7.1Hz), 3.03–3.10(3H, m), 3.53(2H, t, J=6.8Hz), 3.92(2H, s), 4.17(2H, m), 4.29(2H, m), 7.05(1H, dt, J=2.0Hz, 8.8Hz), 7.23(1H, dd, J=2.0Hz, 8.6Hz), 7.50–7.58(3H, m), 7.68(1H, dd, J=5.1Hz, 8.7Hz), 7.79(1H, dd, J=1.7Hz, 8.9Hz) | (film) 2970, 1613, 1328, 1268, 1155, 1121, 1053, 956, 768, 746 |
| 44 | [structure: spiro dioxolane benzothiazine dioxide with N-(CH₂)₃-piperazine-benzisothiazole] | Pale yellow oil | (270 MHz) 1.89(2H, quint, J=6.9Hz), 2.56 (2H, t, J=6.9Hz), 2.70(4H, m), 3.50–3.61(6H, m), 3.94(2H, s), 4.19 (2H, m), 4.29(2H, m), 7.36(1H, t, J=7.6Hz), 7.43–7.62(4H, m), 7.77–7.85(2H, m), 7.91(1H, d, J=8.6Hz) | (film) 2945, 2885, 2818, 1492, 1331, 1262, 1155, 1052, 949, 772, 738, 693 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 45 | (structure: spiro dioxolane-benzothiazine-S,S-dioxide with N-(CH₂)₃-piperidinyl-6-fluoroindazole) | Colorless prism crystals 169.5–171.5° C. (chloroform-ethyl ether) | (400 MHz) 1.90(2H, quint, J=6.9Hz), 2.07(4H, m), 2.19(2H, m), 2.53(2H, t, J=6.9Hz), 2.99–3.15(3H, m), 3.53(2H, t, J=6.9Hz), 3.94(2H, s), 4.18(2H, m), 4.29(2H, m), 6.90(1H, dt, J=2.1Hz, 8.9Hz), 7.08(1H, dd, J=2.1Hz, 8.9Hz), 7.48–7.60(3H, m), 7.71(1H, dd, J=5.1Hz, 8.9Hz), 7.80(1H, m), 9.79(1H, br.s) | (KBr) 2952, 2360, 1628, 1518, 1471, 1444, 1320, 1226, 1156, 1054, 1014, 956, 830, 766, 737, 706, 685, 668 |
| 46 | (structure: spiro dioxolane-benzothiazine-S,S-dioxide with N-(CH₂)₃-piperidinyl-2-pyridyl) | Colorless needle crystals 122.0–122.5° C. (ethyl acetate-hexane) | (270 MHz) 1.87(2H, quint, J=7.3Hz), 2.56(4H, m), 3.47–3.58(6H, m), 3.92(2H, s), 4.17(2H, m), 4.27(2H, m), 6.58–6.68(2H, m), 7.43–7.61(4H, m), 7.80(1H, d, J=7.3Hz), 8.18(1H, d, J=4.0Hz) | (KBr) 2955, 2888, 2804, 1594, 1482, 1432, 1324, 1240, 1158, 1054, 953, 766, 690 |
| 47 | (structure: spiro dioxolane-benzothiazine-S,S-dioxide with N-(CH₂)₃-piperazinyl-2-pyrimidinyl) | Pale yellow prism crystals 118.5–119.5° C. (ethyl acetate-hexane) | (270 MHz) 1.87(2H, quint, J=6.9Hz), 2.44–2.59(6H, m), 3.53(2H, t, J=6.9Hz), 3.82(4H, m), 3.92(2H, s), 4.17(2H, m), 4.28(2H, m), 6.48(1H, t, J=4.6Hz), 7.47–7.63(3H, m), 7.79(1H, m), 8.30(2H, d, J=4.6Hz) | (KBr) 2954, 2905, 2810, 1585, 1548, 1497, 1360, 1323, 1160, 1054, 982, 956, 762, 690 |

TABLE 1-continued

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 48 | (structure with 4-fluorobenzoyl-piperidine-propyl-sulfonamide spiro dithiolane) | Brown oil | (400 MHz) 1.75–1.96(6H, m), 2.12(2H, m), 2.51(2H, t, J=7.0Hz), 3.01(2H, m), 3.21(1H, m), 3.49(2H, m), 3.57–3.70(4H, m), 4.13(2H, s), 7.14(2H, t, J=8.6Hz), 7.39(1H, m), 7.50(1H, m), 7.76(1H, dd, J=1.2Hz, 7.9Hz), 7.91–8.01(3H, m) | (film) 2945, 2808, 1682, 1597, 1506, 1308, 1160, 976, 852, 736 |
| 49 | (structure with fluoroindazole-piperidine-propyl-sulfonamide spiro dithiolane) | Colorless powdery crystals 144.0–144.5° C. (chloroform-ethyl ether) | (400 MHz) 1.98(2H, quint, J=7.0Hz), 2.09(4H, m), 2.25(2H, m), 2.59(2H, t, J=7.0Hz), 3.03–3.18(3H, m), 3.49(2H, m), 3.58–3.67 (4H, m), 4.13(2H, s), 6.89(1H, dt, J=2.0Hz, 8.9Hz), 7.08(1H, dd, J=2.0Hz, 8.9Hz), 7.39 (1H, t, J=7.7Hz), 7.51(1H, dt, J=1.2Hz, 7.7Hz), 7.72(1H, dd, J=5.1Hz, 8.9Hz), 7.77(1H, d, J=7.7Hz), 7.95(1H, d, J=7.7Hz) | (KBr) 3622, 3538, 2921, 1626, 1471, 1314, 1162, 1070, 828, 770 |
| 50 | (structure with 4-hydroxyphenyl-piperazine-propyl-sulfonamide spiro dithiolane) | Colorless powdery crystals 173.0–175.0° C. (acetonitrile-isopropyl ether) | (400 MHz) [DMSO-d$_6$/TMS] 1.83(2H, quint, J=6.9Hz), 2.41(2H, t, J=6.9Hz), 2.50(4H, m), 2.95(4H, m), 3.45(2H, t, J=6.9Hz), 3.58(2H, m), 3.70 (2H, m), 4.08(2H, s), 6.64(2H, d, J= 8.9Hz), 6.76(2H, d, J=8.9Hz), 7.50 (1H, t, J=7.8Hz), 7.64(1H, dt, J=1.0Hz, 7.8Hz), 7.68(1H, dd, J=1.0Hz, 7.8Hz), 7.99(1H, d, J=7.8Hz), 8.74(1H, s) | (KBr) 2930, 2829, 1589, 1515, 1296, 1172, 1156, 918, 826, 780 |
| 51 | (structure with 4-fluorophenyl-piperazine-ethyl-sulfonamide spiro dithiolane) | Colorless prism crystals 124.0–124.5° C. (ethyl acetate hexane) | (400 MHz) 2.70(4H, m), 2.77(2H, t, J=6.6Hz), 3.13 (4H, m), 3.46(2H, m), 3.63(2H, m), 3.70 (2H, t, J=6.6Hz), 4.21(2H, s), 6.87 (2H, m), 6.96(2H, m), 7.39(1H, t, J=7.5 Hz), 7.51(1H, dt, J=1.2Hz, 7.5Hz), 7.76 (1H, d, J=7.5Hz), 7.94(1H, d, J=7.5Hz) | (KBr) 3425, 2942, 2820, 1592, 1514, 1456, 1312, 1232, 1163, 822, 759 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 52 | (structure: spiro dithiolane benzothiazine dioxide with (CH₂)₂N-piperidine-4-hydroxyphenyl) | Colorless needle crystals 188.0–188.5° C. (ethyl acetate-hexane) | (400 MHz) 2.69(4H, m), 2.78(2H, t, J=6.6Hz), 3.09 (4H, m), 3.45(2H, m), 3.62(2H, m), 3.70(2H, t, J=6.6Hz), 4.21(2H, s), 6.75(2H, m), 6.84(2H, m), 7.39(1H, dt, J=1.0Hz, 8.0Hz), 7.50(1H, dt, J=1.3Hz, 8.0Hz), 7.76(1H, dd, J=1.3Hz, 8.0Hz), 7.94(1H, dd, J=1.0Hz, 8.0Hz) | (KBr) 2944, 2829, 1514, 1439, 1302, 1240, 1161, 782, 754, 660, |
| 53 | (structure: spiro dithiane benzothiazine dioxide with (CH₂)₂N-piperidine-4-hydroxyphenyl) | Pale yellow prism crystals 183.0–184.5° C. (acetonitrile-isopropyl ether) | (400 MHz) 1.90(2H, quint, J=6.7Hz), 2.01(1H, m), 2.21(1H, m), 2.57(2H, t, J=6.7Hz), 2.64(4H, m), 2.80(2H, dt, J=3.7Hz, 14.7 Hz), 3.10(4H, m), 3.17(2H, m), 3.67(2H, t, J=6.7Hz), 4.51(2H, s), 6.76(2H, m), 6.84(2H, m), 7.45(1H, dt, J=1.3Hz, 7.8Hz), 7.54(1H, dt, J=1.3Hz, 7.8Hz), 7.82(1H, dd, J=1.3Hz, 7.8Hz), 8.06(1H, dd, J=1.3Hz, 7.8Hz) | (KBr) 2934, 2826, 1588, 1514, 1456, 1421, 1385, 1303, 1270, 1242, 1163, 1070, 1000, 974, 922, 818, 773, 764, 728, 656, |
| 54 | (structure: spiro dithiane benzothiazine dioxide with (CH₂)₃N-piperidine-4-hydroxyphenyl) | Pale brown powdery crystals 178.0–179.0° C. (acetonitrile-isopropyl ether) | (400 MHz) 2.02(1H, m), 2.22(1H, m), 2.79(4H, m), 2.76 (2H, t, J=6.6Hz), 2.80(2H, dt, J=3.7Hz, 14.7Hz), 3.09–3.17(6H, m), 3.72(2H, t, J=6.6Hz), 4.56(2H, s), 6.76(2H, m), 6.84(2H, m), 7.44(1H, dt, J=1.0Hz, 8.0Hz), 7.54(1H, dt, J=1.2Hz, 8.0Hz), 7.82(1H, dd, J=1.2Hz, 8.0Hz), 8.07(1H, dd, J=1.0Hz, 8.0Hz) | (KBr) 3425, 2942, 2822, 1592, 1514, 1456, 1312, 1232, 1163, 822, 759 |
| 55 | (structure: dimethoxy benzothiazine dioxide with (CH₂)₃N-piperidine-4-fluorophenyl) | Pale yellow oil | (270 MHz) 1.88(2H, m), 2.52(2H, t, J=7.3Hz), 2.63(4H, t, J=5.3Hz), 3.13(4H, t, J=5.3Hz), 3.26(6H, s), 3.54(2H, t, J=6.6Hz), 3.98(2H, s), 6.84–6.99 (4H, m), 7.48–7.59(2H, m), 7.68(1H, dd, J=2.0Hz, 7.3Hz), 7.84(1H, dd, J=2.0Hz, 7.3Hz) | (film) 2947, 2823, 1506, 1456, 1329, 1232, 1146, 1062, 954, 826, 769, 688 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 56 | (structure: OCH₃-substituted benzothiazine dioxide with (CH₂)₃N-piperazine-4-fluorophenyl) | Pale yellow oil [dihydrochloride] Pale yellow powdery crystals (methanol-ethyl ether) | (270 MHz) 1.83(2H, m), 2.39(2H, t, J=7.3Hz), 2.53 (4H, t, J=5.3Hz), 3.09(4H, t, J=5.3Hz), 3.69(2H, t, J=7.3Hz), 3.80(3H, s), 6.08 (1H, s), 6.83–7.00(4H, m), 7.54 (1H, dt, J=1.3Hz, 7.9Hz), 7.63(1H, dt, J= 1.3Hz, 7.9Hz), 7.79(1H, dd, J=1.3Hz, 7.9Hz), 7.86(1H, dd, J=1.3Hz, 7.9Hz), | (film) 1520, 1450, 1380, 1330, 1240, 1180, 1080, 790 |
| 57 | (structure: OCH₃-substituted benzothiazine dioxide with (CH₂)₃N-piperazine-4-fluorophenyl) | Pale yellow oil [dihydrochloride] Pale yellow powdery crystals 180.0–182.0° C. (methanol-ethyl ether) | (270 MHz) 1.86(2H, m), 2.50(2H, m), 2.60 (4H, t, J=5.3Hz), 3.12(4H, t, J= 5.3Hz), 3.39(2H, m), 3.54(3H, s), 3.85(1H, dd, J=4.6Hz, 15.2Hz), 4.10(1H, dd, J=4.6Hz, 15.2Hz), 4.39(1H, m), 6.84–6.99(4H, m), 7.44–7.59(3H, m), 7.83(1H, dd, J= 1.3Hz, 7.9Hz) | (film) 1510, 1460, 1330, 1230, 1170, 1070, 950, 830, 760, 700 |
| 58 | (structure: OCH₃-substituted benzothiazine dioxide with (CH₂)₃N-piperidine-C(=O)-4-fluorophenyl) | Pale yellow oil | (270 MHz) 1.70–1.90(6H, m), 2.10(2H, m), 2.48 (2H, m), 3.00(2H, m), 3.20(1H, m), 3.32(1H, m), 3.42(1H, m), 3.55(3H, s), 3.87(1H, dd, J=4.6Hz, 15.2Hz), 4.09(1H, dd, J=4.6Hz, 15.2Hz), 4.38(1H, t, J= 4.6Hz), 7.14(2H, m), 7.45–7.60(3H, m), 7.83(1H, d, J=7.2Hz), 7.96(2H, m) | (film) 2942, 2820, 1681, 1599, 1505, 1446, 1337, 1160, 975, 854, 760, 702 |
| 59 | (structure: OC₂H₅-substituted benzothiazine dioxide with (CH₂)₃N-piperazine-4-fluorophenyl) | Pale yellow oil | (270 MHz) 1.29(3H, t, J=7.3Hz), 1.85 (2H, quint, J=7.3Hz), 2.39–2.70 (6H, m), 3.11(4H, m), 3.31(1H, m), 3.48(1H, m), 3.60–3.88(3H, m), 4.09 (1H, dd, J=4.6Hz, 14.5Hz), 4.51 (1H, t, J=4.6Hz), 6.80–7.03(4H, m), 7.40–7.61(3H, m), 7.82(1H, d, J=7.3Hz) | (film) 2943, 2821, 1515, 1506, 1456, 1335, 1232, 1170, 1069, 827, 763, 705 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 60 | (structure with OCH₃, benzothiazine S O₂, -(CH₂)₃-, piperidine-N, phenyl-OH) | Pale yellow oil | (270 MHz) 1.86(2H, m), 2.51(2H, m), 2.63 (4H, m), 3.08(4H, m), 3.33(1H, m), 3.43(1H, m), 3.52(3H, s), 3.83 (1H, dd, J=4.6Hz, 15.2Hz), 4.07 (1H, dd, J=4.6Hz, 15.2Hz), 4.37 (1H, t, J=4.6Hz), 6.73(2H, d, J= 8.6Hz), 6.82(2H, d, J=8.6Hz), 7.45–7.60(3H, m), 7.83(1H, d, J=7.9Hz) | (film) 2948, 2827, 1520, 1463, 1337, 1228, 1163, 924, 824, 765, 727, 700 |
| 61 | (structure with OCH₂-phenyl, benzothiazine S O₂, -(CH₂)₃-, piperidine-N, phenyl-F) | Pale yellow oil [dihydrochloride] Colorless powdery crystals 209.0–210.0° C. (methanol-ethyl ether) | (270 MHz) 1.83(2H, quint, J=7.3Hz), 2.47(2H, m), 2.57(4H, m), 3.09(4H, m), 3.41 (2H, m), 3.87(1H, dd, J=4.6Hz, 15.2Hz), 4.10(1H, dd, J=4.6Hz, 15.2Hz), 4.61 (1H, t, J=4.6Hz), 4.71(1H, d, J=11.9Hz), 4.78(1H, d, J=11.9Hz), 6.80–7.04(4H, m), 7.30–7.41(5H, m), 7.41–7.60 (3H, m), 7.83(1H, dd, J=2.0Hz, 7.3Hz) | (film) 1500, 1455, 1334, 1232, 1169, 1068, 817, 762, 701 |
| 62 | (structure with dioxolane spiro, benzothiazine S O₂, -(CH₂)₃-, piperidine-N, phenyl-F) | Colorless prism crystals 102.0–104.0° C. (ethyl acetate-hexane) | (270 MHz) 1.86(2H, m), 2.51(2H, t, J=7.3Hz), 2.61(4H, m), 3.12(4H, m), 3.52(2H, t, J=6.6Hz), 3.92(2H, s), 4.06–4.23 (2H, m), 4.23–4.38(2H, m), 6.80–7.04(4H, m), 7.45–7.65(3H, m), 7.80(1H, m) | (KBr) 2820, 1510, 1456, 1330, 1232, 1158, 1051, 995, 953, 816, 762 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 63 | (structure: dimethyl dioxolane spiro benzothiazine-S,S-dioxide with N-(CH₂)₃-piperazine-4-fluorophenyl) | Colorless oil | (270 MHz) 1.33(3H, d, J=5.9Hz), 1.41(3H, d, J=5.9Hz), 1.86(2H, m), 2.50(2H, m), 2.62(4H, m), 3.12(4H, m), 3.52 (2H, m), 3.80–4.04(4H, m), 6.84–6.99(4H, m), 7.46–7.58(3H, m), 7.77(1H, d, J=7.2Hz) | (film) 2973, 2820, 1510, 1331, 1231, 1154, 1075, 958, 826, 763 |
| 64 | (structure: dioxane spiro benzothiazine-S,S-dioxide with N-(CH₂)₃-piperazine-4-fluorophenyl) | Colorless prism crystals 119.0–120.0° C. (ethyl acetate-hexane) | (270 MHz) 1.56(1H, m), 1.91(2H, m), 2.32(1H, m), 2.58 (2H, t, J=7.3Hz), 2.67(4H, m), 3.14 (4H, m), 3.47(2H, t, J=6.6Hz), 3.97–4.28 (4H, m), 4.40(2H, s), 6.80–7.05(4H, m), 7.49(1H, ddd, J=1.3Hz, 7.3Hz, 7.9Hz), 7.60(1H, ddd, J=1.3Hz, 7.3Hz, 7.9Hz), 7.76(1H, dd, J=1.3Hz, 7.9Hz), 7.86(1H, dd, J=1.3Hz, 7.9Hz) | (KBr) 2818, 1509, 1323, 1226, 1139, 1076, 1016, 960, 828, 768 |
| 65 | (structure: oxathiolane spiro benzothiazine-S,S-dioxide with N-(CH₂)₃-piperazine-4-fluorophenyl) | Colorless oil [dihydrochloride] Colorless powdery crystals 112° C. (decomposed) (chloroform-ethyl ether) | (270 MHz) 1.87(2H, quint, J=6.9Hz), 2.39–2.70(6H, m), 3.12(4H, m), 3.28(1H, m), 3.32–3.47 (2H, m), 3.60(1H, m), 4.00(1H, d, J=15.2Hz), 4.10(1H, dt, J=5.3Hz, 9.6Hz), 4.20 (1H, d, J=15.8Hz), 4.61(1H, m), 6.80–7.03 (4H, m), 7.47(1H, m), 7.57(1H, m), 7.71 (1H, d, J=7.9Hz), 7.80(1H, d, J=7.3Hz) | (film) 2945, 2879, 2819, 1510, 1454, 1329, 1232, 1171, 1046, 950, 826, 762, 704 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 66 | (spiro-dithiolane benzosultam with piperazinyl-propyl and 4-fluorophenyl) | Colorless prism crystals 137.5–138.5° C. (ethyl acetate-hexane) | (270 MHz) 1.92(2H, quint, J=7.3Hz), 2.54(2H, t, J= 7.3Hz), 2.63(4H, m), 3.13(4H, m), 3.40–3.53(2H, m), 3.56–3.70(4H, m), 4.11(2H, s), 6.83–7.01(4H, m), 7.40 (1H, dt, J=1.3Hz, 7.9Hz), 7.52(1H, dt, J=1.3Hz, 7.9Hz), 7.77(1H, d, J=7.9Hz), 7.94(1H, dd, J=1.3Hz, 7.9Hz) | (KBr) 2813, 1508, 1299, 1222, 1159, 1136, 1115, 828 |
| 67 | (spiro-dithiane benzosultam with piperazinyl-propyl and 4-fluorophenyl) | Colorless oil [monomaleate] Colorless prism crystals 139.0–140.5° C. (chloroform-ethyl ether) | (400 MHz) 1.90(2H, quint, J=6.7Hz), 2.02(1H, m), 2.21 (1H, m), 2.57(2H, t, J=6.7Hz), 2.64(4H, m), 2.81(2H, dt, J=3.7Hz, 14.6Hz), 3.10–3.22 (6H, m), 3.67(2H, t, J=6.7Hz), 4.50(2H, s), 6.87(2H, m), 6.96(2H, m), 7.45(1H, dt, J=1.1Hz, 7.7Hz), 7.54(1H, dt, J=1.3Hz, 7.7Hz), 7.83 (1H, dd, J=1.3, 7.7Hz), 8.07(1H, dd, J=1.1H, 7.7Hz) | (film) 3057, 2947, 2820, 1510, 1456, 1380, 1312, 1231, 1164, 1074, 1024, 941, 817, 779, 757, 737, 716, 656 |
| 68 | (spiro-thiane benzosultam with piperazinyl-propyl and 4-fluorophenyl) | Colorless oil | (400 MHz) 2.03(1H, m), 2.24(1H, m), 2.71(4H, m), 2.76(2H, t, J=6.6Hz), 2.82(2H, dt, J= 3.7Hz, 14.7Hz), 3.10–3.20(6H, m), 3.72(2H, t, J=6.6Hz), 4.56(2H, s), 6.87(2H, m), 6.96(2H, m), 7.45(1H, dt, J=1.0Hz, 7.8Hz), 7.55(1H, dt, J=1.3Hz, 7.8Hz), 7.83(1H, dd, J=1.3Hz, 7.8Hz), 8.08(1H, dd, J=1.0Hz, 7.8Hz) | (film) 3058, 2944, 1454, 1309, 1509, 1163, 1072, 1235, 971, 817, 1012, 742, 719, 759, 656 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 69 | (structure with H₅C₂S, C₂H₅S, benzothiazine-S,O₂ core, -(CH₂)₃N-piperazine-4-fluorophenyl) | Colorless oil [dihydrochloride] Colorless powdery crystals 163.0–166.5° C. (methanol) | (270 MHz) 1.16(6H, t, J=7.3Hz), 1.90(2H, quint, J=6.9Hz), 2.42–2.70(6H, m), 2.63(4H, m), 3.13(4H, m), 3.62(2H, t, J=6.9Hz), 4.18(2H, s), 6.82–7.01(4H, m), 7.42 (1H, dt, J=1.3Hz, 7.9Hz), 7.55(1H, dt, J=1.3Hz, 7.9Hz), 7.83(1H, dd, J=1.3Hz, 7.9Hz), 7.95(1H, dd, J=1.3Hz, 7.9Hz) | (film) 2929, 2819, 1511, 1455, 1378, 1311, 1231, 1164, 1072, 931, 826, 756, 717 |
| 70 | (benzothiazinone structure with -(CH₂)₃N-piperazine-4-fluorophenyl) | Brown needle crystals 110.0–112.0° C. (2-propanol) | (270 MHz) 1.81(2H, quint, J=6.9Hz), 2.47(2H, t, J=6.9Hz), 2.57(4H, m), 3.11(4H, m), 3.29(2H, t, J=6.9Hz), 4.48(2H, s), 6.80–7.02(4H, m), 7.68–7.92(3H, m), 8.07(1H, dd, J=1.3Hz, 7.3Hz) | (KBr) 1706, 1508, 1341, 1276, 1242, 1172, 1126, 816, 768 |
| 71 | (benzothiazinone structure with -(CH₂)₃N-piperazine-phenyl) | Colorless oil | (270 MHz) 1.81(2H, quint, J=6.9Hz), 2.46 (2H, t, J=6.9Hz), 2.57(4H, m), 3.18 (4H, m), 3.29(2H, t, J=6.9Hz), 4.48(2H, s), 6.85(1H, t, J=7.3Hz), 6.92(2H, d, J=7.9Hz), 7.26(2H, m), 7.68–7.93(3H, m), 8.07(1H, dd, J=1.3Hz, 7.9Hz) | (CHCl₃ solution) 2815, 1695, 1590, 1350, 1170 |
| 72 | (benzothiazinone structure with -(CH₂)₃N-piperidine-C(=O)-4-fluorophenyl) | Brown needle crystals 109.0–110.0° C. (ethanol) | (270 MHz) 1.70–1.90(6H, m), 2.08(2H, m), 2.42(2H, t, J=7.3Hz), 2.93(2H, m), 3.18(1H, m), 3.26(2H, t, J=7.3Hz), 4.46(2H, s), 7.13(2H, m), 7.70–7.83(2H, m), 7.86(1H, m), 7.95 (2H, m), 8.07(1H, dd, J=1.3Hz, 7.9Hz) | (KBr) 2947, 2772, 1705, 1680, 1598, 1505, 1339, 1225, 1170, 976, 854, 768 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 73 | (benzothiazine-NOH with N-(CH$_2$)$_3$-piperidine-N-phenyl) | Colorless needle crystals 191.0–192.5° C. (decomposed) (ethanol) | (270 MHz) 1.92(2H, m), 2.63(2H, m), 2.75 (4H, m), 3.08(2H, t, J=6.9Hz), 3.35(4H, m), 4.69(2H, s), 6.89 (1H, t, J=7.3Hz), 6.95(2H, d, J= 8.0Hz), 7.22–7.33(2H, m), 7.38– 7.52(2H, m), 7.80(1H, m), 7.90 (1H, m), 13.00(1H, br.s) | (KBr) 2830, 1600, 1496, 1347, 1248, 1174, 1126, 970, 923, 755 |
| 74 | (benzothiazine-NOH with N-(CH$_2$)$_3$-piperidine-C(=O)-4-F-phenyl) | Colorless needle crystals 186.5–188.0° C. (decomposed) (acetonitrile) | (270 MHz) [DMSO-d$_6$/TMS] 1.40–1.81(6H, m), 2.02(2H, dt, J=1.3Hz, 9.9Hz), 2.30(2H, t, J=6.6Hz), 2.84(2H, m), 2.97(2H, t, J=6.6Hz), 3.20–3.42(1H, m), 4.59(2H, s), 7.33(2H, t, J=8.9Hz), 7.58–7.76 (2H, m), 7.79(1H, dd, J=1.3Hz, 7.6Hz), 7.97–8.12(3H, m), 12.28(1H, s) | (KBr) 2943, 1684, 1597, 1508, 1340, 1242, 1176, 1156, 972, 840, 752 |
| 75 | (benzothiazine-NOH with N-(CH$_2$)$_3$-piperidine-C(=O)-4-F-phenyl) | Colorless prism crystals 173.0–174.0° C. (ethyl acetate-hexane) | (270 MHz) 1.91(2H, m), 2.62(2H, m), 2.75 (4H, m), 3.08(2H, t, J=6.6Hz), 3.26(4H, m), 4.68(2H, s), 6.84– 7.03(4H, m), 7.47(2H, m), 7.81 (1H, dd, J=2.0Hz, 7.3Hz), 7.89 (1H, dd, J=2.0Hz, 7.3Hz), 12.72 (1H, br.s) | (KBr) 3676, 2814, 2362, 1734, 1561, 1506, 1342, 1210, 1174, 970, 830, 784, 768 |
| 76 | (benzothiazine-OH with N-(CH$_2$)$_3$-piperidine-C(=O)-4-F-phenyl) | Colorless powdery crystals 161.0–162.5° C. (ethyl acetate) | (270 MHz) 1.30–1.60(2H, m), 1.63–2.10(6H, m), 2.30–2.62(3H, m), 2.90–3.18(1H, m), 3.61(1H, dd, J=2.9Hz, 14.8Hz), 3.84 (1H, m), 4.25(1H, dd, J=2.9Hz, 14.8Hz), 4.65(1H, t, J=2.9Hz), 7.11(2H, m), 7.44(1H, m), 7.50–7.70(2H, m), 7.81(1H, m), 7.84–7.98(2H, m) | (KBr) 2963, 2815, 1673, 1593, 1317, 1234, 1208, 1154, 1059, 969, 853, 840, 763 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 77 | [structure: 4-hydroxy-benzothiazine-S,S-dioxide with (CH₂)₃-piperazine-4-fluorophenyl] | Colorless plate crystals 170.0–174.5° C. (decomposed) (ethyl acetate) | (270 MHz) 1.85(2H, m), 2.27(2H, t, J=6.7Hz), 2.46(1H, m), 2.50–2.66(3H, m), 2.74–3.01(4H, m), 3.10(1H, dt, J=4.6Hz, 14.5Hz), 3.60(1H, dd, J=2.7Hz, 14.5Hz), 3.86(1H, dt, J=7.3Hz, 13.9Hz), 4.24(1H, dd, J=2.9Hz, 14.9Hz), 4.63(1H, t, J=2.9Hz), 5.90(1H, br.s), 6.65–6.84(2H, m), 6.87–7.01(2H, m), 7.38–7.64(3H, m), 7.83(1H, d, J=7.3Hz) | (KBr) 2843, 1508, 1323, 1241, 1169, 922, 820, 714 |
| 78 | [structure: benzothiazine-S,S-dioxide with (CH₂)₃-piperazine-4-fluorophenyl] | Colorless oil | (400 MHz) 1.96(2H, m), 2.45(2H, t, J=6.7Hz), 2.57(4H, m), 3.10(4H, m), 3.84(2H, t, J=6.7Hz), 6.22(1H, d, J=7.9Hz), 6.66(1H, d, J=6.3Hz), 6.84–6.87 (2H, m), 6.93–6.97(2H, m), 7.35(1H, d, J=7.8Hz), 7.46(1H, m), 7.57(1H, m), 7.91(1H, d, J=8.0Hz) | (film) 2948, 2818, 1621, 1505, 1455, 1318, 1233, 1176, 1069, 960, 922, 828, 779, 752 |
| 79 | [structure: dihydro-benzothiazine-S,S-dioxide with (CH₂)₃-piperazine-4-fluorophenyl] | Colorless powdery crystals 103.5–104.0° C. (ethyl acetate-hexane) | (400 MHz) 1.86(2H, m), 2.50(2H, t, J=7.1Hz), 2.60(4H, m), 3.01(2H, t, J=6.3Hz), 3.11(4H, m), 3.26(2H, t, J=7.0Hz), 3.90(2H, t, J=6.3Hz), 6.87(2H, m), 6.95(2H, m), 7.22(1H, d, J=7.7Hz), 7.37(1H, m), 7.44(1H, m), 7.83(1H, d, J=7.8Hz) | (KBr) 2944, 2804, 1513, 1477, 1459, 1330, 1240, 1155, 1012, 929, 822, 785, 766, 712 |
| 80 | [structure: 4-methoxy-saccharin N-CH₂COCH₃] | Colorless needle crystals 147.5–148.5° C. (ethyl acetate-hexane) | (400 MHz) 2.27(3H, s), 4.05(3H, s), 4.40(2H, s), 7.29(1H, d, J=7.9Hz), 7.49(1H, d, J=7.9Hz), 7.82(1H, t, J=7.9Hz) | (KBr) 1740, 1718, 1599, 1582, 1486, 1439, 1283, 1221, 1165, 1041, 998, 867, 798, 679 |
| 81 | [structure: 4-chloro-saccharin N-CH₂COCH₃] | Colorless prism crystals 179.0–181.0° C. (ethyl acetate-hexane) | (400 MHz) 2.29(3H, s), 4.47(2H, s), 7.78–7.83(2H, m), 7.86(1H, m) | (KBr) 3092, 1750, 1732, 1578, 1452, 1348, 1032, 1182, 1005, 988, 801, 699 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 82 | MeO-benzisothiazolone-NCH₂COCH₃ | Colorless needle crystals 166.0–167.0° C. (ethyl acetate-hexane) | (270 MHz) 2.28(3H, s), 3.96(3H, s), 4.45(2H, s), 7.33(1H, dd, J=2.6Hz, 8.6Hz), 7.51(1H, d, J=2.6Hz), 7.83(1H, d, J=8.6Hz) | (KBr) 1740, 1724 1610, 1484 1329, 1307 1186, 1013 829 |
| 83 | Cl-benzisothiazolone-NCH₂COCH₃ | Pale yellow prism crystals 154.0–154.5° C. (methanol) | (270 MHz) 2.29(3H, s), 4.47(2H, s), 7.82–7.93(2H, m), 8.06(1H, d, J=2.0Hz) | (KBr) 1751, 1734 1421, 1331 1298, 1186 1084, 818 |
| 84 | MeO-benzisothiazolone-NCH₂COCH₃ | Colorless needle crystals 186.5–188.0° C. (ethyl acetate-hexane) | (270 MHz) 2.28(3H, s), 3.98(3H, s), 4.44(2H, s), 7.29(1H, dd, J=2.6Hz, 8.6Hz), 7.37(1H, d, J=2.6Hz), 7.98(1H, d, J=8.6Hz) | (KBr) 1740, 1722 1600, 1494 1325, 1178 1020, 847 762, 689 668 |
| 85 | Cl-benzisothiazolone-NCH₂COCH₃ | Colorless needle crystals 184.5–185.0° C. (ethyl acetate-hexane) | (270 MHz) 2.29(3H, s), 4.47(2H, s), 7.82(1H, dd, J=2.0Hz, 8.6Hz), 7.93(1H, d, J=2.0Hz), 8.03(1H, d, J=8.6Hz) | (KBr) 1750, 1723 1592, 1335 1198, 1097 1052, 1003 864, 670 |
| 86 | OMe/OH benzothiazine-COCH₃ | Pale ocherous needle crystals 206.5–208.0° C. (ethyl acetate-hexane) | (400 MHz) 2.41(3H, s), 4.00(3H, s), 5.89(1H, bs), 7.24(1H, d, J=7.9Hz), 7.50(1H, d, J=7.9Hz), 7.67(1H, t, J=7.9Hz), 15.41(1H, bs) | (KBr) 1605, 1580 1474, 1382 1190, 1175 1158, 1038 928, 800 716 |

TABLE 1-continued

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 87 | (structure: 4-OH, 3-COCH₃, Cl-substituted benzothiazine-S,S-dioxide, NH) | Pale brown prism crystals 159.5–161.0° C. (ethyl acetate-hexane) | (400 MHz) 2.42(3H, s), 5.84(1H, bs), 7.61(1H, t, J=7.9Hz), 7.73(1H, dd, J=1.1Hz, 7.9Hz), 7.82(1H, dd, J=1.1Hz, 7.9Hz), 15.72(1H, s) | (KBr) 3212, 1626 1577, 1540 1436, 1376 1334, 1181 1159, 926 798 |
| 88 | (structure: 4-OH, 3-COCH₃, MeO-substituted benzothiazine-S,S-dioxide, NH) | Colorless needle crystals 187.0–183.0° C. (ethyl acetate-hexane) | (400 MHz) 2.43(3H, s), 3.93(3H, s), 5.79(1H, bs), 7.19(1H, dd, J=2.6Hz, 8.6Hz), 7.57(1H, d, J=2.6Hz), 7.80(1H, d, J=8.6Hz), 15.10(1H, bs) | (KBr) 3178, 1561 1390, 1328 1236, 1179 1069, 906 834, 744 |
| 89 | (structure: 4-OH, 3-COCH₃, Cl-substituted benzothiazine-S,S-dioxide, NH) | Yellow prism crystals 229.0–231.0° C. (ethanol-water) | (270 MHz) 2.45(3H, s), 5.97(1H, s), 7.70(1H, dd, J=7.9Hz, 2.0Hz), 7.84(1H, d, J=7.9Hz), 8.11(1H, d, J=2.0Hz), 14.84(1H, s) | (KBr) 3194, 1591 1552, 1395 1327, 1181 1097, 912 726, 652 |
| 90 | (structure: 4-OH, 3-COCH₃, MeO-substituted benzothiazine-S,S-dioxide, NH) | Pale ocherous needle crystals 162.5–163.5° C. (ethyl acetate-hexane) | (270 MHz) 2.40(3H, s), 3.94(3H, s), 5.95(1H, s), 7.20(1H, dd, J=2.6Hz, 8.6Hz), 7.33(1H, d, J=2.6Hz), 8.06(1H, d, J=8.6Hz), 15.10(1H, bs) | (KBr) 1598, 1544 1495, 1386 1327, 1275 1230, 1177 1058, 1024 900, 840 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 91 | (structure: 4-OH, 3-acetyl, 7-Cl benzothiazine dioxide) | Yellow needle crystals 216.0–217.5° C. (decomposed) (ethanol-water) | (270 MHz) 2.44(3H, s), 6.01(1H, bs), 7.70(1H, dd, J=2.0Hz, 8.6Hz), 7.86(1H, d, J=2.0Hz), 8.08(1H, d, J=8.6Hz), 14.93(1H, bs) | (KBr) 3176, 1638 1589, 1538 1374, 1315 1178, 1102 836, 680 |
| 92 | (structure: MeO-substituted spiro dioxolane benzothiazine) | Colorless needle crystals 254.0–256.0° C. (acetonitrile) | (400 MHz)(DMSO-d₆/TMS) 3.54(2H, b), 3.84(3H, s), 4.04(2H, m), 4.18(2H, m), 7.25(1H, d, J=8.0Hz), 7.28(1H, d, J=8.0Hz), 7.55(1H, t, J=8.0Hz), 8.34(1H, b) | (KBr) 2980–2800 1591, 1469 1435, 1324 1276, 1207 1160, 1048 992, 946 919, 837 790, 742 |
| 93 | (structure: Cl-substituted spiro dioxolane benzothiazine) | Colorless prism crystals 233.0–234.0° C. (acetonitrile) | (400 MHz)(DMSO-d₆/TMS) 3.65(2H, d, J=5.8Hz), 4.16(2H, m), 4.29(2H, m), 7.61(1H, t, J=7.7Hz), 7.73(2H, d, J=7.7Hz), 8.59(1H, b) | (KBr) 3268, 3080 2908, 1582 1434, 1417 1322, 1271 1157, 1071 1048, 995 948, 830 799 |
| 94 | (structure: MeO-substituted spiro dioxolane benzothiazine isomer) | Colorless prism crystals 152.0–153.0° C. (acetonitrile) | (270 MHz) 3.69(2H, d, J=7.9Hz), 3.87(3H, s), 4.16(2H, m), 4.26(2H, m), 5.11(1H, bt, J=7.9Hz), 6.99(1H, d, J=2.6Hz), 7.02(1H, dd, J=2.6Hz, 8.6Hz), 7.73(1H, d, J=8.6Hz) | (KBr) 3260, 1596 1486, 1448 1404, 1314 1244, 1155 1044, 951 872, 826 752, 699 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 95 | (dioxolane-spiro benzosultam, Cl-substituted) | Colorless prism crystals 156.0–157.0° C. (ethyl acetate-hexane) | (270 MHz) 3.71(2H, d, J=7.3Hz), 4.17(2H, m), 4.29(2H, m), 5.18(1H, m), 7.47–7.52(2H, m), 7.72(1H, d, J=9.2Hz) | (KBr) 3238, 1587 1430, 1329 1259, 1164 1100, 1040 946, 829 712 |
| 96 | (dioxolane-spiro benzosultam, MeO-substituted) | Colorless needle crystals 131.0–131.5° C. (ethyl acetate-hexane) | (270 MHz) 3.70(2H, d, J=7.9Hz), 3.86(3H, s), 4.14(2H, m), 4.25(2H, m), 5.17(1H, m), 7.09(1H, dd, J=2.6Hz, 8.6Hz), 7.22(1H, d, J=2.6Hz), 7.45(1H, d, J=8.6Hz) | (KBr) 3186, 1608 1502, 1320 1242, 1151 1038, 829 742, 690 678 |
| 97 | (dioxolane-spiro benzosultam, Cl-substituted) | Colorless needle crystals 171.0–172.0° C. (ethyl acetate-hexane) | (270 MHz) 3.71(2H, d, J=7.9Hz), 4.16(2H, m), 4.26(2H, m), 5.22(1H, m), 7.48(1H, d, J=8.6Hz), 7.53(1H, dd, J=2.0Hz, 8.6Hz), 7.76(1H, d, J=2.0Hz) | (KBr) 3191, 1592 1481, 1436 1327, 1160 1096, 1037 949, 920 830, 809 748, 692 |
| 98 | (oxo-benzosultam, Cl-substituted) | Colorless prism crystals 183.0–185.5° C. (ethanol) | (400 MHz) 4.36(2H, d, J=7.5Hz), 5.29(1H, b), 7.66(1H, t, J=8.0Hz), 7.74(1H, dd, J=1.2Hz, 8.0Hz), 7.84(1H, dd, J=1.2Hz, 8.0Hz) | (KBr) 3259, 1699 1405, 1340 1246, 1201 1176, 854 799 |

TABLE 1-continued

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 99 | (spiro dithiolane benzo sultam with Cl) | Colorless powdery crystals 228.5–229.5° C. (chloroform-hexane) | (400 MHz) 3.46(2H, m), 3.69(2H, m), 3.98(2H, d, J=7.9Hz), 5.40(1H, b), 7.41(1H, t, J=8.0Hz), 7.62(1H, dd, J=1.3Hz, 8.0Hz), 7.80(1H, dd, J=1.3Hz, 8.0Hz) | (KBr) 3250, 1322 1177, 1070 792, 714 |
| 100 | (spiro dioxolane benzo sultam N-(CH$_2$)$_2$-Cl, MeO) | Colorless prism crystals 172.0–173.0° C. (ethyl acetate-hexane) | (400 MHz) 3.71(2H, m), 3.75(2H, m), 3.89(3H, s), 3.93(2H, s), 4.12(2H, m), 4.31(2H, m), 7.12(1H, d, J=8.0Hz), 7.41(1H, dd, J=1.1Hz, 8.0Hz), 7.48(1H, t, J=8.0Hz) | (KBr) 1591, 1463 1431, 1324 1275, 1152 1090, 1048 998, 946 896, 843 794, 746 |
| 101 | (spiro dioxolane benzo sultam N-(CH$_2$)$_3$-Cl, MeO) | Colorless prism crystals 129.0–131.0° C. (ethyl acetate-hexane) | (400 MHz) 2.10(2H, m), 3.60(2H, t, J=6.5Hz), 3.70(2H, t, J=6.2Hz), 3.85(2H, s), 3.89(3H, s), 4.13(2H, m), 4.31(2H, m), 7.11(1H, d, J=8.2Hz), 7.42(1H, d, J=8.2Hz), 7.48(1H, t, J=8.2Hz) | (KBr) 1590, 1464 1431, 1327 1276, 1154 1061, 1047 957, 942 795, 753 |
| 102 | (spiro dioxolane benzo sultam N-(CH$_2$)$_3$-Cl, Cl) | Colorless prism crystals 100.5–101.0° C. (ethyl acetate-hexane) | (400 MHz) 2.10(2H, m), 3.61(2H, t, J=6.3Hz), 3.71(2H, t, J=6.1Hz), 3.90(2H, s), 4.21(2H, m), 4.44(2H, m), 7.46(1H, t, J=8.0Hz), 7.61(1H, dd, J=1.1Hz, 8.0Hz), 7.77(1H, dd, J=1.1Hz, 8.0Hz) | (KBr) 1582, 1335 1163, 1099 1056, 1037 950, 810 750 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 103 | MeO-substituted spiro-dioxolane benzothiazine with N-(CH₂)₃-Cl | Colorless prism crystals 112.5–113.0° C. (ethyl acetate-hexane) | (270 MHz) 2.10(2H, m), 3.60(2H, t, J=5.9Hz), 3.72(2H, t, J=5.9Hz), 3.86(3H, s), 3.89(2H, s), 4.18(2H, m), 4.28(2H, m), 6.96(1H, d, J=2.6Hz), 7.02(1H, dd, J=2.6Hz, 9.2Hz), 7.73(1H, d, J=9.2Hz) | (KBr) 2977, 1608 1573, 1483 1424, 1326 1231, 1148 1047, 999 945, 895 818, 716 |
| 104 | Cl-substituted spiro-dioxolane benzothiazine with N-(CH₂)₃-Cl | Colorless prism crystals 94.0–94.5° C. (ethyl acetate-hexane) | (270 MHz) 2.10(2H, m), 3.61(2H, t, J=6.6Hz), 3.71(2H, t, J=5.9Hz), 3.90(2H, s), 4.19(2H, m), 4.30(2H, m), 7.47~7.71(2H, m), 7.73(1H, d, J=7.3Hz) | (KBr) 2984, 2895 1588, 1460 1444, 1342 1241, 1151 1105, 1056 956, 950 810, 771 728, 703 |
| 105 | MeO-substituted spiro-dioxolane benzothiazine with N-(CH₂)₃-Cl | Colorless prism crystals 99.0–100.5° C. (ethyl acetate-hexane) | (270 MHz) 2.11(2H, m), 3.61(2H, t, J=6.6Hz), 3.71(2H, t, J=5.9Hz), 3.86(3H, s), 3.88(2H, s), 4.15(2H, m), 4.26(2H, m), 7.09(1H, dd, J=2.6Hz, 8.6Hz), 7.21(1H, d, J=2.6Hz), 7.43(1H, d, J=8.6Hz) | (KBr) 2966, 2897 1607, 1500 1324, 1156 1034, 939 860, 828 709, 660 |
| 106 | Cl-substituted spiro-dioxolane benzothiazine with N-(CH₂)₃-Cl | Colorless prism crystals 87.5–88.5° C. (ethyl acetate-hexane) | (270 MHz) 2.10(2H, m), 3.61(2H, t, J=6.6Hz), 3.71(2H, t, J=6.6Hz), 3.90(2H, s), 4.18(2H, m), 4.27(2H, m), 7.45(1H, d, J=8.6Hz), 7.53(1H, dd, J=2.0Hz, 8.6Hz), 7.76(1H, d, J=2.0Hz) | (KBr) 3066, 2956 1591, 1472 1448, 1328 1159, 1102 1046, 999 943, 827 696 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 107 | MeO-[benzene ring fused to sultam with C=O]-N(CH₂)₃—Cl, SO₂ | Pale yellow oil | (400 MHz) 2.07(2H, m), 3.35(2H, t, J=6.7Hz), 3.63(2H, t, J=6.2Hz), 3.99(3H, s), 4.29(2H, s), 7.27(1H, d, J=7.6Hz), 7.48(1H, d, J=7.6Hz), 7.72(1H, t, J=7.6Hz) | (film) 2947, 1694 1588, 1567 1471, 1434 1338, 1280 1154, 1088 1042, 870 797, 735 |
| 108 | MeO-[benzene fused to sultam with dithiolane spiro]-N(CH₂)₃—Cl, SO₂ | Colorless needle crystals 138.5–139.0° C. (ethyl acetate-hexane) | (400 MHz) 2.18(2H, m), 3.43(2H, m), 3.61(2H, m), 3.69(2H, t, J=6.4Hz), 3.74(2H, t, J=6.2Hz), 3.94(3H, s), 4.04(2H, s), 7.10(1H, dd, J=1.4Hz, 8.0Hz), 7.41~7.49(2H, m) | (KBr) 2916, 1588 1464, 1434 1301, 1271 1164, 1141 1120, 1055 1032, 955 865, 793 762, 726 |
| 109 | MeO-[benzene fused to sultam with dioxolane spiro]-N(CH₂)₃-N-piperazine-N-(4-F-phenyl), SO₂ | Colorless needle crystals 146.5–147.5° C. (ethyl acetate-hexane) | (400 MHz) 2.66(4H, m), 2.71(2H, t, J=6.6Hz), 3.09(4H, m), 3.59(2H, t, J=6.6Hz), 3.88(3H, s), 3.95(2H, s), 4.11(2H, m), 4.30(2H, m), 6.85(2H, m), 6.94(2H, m), 7.10(1H, dd, J=1.3Hz, 8.0Hz), 7.40~7.53(2H, m) | (KBr) 1589, 1510 1372, 1333 1279, 1232 1154, 1052 996, 932 828, 752 738 |
| 110 | MeO-[benzene fused to sultam with dioxolane spiro]-N(CH₂)₃-N-piperazine-N-(4-F-phenyl), SO₂ | Pale yellow prism crystals 174.0–175.0° C. (ethyl acetate-hexane) | (400 MHz) 1.85(2H, m), 2.49(2H, t, J=7.1Hz), 2.61(4H, m), 3.12(4H, m), 3.50(2H, t, J=6.8Hz), 3.86(2H, s), 3.89(3H, s), 4.11(2H, m), 4.30(2H, m), 6.85~6.89(2H, m), 6.92~6.98(2H, m), 7.10(1H, d, J=8.0Hz), 7.43(1H, d, J=8.0Hz), 7.48(1H, d, J=8.0Hz) | (KBr) 2822, 1589 1511, 1468 1322, 1274 1232, 1150 1053, 998 955, 832 740, 673 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 111 | (spiro-dioxolane fused benzothiazine dioxide with MeO substituent, -(CH$_2$)$_3$-N-piperidine-N-C$_6$H$_4$-OH) | Pale ocherous needle crystals 191.0–192.5° C. (2-propanol) | (400 MHz) 1.85(2H, m), 2.49(2H, t, J=7.1Hz), 2.61(4H, m), 3.08(4H, m), 3.50(2H, t, J=6.8Hz), 3.85(2H, s), 3.88(3H, s), 4.10(2H, m), 4.29(2H, m), 6.75(2H, d, J=8.8Hz), 6.84(2H, d, J=8.8Hz), 7.10(1H, d, J=8.0Hz), 7.43(1H, d, J=8.0Hz), 7.48(1H, t, J=8.0Hz) | (KBr) 2900–2500 1589, 1514 1468, 1438 1332, 1276 1227, 1152 1051, 928 825, 741 |
| 112 | (spiro-dioxolane fused benzothiazine dioxide with MeO substituent, -(CH$_2$)$_3$-N-piperidine-C(=O)-C$_6$H$_4$-F) | Colorless amorphous | (400 MHz) 1.80–1.90(6H, m), 2.09(2H, m), 2.46(2H, t, J=7.1Hz), 3.00(2H, m), 3.21(1H, m), 3.48(2H, t, J=6.8Hz), 3.86(2H, s), 3.89(3H, s), 4.13(2H, m), 4.30(2H, m), 7.09–7.16(3H, m), 7.42–7.50(2H, m), 7.95(2H, m) | (KBr) 2942, 1682 1598, 1508 1470, 1274 1153, 1050 952, 850 734, 672 |
| 113 | (spiro-dioxolane fused benzothiazine dioxide with Cl substituent, -(CH$_2$)$_3$-N-piperidine-N-C$_6$H$_4$-F) | Colorless prism crystals 186.0–187.0° C. (ethyl acetate-hexane) | (400 MHz) 1.85(2H, m), 2.50(2H, t, J=7.1Hz), 2.62(4H, m), 3.12(4H, m), 3.51(2H, t, J=6.8Hz), 3.91(2H, s), 4.19(2H, m), 4.42(2H, m), 6.87(2H, m), 6.96(2H, m), 7.46(1H, t, J=7.9Hz), 7.60(1H, dd, J=1.2Hz, 7.9Hz), 7.77(1H, dd, J=1.2Hz, 7.9Hz) | (KBr) 2954, 2818 1506, 1333 1226, 1168 1041, 1001 967, 830 798, 737 |
| 114 | (spiro-dioxolane fused benzothiazine dioxide with Cl substituent, -(CH$_2$)$_3$-N-piperidine-N-C$_6$H$_4$-OH) | Pale green needle crystals 212.5–213.5° C. (ethanol) | (400 MHz) 1.85(2H, m), 2.50(2H, t, J=7.1Hz), 2.62(4H, m), 3.08(4H, m), 3.51(2H, t, J=6.8Hz), 3.91(2H, s), 4.19(2H, m), 4.42(2H, m), 6.75(2H, d, J=8.9Hz), 6.84(2H, d, J=8.9Hz), 7.45(1H, t, J=7.9Hz), 7.60(1H, dd, J=1.3Hz, 7.9Hz), 7.77(1H, dd, J=1.3Hz, 7.9Hz) | (KBr) 3079, 2966 2822, 1515 1439, 1336 1241, 1175 1162, 1050 996, 920 827, 742 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 115 | (structure: MeO-substituted benzo-fused spiro-dioxolane sulfonamide with -(CH₂)₃-N-piperazine-4-fluorophenyl) | Colorless prism crystals 110.5–111.5° C. (ethyl acetate-hexane) | (270 MHz) 1.85(2H, m), 2.50(2H, t, J=7.3Hz), 2.62(4H, m), 3.12(4H, m), 3.50(2H, t, J=6.6Hz), 3.86(3H, s), 3.89(2H, s), 4.15(2H, m), 4.27(2H, m), 6.84~7.03(6H, m), 7.74(1H, d, J=8.6Hz) | (KBr) 2943, 2826 1597, 1512 1328, 1230 1152, 1042 947, 818 714 |
| 116 | (structure: MeO-substituted benzo-fused spiro-dioxolane sulfonamide with -(CH₂)₃-N-piperidine-C(O)-4-fluorophenyl) | Colorless prism crystals 107.0–108.0° C. (ethyl acetate-hexane) | (270 MHz) 1.72–1.90(6H, m), 2.09(2H, m), 2.47(2H, t, J=6.6Hz), 3.00(2H, m), 3.21(1H, m), 3.48(2H, t, J=6.6Hz), 3.86(3H, s), 3.90(2H, s), 4.18(2H, m), 4.27(2H, m), 6.95(1H, d, J=2.6Hz), 7.01(1H, dd, J=2.6Hz, 8.6Hz), 7.14(2H, m), 7.73(1H, d, J=8.6Hz), 7.97(2H, m) | (KBr) 2940, 1672 1599, 1480 1372, 1155 1045, 949 834, 734 708 |
| 117 | (structure: Cl-substituted benzo-fused spiro-dioxolane sulfonamide with -(CH₂)₃-N-piperazine-4-fluorophenyl) | Pale yellow oil | (270 MHz) 1.85(2H, m), 2.50(2H, t, J=7.3Hz), 2.61(4H, m), 3.12(4H, m), 3.51(2H, t, J=7.3Hz), 3.91(2H, s), 4.16(2H, m), 4.29(2H, m), 6.85~7.01(4H, m), 7.45~7.50(2H, m), 7.73(1H, d, J=7.9Hz) | (film) 2949, 2820 1510, 1456 1335, 1234 1158, 1051 952, 818 705 |
| 118 | (structure: Cl-substituted benzo-fused spiro-dioxolane sulfonamide with -(CH₂)₃-N-piperidine-C(O)-4-fluorophenyl) | Colorless needle crystals 149.5–150.5° C. (ethyl acetate-hexane) | (270 MHz) 1.72–1.90(6H, m), 2.09(2H, m), 2.46(2H, t, J=6.6Hz), 2.99(2H, m), 3.21(1H, m), 3.50(2H, t, J=6.6Hz), 3.92(2H, s), 4.19(2H, m), 4.30(2H, m), 7.14(2H, m), 7.46~7.49(2H, m), 7.72(1H, d, J=9.2Hz), 7.97(2H, m) | (KBr) 2962, 1673 1595, 1505 1370, 1308 1236, 1156 1050, 948 853, 832 702 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 119 | (MeO-substituted benzosultam spiro-dioxolane with -(CH₂)₃-N-piperazine-4-fluorophenyl) | Colorless needle crystals 140.0–140.5° C. (ethyl acetate-hexane) | (270 MHz) 1.86(2H, m), 2.50(2H, t, J=6.6Hz), 2.62(4H, m), 3.12(4H, m), 3.51(2H, t, J=6.6Hz), 3.86(3H, s), 3.89(2H, s), 4.13(2H, m), 4.24(2H, m), 6.85–6.96(4H, m), 7.08(1H, dd, J=2.6Hz, 9.2Hz), 7.23(1H, d, J=2.6Hz), 7.41(1H, d, J=9.2Hz) | (KBr) 2950, 2827 1608, 1511 1326, 1274 1226, 1149 1031, 996 953, 879 823, 710 |
| 120 | (MeO-substituted benzosultam spiro-dioxolane with -(CH₂)₃-N-piperidine-C(=O)-4-fluorophenyl) | Colorless prism crystals 146.0–146.5° C. (ethyl acetate-hexane) | (270 MHz) 1.78–1.88(6H, m), 2.10(2H, m), 2.47(2H, t, J=6.6Hz), 3.00(2H, m), 3.21(1H, m), 3.50(2H, t, J=6.6Hz), 3.86(3H, s), 3.90(2H, s), 4.15(2H, m), 4.26(2H, m), 7.06~7.17(3H, m), 7.22(1H, d, J=2.6Hz), 7.42(1H, d, J=8.6Hz), 7.96(2H, m) | (KBr) 2955, 2720 1676, 1600 1509, 1472 1326, 1148 998, 949 851, 735 700 |
| 121 | (Cl-substituted benzosultam spiro-dioxolane with -(CH₂)₃-N-piperazine-4-fluorophenyl) | Colorless needle crystals 134.0–135.0° C. (ethyl acetate-hexane) | (270 MHz) 1.85(2H, m), 2.50(2H, t, J=6.6Hz), 2.61(4H, m), 3.12(4H, m), 3.52(2H, t, J=6.6Hz), 3.90(2H, s), 4.15(2H, m), 4.26(2H, m), 6.85–6.99(4H, m), 7.43(1H, d, J=8.6Hz), 7.52(1H, dd, J=2.0Hz, 8.6Hz), 7.76(1H, d, J=2.0Hz) | (KBr) 2832, 1509 1332, 1232 1162, 1104 1042, 944 825, 700 |
| 122 | (Cl-substituted benzosultam spiro-dioxolane with -(CH₂)₃-N-piperidine-C(=O)-4-fluorophenyl) | Colorless prism crystals 105.5–106.5° C. (ethyl acetate-hexane) | (270 MHz) 1.78–1.89(6H, m), 2.10(2H, m), 2.46(2H, t, J=6.6Hz), 2.99(2H, m), 3.22(1H, m), 3.50(2H, t, J=6.6Hz), 3.92(2H, s), 4.17(2H, m), 4.27(2H, m), 7.14(2H, m), 7.44(1H, d, J=8.6Hz), 7.52(1H, dd, J=2.0Hz, 8.6Hz), 7.76(1H, d, J=2.0Hz), 7.96(2H, m) | (KBr) 2869, 2776 1676, 1592 1506, 1329 1224, 1165 1098, 1045 974, 836 696 |

TABLE 1-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 123 | (MeO-substituted spiro dithiolane benzosulfonamide with -(CH$_2$)$_3$-N-piperazine-4-fluorophenyl) | Colorless plate crystals 129.0–130.0° C. (methanol) | (400 MHz) 1.93(2H, m), 2.53(2H, t, J=7.1Hz), 2.63(4H, m), 3.12(4H, m), 3.41(2H, m), 3.57–3.63(4H, m), 3.94(3H, s), 4.06(2H, s), 6.86(2H, m), 6.95(2H, m), 7.09(1H, dd, J=1.2Hz, 8.1Hz), 7.40–7.49(2H, m) | (KBr) 2944, 2832 1586, 1510 1466, 1431 1336, 1274 1232, 1152 1051, 916 812, 791 703 |
| 124 | (Cl-substituted spiro dithiolane benzosulfonamide with -(CH$_2$)$_3$-N-piperazine-4-fluorophenyl) | Colorless prism crystals 119.5–121.0° C. (ethyl acetate-hexane) | (400 MHz) 1.92(2H, quint, J=6.9Hz), 2.54(2H, t, J=6.9Hz), 2.62(4H, m), 3.12(4H, m), 3.46(2H, m), 3.64(2H, t, J=6.7Hz), 3.71(2H, m), 4.09(2H, s), 6.87(2H, m), 6.95(2H, m), 7.39(1H, t, J=8.0Hz), 7.59(1H, dd, J=1.4Hz, 8.0Hz), 7.83(1H, dd, J=1.4Hz, 8.0Hz) | (KBr) 2941, 2819 1511, 1436 1331, 1235 1166, 937 817, 776 712 |

*: Measured in CDCl$_3$ with TMS as an internal standard unless otherwise specifically indicated.

EXAMPLE 125

Following the process described in Example 110 or Example 111 or a process similar to it, the following compounds can each be obtained using as a benzothiazine derivative, besides 2-(3-chloropropyl)-5-methoxy-3,4-dihydro-2H-1,2-benzothiazin-4-one 1,1-dioxide ethylene acetal (Compound No. 101), 2-(2-chloroethyl)-5-methoxy-3,4-dihydro-2H-1,2-benzothiazin-4-one 1,1-dioxide ethylene acetal, 2-(4-chlorobutyl)-5-methoxy-3,4-dihydro-2H-1,2-benzothiazin-4-one 1,1-dioxide ethylene acetal, 2-(3-chloropropyl)-5-methoxy-3,4-dihydro-2H-1,2-benzothiazine-4-spiro-2'-(1',3'-dithiolane) 1,1-dioxide, 2-(2-chloroethyl)-5-methoxy-3,4-dihydro-2H-1,2-benzothiazine-4-spiro-2'-(1',3'-dithiolane) 1,1-dioxide, 2-(4-chlorobutyl)-5-methoxy-3,4-dihydro-2H-1,2-benzothiazine-4-spiro-2'-(1',3'-dithiolane) 1,1-dioxide, 2-(3-chloropropyl)-4,4,5-trimethoxy-3,4-dihydro-2H-1,2-benzothiazine 1,1-dioxide, 2-(2-chloroethyl)-4,4,5-trimethoxy-3,4-dihydro-2H-1,2-benzothiazine 1,1-dioxide, 2-(4-chlorobutyl)-4,4,5-trimethoxy-3,4-dihydro-2H-1,2-benzothiazine 1,1-dioxide, 2-(3-chloropropyl)-5-methoxy-3,4-dihydro-2H-1,2-benzothiazine-4-spiro-2'-(1',3'-dioxane) 1,1-dioxide, 2-(3-chloropropyl)-5-methoxy-3,4-dihydro-2H-1,2-benzothiazine-4-spiro-2'-(1',3'-dithiane) 1,1-dioxide, 2-(3-chloropropyl)-4,4-bis(ethylthio)-5-methoxy-3,4-dihydro-2H-1,2-benzothiazine 1,1-dioxide, 2-(3-chloropropyl)-5-methoxy-3,4-dihydro-2H-1,2-benzothiazine-4-one 1,1-dioxide, 2-(3-chloropropyl)-4-hydroxyimino-5-methoxy-3,4-dihydro-2H-1,2-benzothiazine 1,1-dioxide, 2-(3-chloropropyl)-4-hydroxy-5-methoxy-3,4-dihydro-2H-1,2-benzothiazine 1,1-dioxide, 2-(2-chloroethyl)-4-hydroxy-5-methoxy-3,4-dihydro-2H-1,2-benzothiazine 1,1-dioxide, 2-(4-chlorobutyl)-4-hydroxy-5-methoxy-3,4-dihydro-2H-1,2-benzothiazine 1,1-dioxide, 2-(3-chloropropyl)-4,5-dimethoxy-2H-1,2-benzothiazine 1,1-dioxide, 2-(3-chloropropyl)-4,5-dimethoxy-3,4-dihydro-2H-1,2-benzothiazine 1,1-dioxide, 2-(2-chloroethyl)-4,5-dimethoxy-3,4-dihydro-2H-1,2-benzothiazine 1,1-dioxide, 2-(4-chlorobutyl)-4,5-dimethoxy-3,4-dihydro-2H-1,2-benzothiazine 1,1-dioxide, 2-(3-chloropropyl)-4-ethoxy-5-methoxy-3,4-dihydro-2H-1,2-benzothiazine 1,1-dioxide, 4-benzyloxy-2-(3-chloropropyl)-5-methoxy-3,4-dihydro-2H-1,2-benzothiazine 1,1-dioxide, 2-(3-chloropropyl)-5-methoxy-2H-1,2-benzothiazine 1,1-dioxide or 2-(3-chloropropyl)-5-methoxy-3,4-dihydro-2H-1,2-benzothiazine 1,1-dioxide and as a piperazine derivative or piperidine derivative, 1-phenylpiperazine, 1-(2-fluorophenyl)piperazine, 1-(4-fluorophenyl)piperazine, 1-(4-hydroxyphenyl)piperazine, 1-(3-methoxyphenyl)piperazine, 1-(2-pyridyl)piperazine or 4-(4-fluorobenzoyl)piperidine.

Further, modifications to the substituted benzothiazine derivatives as raw materials and the treatments in the Examples make it possible to obtain corresponding compounds. For such modifications, the disclosure of PCT International Application No. PCT/JP94/02194 (now WO 95/18117) will be very useful.

(1) 2-[3-[4-(2-fluorophenyl)piperazin-1-yl]propyl]-5-methoxy-3,4-dihydro-2H-1,2-benzothiazin-4-one 1,1-dioxide ethylene acetal
(2) 2-[4-[4-(4-fluorophenyl)piperazin-1-yl]butyl]-5-methoxy-3,4-dihydro-2H-1,2-benzothiazin-4-one 1,1-dioxide ethylene acetal
(3) 5-methoxy-2-[3-(4-phenylpiperazin-1-yl)propyl]-3,4-dihydro-2H-1,2-benzothiazin-4-one 1,1-dioxide ethylene acetal
(4) 5-methoxy-2-[3-[4-(3-methoxyphenyl)piperazin-1-yl]-propyl]-3,4-dihydro-2H-1,2-benzothiazin-4-one 1,1-dioxide ethylene acetal
(5) 5-methoxy-2-[3-[4-(2-pyridyl)piperazin-1-yl]-propyl]-3,4-dihydro-2H-1,2-benzothiazin-4-one 1,1-dioxide ethylene acetal
(6) 2-[3-[4-(4-hydroxyphenyl)piperazin-1-yl]propyl]-5-methoxy-3,4-dihydro-2H-1,2-benzothiazine-4-spiro-2'-(1',3'-dithiolane) 1,1-dioxide
(7) 2-[3-[4-(4-fluorobenzoyl)piperidino]propyl]-5-methoxy-3,4-dihydro-2H-1,2-benzothiazine-4-spiro-2'-(1',3'-dithiolane) 1,1-dioxide
(8) 2-[3-[4-(2-fluorophenyl)piperazin-1-yl]propyl]-5-methoxy-3,4-dihydro-2H-1,2-benzothiazine-4-spiro-2'-(1',3'-dithiolane) 1,1-dioxide
(9) 2-[2-[4-(4-fluorophenyl)piperazin-1-yl]ethyl]-5-methoxy-3,4-dihydro-2H-1,2-benzothiazine-4-spiro-2'-(1',3'-dithiolane) 1,1-dioxide
(10) 2-[4-[4-(4-fluorophenyl)piperazin-1-yl]butyl]-5-methoxy-3,4-dihydro-2H-1,2-benzothiazine-4-spiro-2'-(1',3'-dithiolane) 1,1-dioxide
(11) 5-methoxy-2-[3-[4-(2-pyridyl)piperazin-1-yl]-propyl]-3,4-dihydro-2H-1,2-benzothiazine-4-spiro-2'-(1',3'-dithiolane) 1,1-dioxide
(12) 2-[3-[4-(4-fluorophenyl)piperazin-1-yl]propyl]-4,4,5-trimethoxy-3,4-dihydro-2H-1,2-benzothiazine 1,1-dioxide
(13) 2-[3-[4-(4-fluorobenzoyl)piperidino]propyl]-4,4,5-trimethoxy-3,4-dihydro-2H-1,2-benzothiazine 1,1-dioxide
(14) 2-[3-[4-(2-fluorophenyl)piperazin-1-yl]propyl]-4,4,5-trimethoxy-3,4-dihydro-2H-1,2-benzothiazine 1,1-dioxide
(15) 2-[2-[4-(4-fluorophenyl)piperazin-1-yl]ethyl]-4,4,5-trimethoxy-3,4-dihydro-2H-1,2-benzothiazine 1,1-dioxide
(16) 2-[4-[4-(4-fluorophenyl)piperazin-1-yl]butyl]-4,4,5-trimethoxy-3,4-dihydro-2H-1,2-benzothiazine 1,1-dioxide
(17) 4,4,5-trimethoxy-2-[3-[4-(2-pyridyl)piperazin-1-yl]propyl]-3,4-dihydro-2H-1,2-benzothiazine 1,1-dioxide
(18) 2-[3-[4-(4-fluorophenyl)piperazin-1-yl]propyl]-5-methoxy-3,4-dihydro-2H-1,2-benzothiazine-4-spiro-2'-(1',3'-dioxane) 1,1-dioxide
(19) 2-[3-[4-(4-fluorobenzoyl)piperidino]propyl]-5-methoxy-3,4-dihydro-2H-1,2-benzothiazine-4-spiro-2'-(1',3'-dioxane) 1,1-dioxide
(20) 2-[3-[4-(2-fluorophenyl)piperazin-1-yl]propyl]-5-methoxy-3,4-dihydro-2H-1,2-benzothiazine-4-spiro-2'-(1',3'-dioxane) 1,1-dioxide
(21) 2-[2-[4-(4-fluorophenyl)piperazin-1-yl]ethyl]-5-methoxy-3,4-dihydro-2H-1,2-benzothiazine-4-spiro-2'-(1',3'-dioxane) 1,1-dioxide
(22) 2-[4-[4-(4-fluorophenyl)piperazin-1-yl]butyl]-5-methoxy-3,4-dihydro-2H-1,2-benzothiazine-4-spiro-2'-(1',3'-dioxane) 1,1-dioxide
(23) 5-methoxy-2-[3-[4-(2-pyridyl)piperazin-1-yl]-propyl]-3,4-dihydro-2H-1,2-benzothiazine-4-spiro-2'-(1',3'-dioxane) 1,1-dioxide
(24) 2-[3-[4-(4-fluorophenyl)piperazin-1-yl]propyl]-5-methoxy-3,4-dihydro-2H-1,2-benzothiazine-4-spiro-2'-(1',3'-dithiane) 1,1-dioxide
(25) 2-[3-[4-(4-hydroxyphenyl)piperazin-1-yl]propyl]-5-methoxy-3,4-dihydro-2H-1,2-benzothiazine-4-spiro-2'-(1',3'-dithiane) 1,1-dioxide
(26) 2-[3-[4-(4-fluorobenzoyl)piperidino]propyl]-5-methoxy-3,4-dihydro-2H-1,2-benzothiazine-4-spiro-2'-(1',3'-dithiane) 1,1-dioxide
(27) 4,4-bis(ethylthio)-2-[3-[4-(4-fluorophenyl)-piperazin-1-yl]propyl]-5-methoxy-3,4-dihydro-2H-1,2-benzothiazine 1,1-dioxide

(28) 4,4-bis(ethylthio)-2-[3-[4-(4-hydroxyphenyl)-piperazin-1-yl]propyl]-5-methoxy-3,4-dihydro-2H-1,2-benzothiazine 1,1-dioxide

(29) 4,4-bis(ethylthio)-2-[3-[4-(4-fluorobenzoyl)-piperidino]propyl]-5-methoxy-3,4-dihydro-2H-1,2-benzothiazine 1,1-dioxide

(30) 2-[3-[4-(4-fluorophenyl)piperazin-1-yl]propyl]-5-methoxy-3,4-dihydro-2H-1,2-benzothiazin-4-one 1,1-dioxide

(31) 2-[3-[4-(4-hydroxyphenyl)piperazin-1-yl]propyl]-5-methoxy-3,4-dihydro-2H-1,2-benzothiazin-4-one 1,1-dioxide

(32) 2-[3-[4-(4-fluorobenzoyl)piperidino]propyl]-5-methoxy-3,4-dihydro-2H-1,2-benzothiazin-4-one 1,1-dioxide

(33) 2-[3-[4-(4-fluorophenyl)piperazin-1-yl]propyl]-4-hydroxyimino-5-methoxy-3,4-dihydro-2H-1,2-benzothiazine 1,1-dioxide

(34) 4-hydroxyimino-2-[3-[4-(4-hydroxyphenyl)piperazin-1-yl]propyl]-5-methoxy-3,4-dihydro-2H-1,2-benzothiazine 1,1-dioxide

(35) 2-[3-[4-(4-fluorobenzoyl)piperidino]propyl]-4-hydroxyimino-5-methoxy-3,4-dihydro-2H-1,2-benzothiazine 1,1-dioxide

(36) 2-[3-[4-(4-fluorophenyl)piperazin-1-yl]propyl]-4-hydroxy-5-methoxy-3,4-dihydro-2H-1,2-benzothiazine 1,1-dioxide

(37) 4-hydroxy-2-[3-[4-(4-hydroxyphenyl)piperazin-1-yl]propyl]-5-methoxy-3,4-dihydro-2H-1,2-benzothiazine 1,1-dioxide

(38) 2-[3-[4-(4-fluorobenzoyl)piperidino]propyl]-4-hydroxy-5-methoxy-3,4-dihydro-2H-1,2-benzothiazine 1,1-dioxide

(39) 2-[3-[4-(2-fluorophenyl)piperazin-1-yl]propyl]-4-hydroxy-5-methoxy-3,4-dihydro-2H-1,2-benzothiazine 1,1-dioxide

(40) 2-[2-[4-(4-fluorophenyl)piperazin-1-yl]ethyl]-4-hydroxy-5-methoxy-3,4-dihydro-2H-1,2-benzothiazine 1,1-dioxide

(41) 2-[4-[4-(4-fluorophenyl)piperazin-1-yl]butyl]-4-F hydroxy-5-methoxy-3,4-dihydro-2H-1,2-benzothiazine 1,1-dioxide

(42) 4-hydroxy-5-methoxy-2-[3-[4-(2-pyridyl)piperazin-1-yl]propyl]-3,4-dihydro-2H-1,2-benzothiazine 1,1-dioxide

(43) 2-[3-[4-(4-fluorophenyl)piperazin-1-yl]propyl]-4,5-dimethoxy-2H-1,2-benzothiazine 1,1-dioxide

(44) 2-[3-[4-(4-hydroxyphenyl)piperazin-1-yl]propyl]-4,5-dimethoxy-2H-1,2-benzothiazine 1,1-dioxide

(45) 2-[3-[4-(4-fluorobenzoyl)piperidino]propyl]-4,5-dimethoxy-2H-1, 2-benzothiazine 1,1-dioxide

(46) 2-[3-[4-(2-fluorophenyl)piperazin-1-yl]propyl]-4,5-dimethoxy-2H-1,2-benzothiazine 1,1-dioxide

(47) 2-[3-[4-(4-fluorophenyl)piperazin-1-yl]propyl]-4,5-dimethoxy-3,4-dihydro-2H-1,2-benzothiazine 1,1-dioxide

(48) 2-[3-[4-(4-hydroxyphenyl)piperazin-1-yl]propyl]-4,5-dimethoxy-3,4-dihydro-2H-1,2-benzothiazine 1,1-dioxide

(49) 2-[3-[4-(4-fluorobenzoyl)piperidino]propyl]-4,5-dimethoxy-3,4-dihydro-2H-1,2-benzothiazine 1,1-dioxide

(50) 2-[3-[4-(2-fluorophenyl)piperazin-1-yl]propyl]-4,5-dimethoxy-3,4-dihydro-2H-1,2-benzothiazine 1,1-dioxide

(51) 2-[2-[4-(4-fluorophenyl)piperazin-1-yl]ethyl]-4,5-dimethoxy-3,4-dihydro-2H-1,2-benzothiazine 1,1-dioxide

(52) 2-[4-[4-(4-fluorophenyl)piperazin-1-yl]butyl]-4,5-dimethoxy-3,4-dihydro-2H-1,2-benzothiazine 1,1-dioxide

(53) 4,5-dimethoxy-2-[2-[4-(2-pyridyl)piperazin-1-yl]propyl]-3,4-dihydro-2H-1,2-benzothiazine 1,1-dioxide

(54) 4-ethoxy-2-[3-[4-(4-fluorophenyl)piperazin-1-yl]propyl]-5-methoxy-3,4-dihydro-2H-1,2-benzothiazine 1,1-dioxide

(55) 4-ethoxy-2-[3-[4-(4-hydroxyphenyl)piperazin-1-yl]propyl]-5-methoxy-3,4-dihydro-2H-1,2-benzothiazine 1,1-dioxide

(56) 4-ethoxy-2-[3-[4-(4-fluorobenzoyl)piperidino]-propyl]-5-methoxy-3,4-dihydro-2H-1,2-benzothiazine 1,1-dioxide

(57) 4-benzyloxy-2-[3-[4-(4-fluorophenyl)piperazin-1-yl]propyl]-5-methoxy-3,4-dihydro-2H-1,2-benzothiazine 1,1-dioxide

(58) 4-benzyloxy-2-[3-[4-(4-hydroxyphenyl)piperazin-1-yl]propyl]-5-methoxy-3,4-dihydro-2H-1,2-benzothiazine 1,1-dioxide

(59) 4-benzyloxy-2-[3-[4-(4-fluorobenzoyl)piperidino]-propyl]-5-methoxy-3,4-dihydro-2H-1,2-benzothiazine 1,1-dioxide

(60) 2-[3-[4-(4-fluorophenyl)piperazin-1-yl]propyl]-5-methoxy-2H-1,2-benzothiazine 1,1-dioxide

(61) 2-[3-[4-(4-hydroxyphenyl)piperazin-1-yl]propyl]-5-methoxy-2H-1,2-benzothiazine 1,1-dioxide

(62) 2-[3-[4-(4-fluorobezoyl)piperidino]propyl]-5-methoxy-2H-1,2-benzothiazine 1,1-dioxide

(63) 2-[3-[4-(4-fluorophenyl)piperazin-1-yl]propyl]-5-methoxy-3,4-dihydro-2H-1,2-benzothiazine 1,1-dioxide

(64) 2-[3-[4-(4-hydroxyphenyl)piperazin-1-yl]propyl]-5-methoxy-3,4-dihydro-2H-1,2-benzothiazine 1,1-dioxide

(65) 2-[3-[4-(4-fluorobenzoyl)piperidino]propyl]-5-methoxy-3,4-dihydro-2H-1,2-benzothiazine 1,1-dioxide Test With respect to the compounds of the present invention, their anti-serotonin (5-HT) action and anti-$\alpha_1$ action were investigated by the testing methods which will be described below. The results of some representative compounds are shown in Table 2.

(1) Anti-Serotonin Action (Anti-5-HT Action)

The superior mesenteric artery of each Hartley male guinea pig (body weight: 300–500 g) was excised. A preparation cut in a helical form was suspended under 0.3 g load in a Magnus cylinder filled with the Tyrode solution which had been aerated with a gas mixture of 95% $O_2$+5% $CO_2$ and maintained at 37° C. Using an isometric transducer ("UL-10", manufactured by SHINKOH K.K.) and a pressure preamplifier ("DSA-605A", manufactured by SHINKOH K.K.), variations in tension were measured. The isometric tensions were recorded on a pen-writing recorder ("VP-6537A", manufactured by NATIONAL K.K.). Taking the contraction induced by $10^{-5}$ M serotonin (5-HT) as 100%, the percent contractions in the presence of each test drug at $10^{-7}$ and $10^{-6}$ M were determined as anti-5-HT action.

(2) Anti-$\alpha_1$ Action

The thoracic aorta of each Hartley male guinea pig (body weight: 300–500 g) was excised. A preparation cut in a helical form was suspended under 1 g load in a Magnus cylinder filled with the Tyrode solution which had been aerated with a gas mixture of 95% $O_2$+5% $CO_2$ and maintained at 37° C. Using an isometric transducer ("TB-612J", manufactured by NIHON KOHDEN) and a pressure preamplifier ("AP-620G", manufactured by NIHON KOHDEN), variations in tension were measured. The isometric tensions were recorded on a thermal penwriting recorder ("WT-647G", manufactured by NIHON KOHDEN).

Taking the tonic contraction induced by $10^{-5}$ M norepinephrine (NE) as 100%, the percent contractions upon addition of each test drug at $10^{-8}$ and $10^{-7}$ M were determined as anti-$\alpha_1$ action.

TABLE 2

| Comp'd No. | Anti 5-HT action (% of Control) | | Anti $\alpha_1$ action (% of Control) | |
|---|---|---|---|---|
| | $10^{-7}$ M | $10^{-6}$ M | $10^{-8}$ M | $10^{-7}$ M |
| 35 | 38.3 | 7.5 | 99.0 | 89.3 |
| 37 | 15.7 | 8.3 | 100 | 96.2 |
| 40 | 37.4 | 13.4 | 98.3 | 73.2 |
| 46 | 39.8 | 5.5 | 100 | 97.4 |
| 55 | 23.4 | 7.4 | 100 | 89.2 |
| 56* | 60.8 | 16.9 | 95.4 | 69.5 |
| 57* | 22.0 | 10.0 | 97.3 | 81.6 |
| 62 | 14.1 | 3.3 | 98.1 | 53.1 |
| 64 | 24.8 | 13.8 | 97.3 | 84.9 |
| 66 | 66.6 | 2.8 | 100 | 86.5 |
| 76 | 53.9 | 21.7 | 100 | 88.2 |
| 77 | 45.7 | 18.2 | 100 | 79.6 |
| 109 | 10.5 | NT | 99.3 | 96.1 |
| 110 | 5.6 | NT | 100 | 81.1 |
| 111 | 10.9 | NT | 100.9 | 98.6 |
| 112 | 17.1 | NT | 99.7 | 90.0 |
| 113 | 49.5 | NT | 98.3 | 89.3 |
| 114 | 23.5 | NT | 101.1 | 98.9 |
| 115 | 63.0 | 14.1 | 100.4 | 62.3 |
| 116 | 40.2 | 13.9 | 100.7 | 88.3 |
| 117 | 48.0 | 23.6 | 97.1 | 80.2 |
| 119 | 39.0 | 9.2 | 96.6 | 73.6 |
| 120 | 51.6 | 20.3 | 93.2 | 71.6 |
| 123 | 49.3 | NT | 97.9 | 13.0 |

NT: Not tested.
*The compound in the form of a dihydrochloride was used as the test compound.

What is claimed is:

1. A benzothiazine derivative represented by the following formula (I):

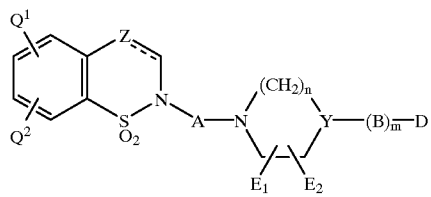

wherein the dashed line indicates the presence or absence of a bond and when the bond indicated by the dashed line is present, Z represents one of the following groups:

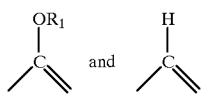

in which $R_1$ represents a substituted or unsubstituted alkyl group or a substituted or unsubstituted aralkyl group but, when the bond indicated by the dashed line is absent, Z represents one of the following groups:

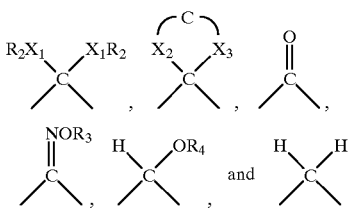

wherein $R_2$ represents a substituted or unsubstituted alkyl group, a substituted or unsubstituted aryl group or a substituted or unsubstituted aralkyl group, $R_3$ represents a hydrogen atom, a substituted or unsubstituted alkyl group, a substituted or unsubstituted aryl group or a substituted or unsubstituted aralkyl group, $R_4$ represents a hydrogen atom, a substituted or unsubstituted alkyl group or a substituted or unsubstituted aralkyl group, $X_1$, $X_2$ and $X_3$ each independently represents an oxygen atom or a sulfur atom, G represents an ethylene group with one or more of the hydrogen atoms thereof optionally substituted by a like number of halogen atoms and/or alkyl, aryl, aralkyl and/or alkylidene groups or a trimethylene group with one of more of the hydrogen atoms thereof optionally substituted by a like number of halogen atoms and/or alkyl, aryl, aralkyl and/or alkylidene groups, $Q_1$ represents a hydrogen atom, a hydroxyl group, a halogen atom, a substituted or unsubstituted alkyl group, a substituted or unsubstituted alkoxy group, a substituted or unsbustituted aralkyl gruop or a substituted or unsubstituted aralkyloxy group, $Q_2$ represents a hydrogen atom, a hydroxyl group, a halogen atom, a substituted or unsubstituted alkyl group, a substituted or unsubstituted alkoxy group, a substituted or unsubstituted aralkyl group or a substittued or unsubstituted aralkyloxy group, A represents a substituted or unsubstituted alkylene group, a substituted or unsubstituted alkenylene group or a substituted or unsubstituted alkynylene group, Y represents a nitrogen atom; and, m stands for 0 or 1, n stands for 3, and B represents a carbonyl group, a sulfonyl group, an alkylene group, an alkenylene group or a group —$CHR_7$— in which $R_7$ represents a substituted or unsubstituted alkyl group, a substituted or unsubstituted aryl group or a substituted or unsubstituted aralkyl group, $E_1$ and $E_2$ each independently represents a hydrogen atom or a lower alkyl group, and D represents a substituted or unsubstituted aromatic hydrocarbon group or a substituted or unsubstituted aromatic heterocyclic group; or a salt thereof.

2. A benzothiazine derivative or a salt thereof according to claim 1, wherein in the formula (I), Z represents the following group:

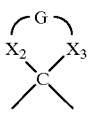

wherein G, $X_2$ and $X_3$ have the same meanings as defined above.

3. A benzothiazine derivative or a salt thereof according to claim 1, wherein in the formula (I), Z represents the following group:

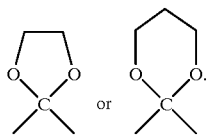 or

4. A benzothiazine derivative or a salt thereof according to claim 1, wherein in the formula (I), Z represents the following group:

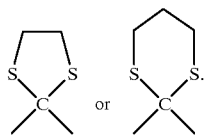 or

5. A benzothiazine derivative or a salt thereof according to claim 1, wherein in the formula (I), Z represents the following group:

wherein $R_4$ has the same meaning as defined above.

6. A benzothiazine derivative or a salt thereof according to claim 1, wherein in the formula (I), Z represents the following group:

wherein $R_1$ has the same meaning as defined above.

7. A benzothiazine derivative or a salt thereof according to claim 1, wherein in the formula (I), $Q_1$ and $Q_2$ are both a hydrogen atom.

8. A benzothiazine derivative or a salt thereof according to claim 1, wherein in the formula (I), $Q_1$ represents a hydrogen atom and $Q_2$ represents a methoxy group.

9. A benzothiazine derivative or a salt thereof according to claim 1, wherein in the formula (I), A represents an ethylene group or a trimethylene group.

10. A benzothiazine derivative or a salt thereof according to claim 1, wherein D represents a substituted or unsubstituted phenyl group.

11. A benzothiazine derivative or a salt thereof according to claim 1, wherein in the formula (I), $E_1$ and $E_2$ each represents a hydrogen atom.

12. A pharmaceutical comprising as an effective ingredient a benzothiazine derivative or a salt thereof according to claim 1.

13. A pharmaceutical according to claim 12, which is a serotonin-2 receptor antagonist.

14. A pharmaceutical according to claim 12, which is a therapeutic for circulatory diseases.

* * * * *